United States Patent
Nuzzo et al.

(10) Patent No.: US 7,705,280 B2
(45) Date of Patent: Apr. 27, 2010

(54) MULTISPECTRAL PLASMONIC CRYSTAL SENSORS

(75) Inventors: Ralph G. Nuzzo, Champaign, IL (US); John A. Rogers, Champaign, IL (US); Nathan H. Mack, Los Alamos, NM (US); Matthew Stewart, Urbana, IL (US); Viktor Malyarchuk, Urbana, IL (US); Jimin Yao, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 59 days.

(21) Appl. No.: 11/782,799

(22) Filed: Jul. 25, 2007

(65) Prior Publication Data

US 2008/0212102 A1    Sep. 4, 2008

Related U.S. Application Data

(60) Provisional application No. 60/820,254, filed on Jul. 25, 2006.

(51) Int. Cl.
*H01L 27/00* (2006.01)

(52) U.S. Cl. .................... 250/208.1; 385/129; 385/130; 385/131

(58) Field of Classification Search ............... 250/208.1; 385/129–131
See application file for complete search history.

(56) References Cited

U.S. PATENT DOCUMENTS

| | | | |
|---|---|---|---|
| 5,351,127 A | 9/1994 | King et al. |
| 5,455,178 A | 10/1995 | Fattinger |
| 6,040,936 A | 3/2000 | Kim et al. |
| 6,052,238 A | 4/2000 | Ebbesen et al. |
| 6,236,033 B1 | 5/2001 | Ebbesen et al. |
| 6,818,907 B2 | 11/2004 | Stark |
| 2002/0021445 A1 | 2/2002 | Bozhevolnyi et al. |
| 2003/0036204 A1 | 2/2003 | Stark et al. |
| 2004/0183176 A1 | 9/2004 | Naya et al. |

(Continued)

FOREIGN PATENT DOCUMENTS

WO    WO 2005/017570    2/2005

OTHER PUBLICATIONS

Altwisher et al. (Jul. 2002) "Plasmon-Assisted Transmission of Entangled Photons," *Nature* 418:304-306.

(Continued)

*Primary Examiner*—Seung C Sohn
(74) *Attorney, Agent, or Firm*—Greenlee, Winner and Sullivan, P.C.

(57) ABSTRACT

The present invention provides plasmonic crystals comprising three-dimensional and quasi comprising three-dimensional distributions of metallic or semiconducting films, including multi-layered crystal structures comprising nanostructured films and film arrays. Plasmonic crystals of the present invention include precisely registered and deterministically selected nonplanar crystal geometries and spatial distributions providing highly coupled, localized plasmonic responses in thin film elements and/or nanostructures of the crystal. Coupling of plasmonic responses provided by three-dimensional and quasi-three dimensional plasmonic crystal geometries and structures of the present invention generates enhanced local plasmonic field distributions useful for detecting small changes in the composition of an external dielectric environment proximate to a sensing surface of the plasmonic crystal. Plasmonic crystal structures of the present invention are also useful for providing highly localized excitation and/or imaging of fluorophores proximate to the crystal surface.

43 Claims, 37 Drawing Sheets

U.S. PATENT DOCUMENTS

2006/0119853 A1    6/2006    Baumberg et al.
2006/0141268 A1    6/2006    Kalkan et al.

OTHER PUBLICATIONS

Bain et al. (1989) "Formation of Monolayer Films by the Spontaneous Assembly of Organic Thiols from Solution onto Gold," *J. Am. Chem. Soc.* 111(1):321-325.

Barnes et al. (Mar. 2004) "Surface Plasmon Polaritons and Their Role in the Enhanced Transmission of Light Through Periodic Arrays of Subwavelength Holes in a Metal Film," *Phys. Rev. Lett.* 92(10):107401.

Barnes et al. (Aug. 2003) "Surface Plasmon Subwavelength Optics," *Nature* 424:824-830.

Braeuer et al. (Jul. 2001) "Precise Polymer Micro-Optical Systems," *MRS Bull.* :519-522.

Breslauer et al. (2006) "Microfluidics-Based Systems Biology," *Mil. BioSystems* 2:97-112.

Brolo et al. (2004) "Surface Plasmon Sensor Based on the Enhanced Light Transmission Through Arrays of Nanoholes in Gold Films," *Langmuir* 20:4813-4815.

Brolo et a. (2005) "Enhanced Fluorescence from Arrays of Nanoholes in a Gold Film," *J. Am. Chem. Soc.* 127(42):14936-14941.

Chang et al. (2005) "Surface Plasmon Generation and Light Transmission by Isolated Nanoholes and Arrays of Nanoholes in Thin Metal Films," *Opt. Exp.* 13(8):3150-3165.

Chou et al. (Apr. 1996) "Imprint Lithography with 25-Nanometer Resolution," *Science* 272:85-87.

Chou et al. (Jul. 2002) "Nanoprint Lithography and Lithography Induced Self-Assembly," *MRS Bull.* 26:512-517.

Cretch et al. (Jun. 2006) "Protein and Peptide Arrays: Recent Trends and New Directions," *Biomol. Eng.* 23(2-3):77-88.

Dahlin et al. (2006) "Improving the Instrumental Resolution of Sensors Based on Localized Surface Plasmon Resonance," *Anal. Chem.* 78:4416-4423.

Degiron et al. (2002) "Effects of Hole Depth on Enhanced Light Transmission Through Subwavelength Hole Arrays," *Appl. Phys. Lett.* 81:4327-4329.

Devaux et al. (2003) "Launching and Decoupling Surface Plasmons via Micro-Gratings," *Appl. Phys. Lett.* 83:4936-4938.

Diamandis et al. (1991) "The Biotin-(strept)avidin System: Principles and Applications in Biotechnology," *Clin. Chem.* 37:625-636.

Dintinger et al. (2006) "Molecule-Surface Plasmon Interactions in Hole Arrays: Enhanced Absorption, Refractive Index Changes, and All-Optical Switching," *Adv. Mater.* 18:1267-1270.

Ebbesen et al. (Feb. 1998) "Extraordinary Optical Transmission Through Sub-Wavelength Hole Arrays," *Nature* 391:667-669.

Finrschenko et al. (1998) "Flow Injection Immunoassays: A Review," *Mikrochimica Acta* 129:7-18.

Gates, B.D. (Feb. 2005) "Nanofabrication with Molds and Stamps," *Mater Today* 8(2):44-49.

Ghaemi et al. (Sep. 1998) "Surface Plasmons Enhance Optical Transmission Through Subwavelength Holes," *Phys. Rev. B*: 58(11):6779-6782.

Gordon et al. (Jan. 2004) "Strong Polarization in the Optical Transmission Through Elliptical Nanohole Arrays," *Phys. Rev. Lett.* 92(3):037401.

Haes et al. (2005) "Detection of a Biomarker for Alzheimer's Disease from Synthetic and Clinical Samples Using a Nanoscale Optical Biosensor," *J. Am. Chem. Soc.* 127(7):2264-2271.

Haes et al. (2002) "A Nanoscale Optical Biosensor: Sensitivity and Selectivity of an Approach Based on the Localized Surface Plasmon Resonance Spectroscopy of Triangular Silver Nanoparticles," *J. Am. Chem. Soc.* 124(35):10596-10604.

Hawtin et al. (Oct. 2005) "Utility of Lab-on-a-Chip Technology for High-Throughput Nucleic Acid and Protein Analysis," *Electrophoresis* 26(19):3674-3681.

Hohng et al. (2002) "Light Emission from the Shadows: Surface Plasmon Nano-Optics at Near and Far Fields," *Appl. Phys. Lett.* 81:3239-3241.

Homola et al. (1999) "Surface Plasmon Resonance Sensors: Review," *Sens. Act. B* 54:3-15.

Homola, J. (2003) "Present and Future of Surface Plasmon Resonance Biosensors," *Anal. Bioanal. Chem.* 377:528-539.

Hua et al. (2004) "Polymer Imprint Lithography with Molecular-Scale Resolution," *Nano Lett.* 4(12):2467-2471.

Huang et al. (2003) "Composite Surface for Blocking Bacterial Adosrption on Protein Biochops," *Biotechnol. Bioeng.* 81:618-624.

Hutter et al (Oct. 2004) "Exploitation of Localized Surface Plasmon Resonance," *Adv. Matter.* 16(19):1685-1706.

Johnson et al. (Dec. 1972) "Optical Constants of the Noble Metals," *Phys. Rev. B: Solid State* 6(12):4370-4379.

Jung et al. (1998) "Self-Assembled Monolayers from Organosulfour Compounds: A Comparison Between Sulfides, Disulfides, and Thiols," *Langmuir* 14:1103-1107.

Jung et al. (1998) "Quantitative Interpretation of the Response of Surface Plasmon Resonance Sensors to Adsorbed Films," *Langmuir* 14:5636-5648.

Kalyuzhny et al. (2002) "Transmission Surface-Plasmon Resonance (T-SPR) Measurements for Monitoring Adsorption on Ultrathin Gold Island Films," *Chem. Eur. J.* 8(17):3849-3857.

Kato et al. (Oct. 2005) "Analysis of Amino Acids and Proteins Using a Poly(Methyl Methacrylate) Microfluidic System," *Electrophoresis* 26(19):3682-3688.

Kim et al. (Oct. 2003) "Microscopic Origin of Surface-Plasmon Radiation Band-Gap Nanostructures," *Phys. Rev. Lett.* 9(14)1:143901.

Kim et al. (1999) "Control of Optical Transmission Through Metals Perforated with Subwavelength Hole Arrays," *Opt. Lett.* 24(4):256-258.

Knoll et al. (1998) "Interfaces and Thin Films as Seen by Bound Electromagnetic Waves," *Ann. Rev. Phys. Chem.* 49:569-638.

Kyo et al. (2005) "Label-Free Detection of Proteins in Crude Cell Lysate with Antibody Arrays by a Surface Plasmon Resonance Imaging Technique," *Anal. Chem.* 77(22):7115-7121.

Lezec et al. (2004) "Diffracted Evanescent Wave Model for Enhanced and Suppressed Optical Transmission Through Subwavelength Hole Arrays," *Opt. Exp.* 12(16):3629-3651.

Lin et al. (2004) "Surface Plasmon Resonance-Based Sensors to Identify Cis-Regulatory Elements," *Anal. Chem.* 76(22):6555-6559.

Liu et al. (2004) "Biosensing Based Upon Molecular Confinement in Metallic Nanocavity Arrays," *Nanotechnology* 15:1368-1374.

Loo et al. (2002) "Additive, Nanoscale Patterning of Metal Films with a Stamp and a Surface Chemistry Mediated Transfer Process: Applications in Plastic Electronics," *Appl. Phys. Lett.* 81:562-564.

Loo et al. (2002) "Interfacial Chemistries for Nanoscale Transfer Printing," *J. Am. Chem. Soc.* 124(26):7654-7655.

Mack et al. (Feb. 2007) "Optical Transduction of Chemical Forces," *Nano Lett.* 7(3):733-737.

Maier et al. (2005) "Plasmonics: Localization and Guiding of Electromagnetic Energy in Metal/Dielectric Structures," *J. Appl. Phys.* 98:011101.

Malinsky et al. (2001) "Chain Length Dependence and Sensing Capabilities of the Localized Surface Plasmon Resonance of Silver Nanoparticles Chemically Modified with Alkanethiol Self-Assembled Monolayers," *J. Am. Chem. Soc.* 123(7):1471-1482.

Malyarchuk et al. (2005) "High Performance Plasmonic Crystal Sensor Formed by Soft Nanoimprint Lithography," *Opt. Expr.* 13(15):5669-5675.

Mozsolits et al. (Feb. 2003) "Surface Plasmon Resonance Spectroscopy in the Study of Membrane-Mediated Cell Signaling," *J. Pept. Sci.* 9(2):77-89.

Murray et al. (Apr. 2004) "Transition from Localized Surface Plasmon Resonance to Extend Surface Plasmon-Polaration as Metallic Nanoparticles Merge to From Periodic Hole Array," *Phys. Rev. B* 69(16):165407.

Nath et al. (2002) "A Colorimetric Gold Nanoparticle Sensor to Interrogate Biomolecular Interactions in Real Time on a Surface," *Anal. Chem.* 74(3):504-509.

Prikulis et al. (2004) "Optical Spectroscopy of Nanometric Holes in Thin Gold Films," *Nano Lett.* 4(6):1003-1007.

Raether, H. (1988) *Surface Plasmons on Smooth and Rough Surfaces and on Gratings*, Springer-Verlag: New York, vol. 111:136-.

Ramachandran et al. (Nov. 2005) "Emerging Tools for Real-Time Label-Free Detection of Interactions on Functional Protein Microarrays," *FEBS J.* 272(21):5412-5425.

Resnick et al. (Feb. 2005) "Step and Flash Imprint Lithography," *Mater. Today* 8(2):34-42.

Rich et al. (2004) "Why You Should be Using more SPR Biosensor Technology," *Drug Disc. Today: Technol.* 1(3):301-308.

Rich et al. (Mar. 2003) "Spying on HIV with SPR," *Trends Microbiol.* 11(3):124-133.

Rindzevicius et al. (2005) "Plasmon Sensing Characteristics of Single Nanometric Holes," *Nano Lett.* 5(11):2335-2339.

Rogers et al. (Feb. 2005) "Recent Progress in Soft Lithography," *Mater. Today* :50-56.

Rogers, J.A. (2001) *MRS Bull.* 26L:530-534.

Ropers et al. (2005) "Fentosecond Light Transmission and Subradiant Damping in Plasmonic Crystals," *Phys. Rev. Lett.* 94:113901.

Srinivasan et al. (2004) "An Integrated Digital Microfluidic Lab-on-a-Chip for Clinical Diagnostics on Human Physiological Fluids," *Lab on a Chip* 4:310-315.

Stuart et al. (Feb. 2005) "Biological Applications of Localized Surface Plasmonic Phenomenae," *IEE Proc. Nanobiotechnol.* 152(1):13-32.

Su et al. (2005) "Surface Plasmon Resonance Spectroscopy and Quartz Crystal Microbalance Study of Streptavidin Film Structure Effects no Biotinylated DNA Assembly and Target DNA Hybridization," *Langmuir* 21(1):348-353.

Sun et al. (2003) *The Analyst* 128:686-691.

Taflove et al. (2005) *Computational Electrodynamics: The Finite-Difference Time-Domain Method*, 3$^{rd}$ ed., Artech House: Boston, pp. 772-812.

Tetz et al. (2006) "High-Resolution Surface Plasmon Resonance Sensor Based on Linewidth-Optimized Nanohole Array Transmittance," *Opt. Latt.* 31(10):1528-1530.

Thio et al. (2002) "Giant Optical Transmission of Sub-Wavelength Apertures: Physics and Applications," *Nanotechnology* 13:429-432.

Tomizaki et al. (May 2005) "Protein-Detecting Microarrays: Current Accomplishments and Requirements," *ChemBioChem* 6(5):782-799.

Wertz et al. (2001) "Effect of Surface Hydrophobicity on Adsorption and Relaxation Kinetics of Albumin and Fibrinogen: Single-Species and Competitive Behavior," *Langmuir* 17(10):3006-3016.

Wilcheke t al. (1990) "Introduction to Avidin-Biotin Technology," *Methods Enzymol.* 184:5-13.

Wilde et al. (2001) "Molecular Patterning on Carbon Nased Surfaces Through Photobiotin Activation," *The Analyst* 126:195-198.

Williams et al. (2004) "Use of the Extraordinary Infrared Transmission of Metallic Subwavelength Arrays to Study the Catalyzed Reaction of Methanol to Formaldehyde on Copper Oxide," *J. Phys. Chem. B.* 108:11833-11837.

Xia et al. (1999) "Unconventional Methods for Fabricating and Patterning Nanostructures," *Chem. Rev.* 99:1823-1848.

Zaumseil et al. (2003) "Three-Dimensional and Multilayer Nanostructures Formed by Nanotransfer Printing," *Nano Lett.* 3(9):1223-1227.

International Search Report, Corresponding to International Application No. PCT/US07/74293, Mailed Jul. 24, 2008.

Brolo, A.G. et al., (2005) "The development of surface-plasmon-based sensors using arrays of sub-wavelength holes," *Proc. of SPIE*, 6002, 600207.

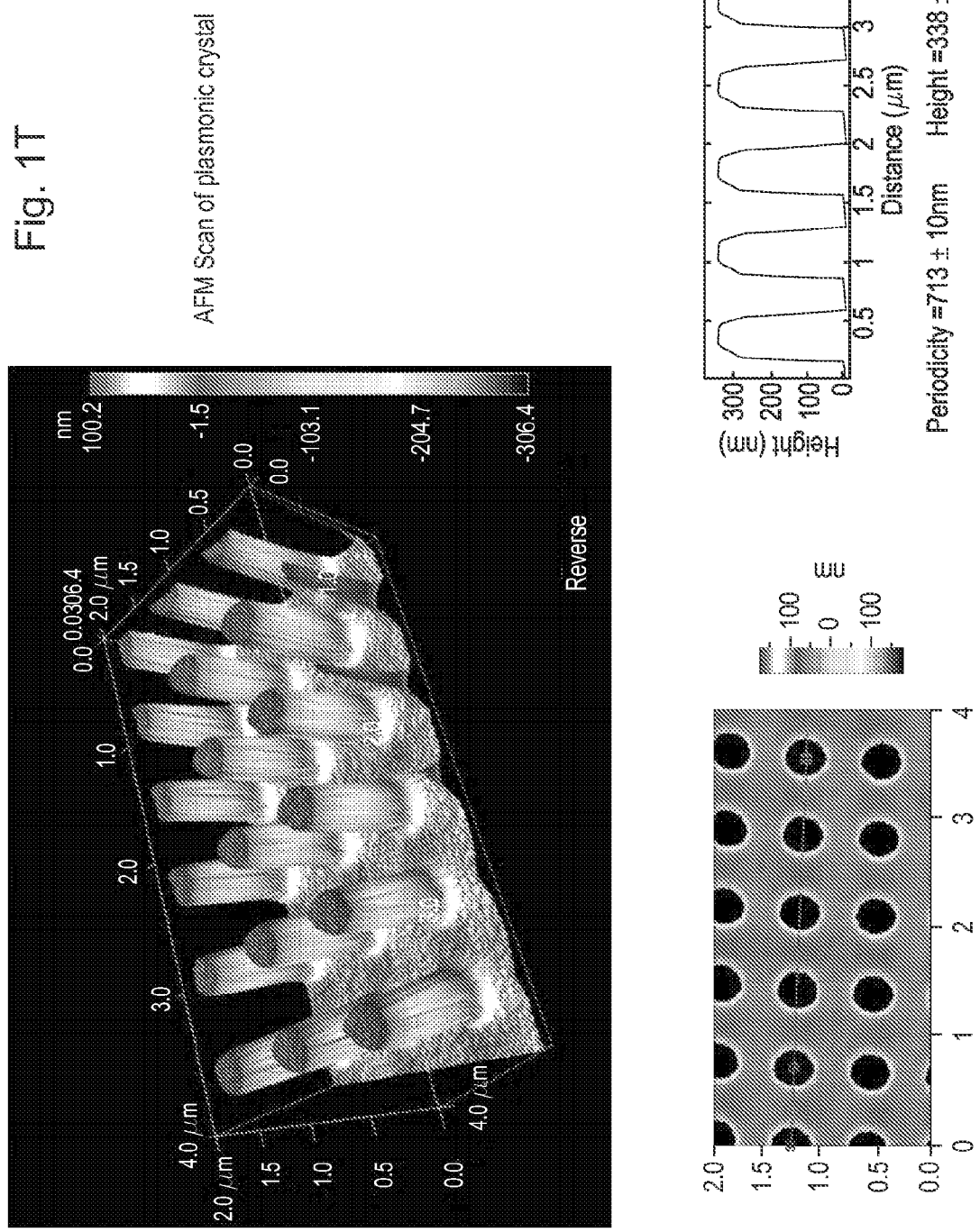

A    Brillouin zone mapping of sputter coated sample

B    Absolute sensitivity of SAMs

MULTISPECTRAL PLASMONIC CRYSTAL SENSORS

CROSS-REFERENCE TO RELATED APPLICATIONS

This application claims priority under 35 U.S.C. 119(e) to U.S. provisional Patent Application 60/820,254 filed Jul. 25, 2006, which is hereby incorporated by reference in its entirety.

STATEMENT REGARDING FEDERALLY SPONSORED RESEARCH OR DEVELOPMENT

This invention was made with government support awarded by the following agencies: DOE grant DEFG02-91-ER45439. The United States government has certain rights in the invention.

BACKGROUND OF INVENTION

Over the last decade, surface plasmon resonance (SPR) microscopy has emerged as a broadly applicable analytical tool for detecting and characterizing chemical and physical changes occurring in a highly localized probed region. Compatible with a wide range of condensed phase and gas phase environments, SPR is a virtually universally applicable sensing platform. In addition, SPR methods provide high detection sensitivities and excellent temporal resolution, and are compatible with a number of high throughput screening systems, such as microfluidic, nanofluidic and microarray systems. As a result of these beneficial attributes, a great deal of attention has been directed over the last several decade at developing SPR-based sensors capable of real time characterization of the composition, physical properties and optical properties (e.g., index of refraction) of a range of materials in a variety of media.

Surface plasmons (SPs), also know as surface plasmon waves and plasmon polaritons, are charge density waves, which propagate parallel to an interface between a conducting or semiconducting thin film and a dielectric layer. Surface plasmon resonance (SPR) microscopy uses resonant excitation of SPs to detect and characterize chemical and physical changes occurring in a probed region proximate to the sensing surface of thin metal or semiconductor films. In these systems, SPs are generated by coupling radiant energy from incident photons into the oscillating modes of free electrons present in a conducting material. Conventional SPR sensors achieve photon to SP coupling by interaction of evanescent electromagnetic waves generated via total internal reflection with a thin metallic or semiconducting layer. SPs are localized at the surface of the conducting (including semiconducting) layer and the intensity of the electric field of a SP decays exponentially in directions perpendicular to the plane in which it propagates. The highly localized nature of SP's excited by evanescent electromagnetic waves makes this technique ideally suited for sensing changes in a spatially localized probe region proximate to (<about 500 nanometer) the SPR sensing surface.

In recent years, SP sensors have been used extensively to characterize chemical and physical properties of a variety of biological materials. For example, surface plasmon resonance (SPR) instruments are widely used to study macromolecular biological interactions. Important applications of this technology include proteomics, virology, cell signaling, DNA hybridization, antibody-antigen interactions, DNA-protein interactions, and drug discovery. Commonly, these SPR applications involve sensing specific and/or nonspecific protein interactions with surface immobilized target species by detecting them on the basis of the sensitivity of SPR to even minute changes in refractive index occurring near the surface of a conducting material. Accordingly, SPR provides a virtually universally applicable form of chemical sensing, that can be effected without the need for prior spectroscopic (e.g., fluorescent) labeling. SPs have also been used, however, as a means of locally exciting fluorescent materials, such as fluorescently labeled probes. In these systems, energy from SPs is coupled to electron transitions in a fluorescent species in a manner providing highly localized excitation and emission.

Sensors based on SPR utilize the dependence of the SPR resonance condition on changes in the refractive index of a lower refractive index dielectric sample layer positioned adjacent to the thin electrically conducting film that supports SP generation. In typical sensing applications, changes in the resonance condition for formation of SPs are monitored in real time and directly related to chemical or physical changes occurring at an interface between the thin metal (or semiconductor) film and the media undergoing analysis. Sensors based on SPR may provide selective detection of materials and compounds by manipulating the chemical or physical properties of the sensing surface. In some applications, for example, the sensing surface of the SPR sensor is coated with a material exhibiting selective binding characteristics such that the refractive index varies in the presence of a specific material to be sensed. For example, the sensing surface may be made sensitive to a particular antibody by coating it with an antigen to that antibody. Using these principles, SPR detection has been successfully incorporated into a number of commercially available biological sensing devices including the sensors and screening devices manufactured by BIAcore, Inc.

Most commercial SPR systems use the Kretschmann configuration where a prism couples light, under total internal reflection, into surface plasmons (SPs) on flat, continuous gold films. In the Kretschmann geometry, evanescent electromagnetic waves penetrate the thin (≈50 nm) gold film(s) positioned between higher and lower refractive index dielectric layers and excite SPs, which propagate parallel to the outer surface of the metal film adjacent to a lower refractive index layer. The prism is needed in this configuration to achieve a wavevector matching condition between the incident polarized excitation light and the surface plasmons. For a given dielectric sample, photons of a certain wavelength and incident at a certain angle generate evanescent waves that penetrate the metal layer and excite surface plasmons at the metal-dielectric sample interface. Upon exciting SPs, the intensity of reflected light is reduced and, therefore, monitoring changes in the intensity of the reflected beam or measurement of the wavelength corresponding to the minimum intensity of reflected light can be used to detect change in refractive index in the localized probe region.

The Kretschmann SPR optical configuration, while highly sensitive (a Figure of Merit, FOM, of greater than about 1000 nm/RI is typical), is subject to several practical limitations. First, it is difficult to integrate theses optical configurations into complex form factor devices useful for high throughput fluidic screening applications, including microfluidic (μFl) and nanofluidic (nFl) systems for bioanalytical measurement. Kretschmann geometry based sensors assemblies using angle of incidence modulation require complex and spatially restrictive rotation assembles that are prohibitive for some applications and require frequent realignment and optimization. Second, the mechanical integrity of these systems may not be robust enough for important large-area, array-based screening applications. To address such limitations and extend the sensitivity of conventional SPR systems, specifically tailored nanoscale materials structures capable of generating plasmonic responses have attracted considerable attention for implementation in the next generation of SPR sensors.

Nanoparticle arrays, for example, can provide extremely sensitive and tunable plasmonic responses. These architectures require, however, external optical systems through which the array/nanoparticles can be spectroscopically interrogated, and therefore are less attractive for large-area, array-based screening applications. Further, significant deviations in nanoparticle positions and sizes provide practical limitations on the use of nanoparticle arrays for SPR sensing.

An alternative method of coupling incident electromagnetic radiation into plasmon modes involves the use of periodically structured metal thin films, such as nanohole arrays, where the coupling is dictated by the matching of photon and grating momenta, with the latter acting as its own optical device. Such plasmonic crystal structures, for example structures exhibiting enhanced transmission of light through their subwavelength apertures, appear promising for application in a range of optical technology areas, including sensing involving plasmonic responses. The nature and specific mechanisms of plasmon generation in these structures are subjects of substantial interest in research and, while incompletely understood, are known to involve the excitation of surface plasmon polaritons (SPPs) with contributions arising from surface plasmon resonances localized at the edges of the holes (LSPRs). The transmission spectra of these devices depend strongly on the properties of the fabricated holes (shape, size, period, structure) as well as the thickness of the metal and the index of the underlying and external media. While surface plasmon responses accessed using metal thin films is well established, application of these structures for SPR sensing has not yet been fully explored.

It will be appreciated from the foregoing that a clear need exists for methods and systems for generating plasmonic responses in thin electrically conducting films for use in sensing applications. SPR sensors are needed that are compatible with direct integration into complex device architectures such as microfluidic Lab on Chip (LOC) systems. SPR sensors are needed having form factors, sensitivities and time resolutions that are suitable for high throughput screening applications including implementation in fluidic and microarray systems. In addition, low cost, high precision and commercially practicable methods are required for fabricating SPR sensors, particularly SPR sensors based on plasmonic crystals.

SUMMARY OF THE INVENTION

The present invention provides plasmonic crystals comprising three-dimensional and quasi comprising three-dimensional distributions of metallic or semiconducting films, including multi-layered crystal structures comprising nanostructured films and film arrays. Plasmonic crystals of the present invention include precisely registered and deterministically selected nonplanar crystal geometries and spatial distributions providing highly coupled, localized plasmonic responses in thin film elements and/or nanostructures of the crystal. Coupling of plasmonic responses provided by three-dimensional and quasi-three dimensional plasmonic crystal geometries and structures of the present invention generates enhanced local plasmonic field distributions useful for detecting small changes in the composition of an external dielectric environment proximate to a sensing surface of the plasmonic crystal. Plasmonic crystal structures of the present invention are also useful for providing highly localized excitation and/or imaging of fluorophores proximate to the crystal surface.

Plasmonic crystals of the present invention enable a robust optical sensing platform for high performance chemical and biological sensing. Sensors, sensing methods and sensing systems of the present invention are capable of multispectral spectroscopic SPR sensing and/or spatially resolved SPR imaging for detecting and characterizing the optical properties, chemical compositions and/or physical properties of variety of materials. Sensors of the present invention are compatible with compact form factors and are capable of direct, low cost integration into a range of delivery and high throughput screening systems, including microfluidic, nanofluidic and microarray systems and formats. Sensors and sensing methods of the present invention provide exceptional sensitivities (e.g., Figure of Merit ranging from about 100 nm/RI to about 700 nm/RI), good spatial resolution imaging and are capable of label-free quantitative detection of a wide variety of analytes, including biological molecules and therapeutic drug candidates. In some embodiments wherein full multispectral intensity is accessed during measurement, sensitivities on the order of 22,000 nm·% T RI$^{-1}$ are achievable for a photonic crystal sensor of the present invention having a photonic crystal with a multilayer film geometry and sensitivities on the order of 44,000 nm·% T RI$^{-1}$ are achievable for a photonic crystal sensor of the present invention having a photonic crystal with a continuous film geometry.

The present invention also provides methods for fabricating plasmonic crystals via a combination of soft lithographic patterning and thin film deposition techniques. Processing methods of the present invention provide a versatile, low cost and commercially attractive imprinting-based or replica molding-based fabrication platform for making two-, three- and quasi three-dimensional plasmonic crystals having preselected thin film and/or nanostructured geometries, including three-dimensional multilayered crystal geometries. The present plasmonic crystal fabrication methods enable nonplanar integration of precisely registered thin film elements having accurately selected physical dimensions and spatial orientations. Processing methods of the present invention access two-, three- and quasi three dimensional plasmonic crystal geometries comprising thin film element arrays and feature arrays having one or more physical dimensions (e.g., length, width, thickness, diameter, radius etc.) ranging from 10s of nanometers to 1000s of microns.

In one aspect, the present invention provides three-dimensional plasmonic crystals comprising a three-dimensional, and optionally multilayered distribution, of films of electrically conducting crystal elements including nanostructured thin film elements. In one embodiment, the present invention provides a plasmonic crystal comprising: (i) a substrate having a first surface with a plurality of features provided in a first array, the substrate comprising a dielectric material; and (ii) one or more films comprising an electrically conductive material, wherein at least a portion of the one or more films is supported by the first surface, and wherein at least a portion of the one or more films comprising the electrically conducting material is spatially aligned with each of the features of the first surface. The films of electrically conducting material in the present plasmonic sensors comprise an electrically conducting material capable of supporting plasmonic responses, such as a metal, an organic or inorganic semiconductor or combination of a metal and a semiconductor. The spatial distribution, physical dimensions or both of the features of the first array are selected such that at least a portion of electromagnetic radiation incident to the plasmonic crystal excites plasmonic responses in the one or more films comprising the electrically conducting material.

Features of the first array of the first surface of the substrate useful in the present invention include apertures, recessed features, relief features or any combination of these. In an embodiment, for example, features of the first array comprise apertures extending through the entire thickness of the substrate, and optionally comprise a nanohole array. In other embodiments, features of the first array comprise relief features extending from the substrate, including but not limited to, arrays of cubes, columns, ribbons, posts and prisms or any combination of these relief features. In other embodiments, features of the first array comprise recessed features extending into the substrate including, but not limited to, depressions, channels, grooves, bores, openings, slits or any combination of these.

In certain embodiments, features of the first array are nanosized features. In the context of the present description, the term "nanosized" refers to features having at least one physical dimension, such as a cross sectional dimension (e.g., width, length, radius, diameter etc.), that is less than about one micron. Arrays of the present invention include nanopillar arrays and nanohole arrays. Relief features, recessed features or apertures useful for some embodiments, for example, extend away from the substrate or extend into the substrate a height selected from the range of 5 nanometers to 5 microns. Features of the substrate in some embodiments have submicron cross sectional dimensions (widths, length, diameter, radius, etc.), such as cross sectional dimensions less than 1 micron, in other embodiments less than 500 nanometers, in other embodiments less than 100 nanometers or in other embodiments less than 50 nanometers. Features of the substrate of plasmonic crystals of the present invention may have a range of cross sectional shapes including but not limited to circular, square, rectangular, trapezoidal, ellipsoid, triangular or any combination of these shapes.

Features of the first array, and optionally films of the plasmonic crystal, may be provided in a periodic array, optionally including but not limited to periodic arrays having one or more defects. The term defect, as used in this context, is used consistently with the general meaning of this term as understood in the fields of photonics and plasmonic crystal sensing. Defects may include one or more missing features in a periodic array, one or more additional features in a periodic array or one or more features having physical dimensions substantially different (e.g., a deviation of 20% or larger) than other features of the periodic array. Use of substrates having nanosized features provided in a periodic first array is useful in the present invention for exciting plasmonic responses in one or more films of electrically conducting materials provided on the dielectric substrate.

In an embodiment, the plasmonic crystal comprises a continuous film supported by the first surface of the substrate. In this embodiment, the continuous film covers at least a portion of the plurality of features provided in the first array, for example, by at least partially covering recessed features, relief features, and/or apertures in the substrate. In an embodiment, the continuous film entirely covers the first surface of the substrate. Optionally, the continuous film of this embodiment is a unitary film. In some embodiments, the continuous film of this embodiment is provided in physical contact with the first surface of the substrate, and optionally is provided in conformal contact with the first surface of the substrate. An advantage of plasmonic crystals of the present invention comprising a continuous film of electrically conductive material is that they are responsive to electromagnetic radiation having wavelengths in the visible region of the electromagnetic spectrum, and thus can be conveniently and sensitively readout using visible light optical sources and photodetectors responsive to visible light. Plasmonic crystals of the present invention comprising a continuous film of electrically conductive material are also robust, mechanical stable and exhibit long useful lifetimes.

Continuous films useful in these embodiments may have a substantially uniform thickness (e.g., thickness uniform to with in 90%) or thicknesses that varies with position on the first surface of the substrate. In an embodiment, the continuous film covers the bottom surfaces of recessed features in the substrate, the top surfaces of relief features in the substrate and/or the side surfaces of recessed features, relief features or apertures in the substrate. The first film is provided in a first layer and the films of the second array are provided in a second layer physically displaced from the first layer. In a specific embodiment, a multilayer plasmonic crystal of the present invention further comprises an additional substrate in contact with the substrate having the first surface, wherein at least a portion of the features of the first array are apertures extending through the substrate having the first surface, wherein the additional substrate is positioned such that the apertures in the substrate having the first surface expose exposed regions of the additional substrate, and wherein the continuous film of the photonic crystal covers at least a portion of the exposed regions of the additional substrate. In an embodiment, the continuous film provided to the dielectric substrate is generated using a sputtering deposition technique, such as ion beam sputtering.

In another embodiment of this aspect, a plasmonic crystal of the present invention comprises a first film supported by a portion of the first surface, and a plurality of films provided in a second array, wherein at least one of the films of the second array is spatially aligned with each of the features of the first surface. In a specific embodiment of this aspect of the present invention, at least a portion of the films of the second array are physically displaced from the first film, for example, vertically displaced along one or more axes that intersect the first surface of the substrate. In some embodiments the films of the second array are not in physical contact with the first film of the first layer. In some embodiments, for example, the first film is physically separated from the array of second films by distances selected over the range of about 5 nanometers to about 5 microns. In an plasmonic crystal comprising a substrate having a first array of features comprising recessed features having bottom surfaces or relief features having top surfaces, for example, a portion of the films of the second array are positioned on the bottom surfaces or the top surfaces of the recessed or relief features, respectively. In an embodiment, for example, films of the second array are discs or plate-shaped thin film structures provided on the bottom surfaces of recessed features of the first array of substrate and/or provided on the top surfaces of relief features of the first array of the substrate. In an embodiment, the first film supported by the first surface has a plurality of apertures corresponding to recessed features, relief features or apertures of the first array.

In a specific embodiment of this aspect, the invention provides a plasmonic crystal having a three dimensional multilayered geometry, wherein the first film is provided on the external surface of the first layer, and the films of the second array are provided on a surface of a second layer provided in contact with the first layer. In another specific embodiment, the first film does not cover the recessed or relief features of the first array, and films of the second array are provided on bottom surfaces of the recessed features and/or the top surfaces of the relief features. In another specific embodiment, the first film partially or fully covers the recessed or relief features of the first array. In an embodiment, the first array of features of the substrate comprises recessed features, relief features or apertures having side surfaces, and the plasmonic crystal further comprise films covering at least a portion of the side surfaces of the features. Films of the second array in some embodiments have submicron cross sectional dimensions (widths, length, diameter, radius, etc.), such as cross sectional dimensions less than 1 micron, in other embodiments less than 500 nanometers, in other embodiments less than 100 nanometers or in other embodiments less than 50 nanometers.

The present invention provides plasmonic crystal geometries having a three-dimensional distribution or quasi three dimensional distribution, and optionally multilayered distribution, of films of electrically conducting crystal elements capable of providing highly coupled plasmonic responses in the thin film elements of the crystal. In an embodiment, for example, the features of the first array are spatially aligned with the films of the second array such that plasmonic responses generated in the first film couple to plasmonic responses generated in the films of the second array. In an embodiment, for example, the first film is separated from the films of the second array by a distance small enough that plasmonic responses generated in the first film couple to plasmonic responses generated in the films of the second array. As used in this context, the term "couple" refers to physical and/or electrodynamic processes involving one or more materials, such as electrically conducting films, that have a measurable effect on the quantum states of electrons participating in an interaction.

Nanostructured dielectric substrates are particularly useful for positioning and supporting thin film device elements of plasmonic crystals of the present invention. In a particularly useful embodiment, the first surface supporting at least a portion of the films of electrically conducting material is an external surface of a nanostructured dielectric substrate. Nanostructured dielectric substrates are useful in the present invention for deterministically defining, preselecting and accurately spatially addressing the positions, spatial orientations and physical dimensions of films, including nanostructured and/or nanosized films, and/or nanostructured crystal elements of plasmonic crystals of the present invention, particularly in multilayer three dimensional and quasi three dimensional plasmonic crystal geometries. Nanostructured dielectric substrates are useful in the present invention for generating complex multilayer plasmonic crystal geometries having electrically conducting films provided on two or more physically separated layers, such as an external surface and surfaces embedded or raised from the external surface. In specific embodiments, the dielectric substrate of photonic crystals of the present invention comprise a nanostructured layer of a dielectric material.

Dielectric substrates in plasmonic crystals of the present invention may comprise any material providing useful optical and mechanical properties including polymer materials, such as polyurethane. Dielectric substrates useful in plasmonic crystals of the present invention include nanostructured dielectric elements such as imprinted or molded substrates having an array of recessed and/or relief features. Useful dielectric substrates include nano-imprinted and replica molded substrates. Imprinted and molded dielectric substrate structures are useful in plasmonic crystals of the present invention because they are capable of providing a low cost substrate layer for accessing complex multilayer nanostructured thin film distributions.

Three-dimensional plasmonic crystals of the present invention include crystal geometries wherein the films of electrically conducting material are provided in a configuration comprising a metallic or semiconducting optical grating structure. In one embodiment, for example, a plasmonic crystal of the present invention has a multilayered optical grating geometry wherein a first film is provided on a first layer having the first surface and a plurality of discrete films are provided in a second array on a second layer of the plasmonic crystal. In these embodiments, the first layer having the first film is physically displaced (e.g. vertically displaced) from the second layer having the secondary array of films by selected distance along an axis that intersects the first surface. In some embodiments, first and second layers of the plasmonic crystal are separated by a distance selected over the range of about 5 nanometers to about 5 microns. However, plasmonic crystals of the present invention having a larger first and second layer separation are useful for other applications, and the fabrication methods provided herein are capable of accessing such multilayer structures having such larger layer separations. The present invention includes multilayer plasmonic crystal geometries having nanosized and/or nanostructured films provided in or on more than two layers.

The physical dimensions, shapes and spatial orientations of films, including nanosized and nanostructured metal and/or semiconductor films, and features, including recessed features, relief features and apertures, at least in part, determine the optical properties of plasmonic crystals of the present invention and, thus, in part define the utility of these structures for advanced chemical and biological sensing applications. The present invention includes plasmonic crystals comprising a single continuous film supported by one or more nanostructured substrates. Alternatively, the present invention includes plasmonic crystals comprising a plurality of independent and spatially discrete films supported by one or more nanostructured substrates. The present invention includes embodiments wherein one or more films of electrically conductive material comprise metal or semiconductor thin films having thicknesses selected from the range of about 5 nanometers to about 5 microns, and have uniform or nonuniform thicknesses. Use of thicker metal or semiconductor thin films is beneficial for sensors capable of reflection mode for readout and use of thinner metal or semiconductor thin films is beneficial for sensors capable of a transition mode for readout. The present invention includes plasmonic crystals having one or more films of electrically conducting material, for example provided in a second array configuration, having cross sectional shapes selected from the group consisting of circular, square, rectangular, trapezoidal, ellipsoid, triangular, polygonal or any portion or combination of shapes these. In an embodiment, the one or more films of electrically conducting materials of a plasmonic crystal of the present invention further comprises one or more adhesion layers or adhesion materials to promote binding or positioning of the film(s) on the dielectric substrate. Adhesion layers and materials comprising nonmetal materials that do not affect significantly the plasmon excitation process are preferred for some embodiments. Exemplary adhesion layers or materials in these embodiments include, but are not limited to, tin oxide, barium oxide and organosilane adhesion layers or materials.

In an embodiment of the present invention, a three dimensional plasmonic crystal comprises: (i) a first surface having a first array of features, wherein at least a portion of the first surface supports a first film; and (ii) a second array of films, wherein at least one of the films of the second array is spatially aligned with each of the features of the first surface, and wherein at least a portion of each of the films of the second array is physically displaced from the first film along axes that intersect the first surface. The first film and the films of the second array comprise an electrically conducting material capable of supporting plasmonic response, such as a metal, a semiconductor or combination of a metal and a semiconductor. The spatial distribution, physical dimensions or both of the features of the first array and the films of the second array are selected such that incident electromagnetic radiation directed onto the plasmonic crystal is capable of exciting plasmonic responses in the first and second layers. In an embodiment, the first film is provided in a first layer and the films of the second array are provided in a second layer such that the plasmonic crystal has a three dimensional multilayered geometry.

Plasmonic crystals of the present invention may further comprise one or more additional films comprising electrically conducting material, including additional nanosized and/or nanostructured films. In one embodiment, addition films are provided comprising: (i) an additional film supported by a additional surface having a additional array of features, wherein the features of the additional array are spatially aligned with the features of the first surface; and/or (ii) an additional array of films, wherein films of the additional array comprise an electrically conducting material, wherein the films of the additional array are spatially aligned with the features of the first surface. The present invention includes complex multilayer plasmonic crystal geometries wherein nanostructure elements, such as thin metal or semiconductor films, are positioned in more that two physically displaced layers.

In another embodiment, the present invention provides SPR sensors and sensing systems useful for sensing, detecting and/or imaging optical properties, physical properties and compositions of molecules. In one embodiment, a sensor of the present invention comprises: (i) an optical source for generating incident electromagnetic radiation, such as a polarized beam of electromagnetic radiation; (ii) a plasmonic crystal positioned to receive the beam of incident electromagnetic radiation, and (iii) a detector positioned to receive electromagnetic radiation transmitted, scattered or reflected by the plasmonic crystal; wherein the detector is capable of detecting changes in the intensity of electromagnetic radiation transmitted, scattered or reflected. Plasmonic crystals useful for sensors of this embodiment include all geometries, configurations, compositions and variations provided throughout the present description including, but not limited to, multilayer three-dimensional distributions of metallic and semiconductor films, three dimensional and quasi three dimensional distributions of nanosized and/or nanostructured films, and plasmonic crystals having multilayer geometries comprising spatially aligned nanosized and/or nanostructured films and film arrays. Detectors useful in the sensors and sensing methods of the present invention include multispectral photodetectors for monitoring intensities at a plurality of wavelengths and two dimensional photodetectors for SPR imaging applications.

In one embodiment, the plasmonic crystal of the SPR sensor comprises: (i) a substrate having an first surface with a plurality of features provided in a first array, the substrate comprising a dielectric material; and (ii) one or more films comprising an electrically conductive material, wherein at least a portion of the one or more films is supported by the first surface, and wherein at least a portion of the one or more of the films comprising the electrically conducting material is spatially aligned with each of the features of the first surface; wherein the spatial distribution, physical dimensions or both of the features of the first array are selected such that at least a portion of the electromagnetic radiation incident to the plasmonic crystal excites plasmonic responses in the one or more films comprising the electrically conducting material. In one embodiment, a plasmonic crystal useful in sensors of the present invention further comprises an imprinted or molded dielectric substrate, such as a nano-imprinted or replica-molded substrate, supporting a plurality of thin film elements, such as nanostructured thin film elements. Imprinted and molded dielectric substrates are useful for providing two- and three-dimensional plasmonic crystals for SPR sensors of this aspect of the present invention having very accurately selected optical characteristics.

SPR sensors of the present invention may further comprise a means for providing a material to be sensed, including biomolecules, therapeutic candidates and other analytes, to a probe region proximate to one or more sensing surfaces of the sensor. In the present invention, films of electrically conducting material comprise the sensing surface of SPR sensors, including nanosized and/or nanostructured films. In one embodiment, the means for providing a material to be sensed transports molecules, such as biomolecules and/or therapeutic candidates into (and optionally through) the probe region proximate to the sensing surface. In the context of sensors and sensing methods providing high detection and imaging sensitivities the term "proximate" refers to within about 500 nanometers of a sensing surface. The present invention includes sensors and sensing application, however, wherein proximate refers to probe region that extends further than 500 nanometers from the sensing surface, for example in sensing applications wherein molecules integrated into cellular material are detected and characterized. Exemplary means for providing a material to be sensed proximate to the sensing surface include fluidic delivery systems such as microfluidic and/or nanofluidic systems; and microarray systems. The present invention includes sensors wherein the plasmonic crystal is an integrated component of a microarray system, nanofluidic system or a microfluidic system.

The present invention also includes SPR sensors wherein an external surface of the SPR sensor, such as one or more sensing surfaces of the sensor (e.g., the first film and/or films of the second array), is functionalized to provide selective binding to one or more molecules to be sensed, such as analytes, biomolecules and therapeutic candidates. In these sensing systems, functionalization of surfaces of the SPR sensor is a means of providing selected molecules to the probe region of the sensor, for example molecules having a selected composition and/or binding characterisitics. In exemplary embodiments, a surface proximate to the probe regions, such as the sensing surface of the sensor, is functionalized by incorporation of one or more molecules, including proteins, peptides, oligonucleotides, DNA molecules, RNA molecules, lipids, carbohydrates, polysaccharides; glycoproteins, lipoproteins, sugars and candidate molecules, into films of the plasmonic crystal. In an embodiment, analytes are transported through a flow cell having an integrated SPR sensor, and analytes that bind to the functionalized external surface of the sensor are selectively detected and characterized. Functionalization of the SPR sensor in these embodiments, therefore, provides a means of providing selective SPR sensing. SPR sensors having functionalized external surfaces are particularly useful for high throughput screening, proteomics and/or drug discovery applications.

Detectors useful for SPR sensors of the present invention include, but are not limited to, multispectral detectors capable of detecting and/or measuring changes in the intensities of electromagnetic radiation at two or more wavelengths. Multispectral detectors in the present invention are useful for sensors capable of multispectral SPR sensing and imaging providing enhanced sensitivities. In an embodiment, the multispectral detector of the SPR sensor is capable of measuring changes in the intensities of electromagnetic radiation transmitted, scattered or reflected by the plasmonic crystal at plurality of wavelengths or wavelength distributions. In an embodiment, the multispectral detector of the SPR sensor is capable of measuring spectra of electromagnetic radiation transmitted, scattered or reflected by the plasmonic crystal in visible, ultraviolet and/or infrared regions of the electromagnetic spectrum.

Detectors useful for SPR sensors capable of imaging also include two dimensional detectors capable of measuring a two dimensional spatial distribution of electromagnetic radiation transmitted, scattered or reflected by the plasmonic crystal. In the context of this description, the term "two dimensional spatial distribution of electromagnetic radiation" refers to measurement of intensities of electromagnetic radiation transmitted, scattered or reflected as a function of spatial position on the photonic crystal. Use of two dimensional detectors is useful for providing SPR sensors capable of two dimensional SPR imaging, for example to assess the spatial distribution of analytes in a sensing region proximate to a sensing surface of the crystal.

Exemplary detectors in SPR sensors include a photodioide, a photomultiplier tube, a spectrometer, a monochrometer, a diode array, a charged coupled device; a two-dimensional photodiode array, a digital camera, a complimentary metal oxide semiconductor (CMOS) detector, a plurality of photodiodes, a plurality of photomultiplier tubes or any combination of these.

A variety of optical sources are useful in SPR sensors and imaging systems of the present invention. Exemplary optical sources are capable of providing a beam of polarized incident electromagnetic radiation to the plasmonic crystal having wavelengths in ultraviolet, visible and/or infrared regions. The present SPR sensors also include tunable optical sources capable of providing a beam of incident electromagnetic radiation having a selectively adjustable (or tunable) wavelength distribution. Tunable optical sources are particularly beneficial for some SPR sensors of the present invention providing multiwavelength SPR scanning. Useful optical sources for SPR sensor of the present invention include, but are not limited to, pulsed optical sources, continuous optical sources, broad band sources, narrow band sources, lamps, lasers, and light emitting diodes. Optical sources of the present invention may further comprise a number of additional optical components, such as optical filters, optical fibers, monochrometers, Fabry-Perot filters, cut-off filters, polarization filters, neutral density filters, attenuation filters, band pass filters, prisms, diffraction gratings, reflectors or any combination of these.

In contrast to conventional SPR sensing systems, incident electromagnetic radiation useful in sensors and sensing methods of the present invention need not be polarized. In some embodiments, for example, the plasmonic crystal itself acts as a polarizer. The present invention includes, however, methods and systems wherein incident electromagnetic radiation directed on the plasmonic crystal is polarized. In some embodiments, incident electromagnetic radiation provided to the plasmonic crystal has a distribution of wavelengths in the ultraviolet, visible and/or infrared red regions of the electromagnetic spectrum, preferably for some embodiments visible or infrared regions. In some embodiments, incident electromagnetic radiation is directed onto the plasmonic crystal at normal incidence.

In another aspect, the present invention provides multispectral SPR sensing methods and SPR imaging methods using SPR sensors incorporating a two-dimensional, three dimensional or quasi-three dimensional plasmonic crystals. In one embodiment, the invention provides a method of sensing a change in an optical property of a probe region proximate to a sensing surface comprising the step of: (i) providing a plasmonic crystal comprising a substrate having an first surface with a plurality of features provided in a first array, the substrate comprising a dielectric material; and one or more films comprising an electrically conductive material, wherein at least a portion of the one or more films is supported by the first surface, and wherein at least a portion of the one or more of the films comprising the electrically conducting material is spatially aligned with each of the features of the first surface; wherein the spatial distribution, physical dimensions or both of the features of the first array are selected such that at least a portion of the electromagnetic radiation incident to the plasmonic crystal excites plasmonic responses in the one or more films comprising the electrically conducting material. The sensing method further comprises the step of: (ii) directing incident electromagnetic radiation onto the plasmonic crystal, thereby generating electromagnetic radiation transmitted, scattered or reflected by the plasmonic crystal. The sensing method further comprises the step of: (iii) measuring intensities of the electromagnetic radiation transmitted, scattered or reflected by the plasmonic crystal for a plurality of wavelengths. The sensing method further comprises the step of: (iv) providing an analyte proximate to the sensing surface, wherein the analyte changes the optical property of the probe region proximate to the sensing surface, thereby generating a change in the intensities of electromagnetic radiation transmitted, scattered or reflected by the plasmonic crystal. The sensing method further comprises the step of: (v) detecting the change the intensities of electromagnetic radiation transmitted, scattered or reflected by the plasmonic crystal at a plurality of wavelengths; thereby sensing the change in optical property proximate to the sensing surface. The present SPR sensing methods are highly versatile and provide a means for sensing, and characterizing a variety of optical properties of the probe region proximate to the sensing surface including refractive index, extinction coefficient, absorption coefficient and scattering coefficient.

In an embodiment, the invention provides a SPR multispectral sensing method wherein changes in the intensities of reflected, transmitted or scatter radiation are detected and/or measured to detect changes in or characterize the optical properties of a probe region proximate to a sensing surface of a SPR sensor. A method of the invention further comprises the steps of: (i) measuring a first set of the intensities of electromagnetic radiation transmitted, scattered or reflected by the plasmonic crystal for at least two wavelengths prior to the step of providing the analyte proximate to the sensing surface; (ii) measuring a second set of the intensities of electromagnetic radiation transmitted, scattered or reflected by the plasmonic crystal for the at least two wavelengths upon the step of providing the analyte proximate to the sensing surface; and (iii) comparing the first and second sets of intensities. In this embodiment differences in first and second sets of intensities indicates a change in optical property that are related to changes in composition, optical properties or physical state in the probe region.

In an embodiment, the invention provides a SPR multispectral sensing method further comprising the step of detecting a change in the wavelength of the of electromagnetic radiation transmitted, scattered or reflected by the plasmonic crystal having the largest intensity upon the step of providing the analyte proximate to the sensing surface. In this embodiment, detection of changes in the peak wavelength of reflected or transmitted electromagnetic radiation indicates changes in composition, optical properties or physical state in the probe region. Methods of the present invention include sensing steps wherein the change in peak wavelength reflected or transmitted electromagnetic radiation is measured and the absolute value of the measured change in peak wavelength is related to changes in composition in the probe region.

In an embodiment, the invention provides a SPR multi-spectral sensing method wherein spectra of transmitted or reflected electromagnetic radiation are measured prior to and upon exposure of the SPR sensor to analytes, such as a biomolecule, therapeutic candidates or other materials to be sensed. In one embodiment, the sensing method further comprising the steps of: (i) a measuring a first transmission or reflection spectrum of electromagnetic radiation transmitted or reflected by the plasmonic crystal prior to the step of providing the analyte proximate to the sensing surface; (ii) a measuring a second transmission or reflection spectrum of electromagnetic radiation transmitted or reflected by the plasmonic crystal upon the step of providing the analyte proximate to the sensing surface; and (iii) comparing the first transmission or reflection spectrum and the second transmission or reflection spectrum. In these methods measured changes in the spectra can be related to changes in composition or physical state in the probe region. Means of comparing spectra in these methods include, but are not limited to, (1) subtracting the first transmission or reflection spectrum from the second transmission or reflection spectrum, thereby generating a difference spectrum; (2) measuring shift(s) in a peak position(s) in the first transmission or reflection spectrum relative to the second transmission or reflection spectrum; and (3) comparing the intensities of transmitted or reflected electromagnetic radiation corresponding to a plurality of wavelengths or wavelength distributions.

The present invention also includes SPR sensing methods capable of generating SPR images or a probe region proximate to the sensing surface(s) of the SPR sensor. For example, the invention provides imaging methods for sensing changes in optical properties, such as refractive index, over a two dimensional area of the sensing surface further comprising the steps of measuring a two dimensional spatial distribution of electromagnetic radiation transmitted, scattered or reflected by the plasmonic crystal. In one embodiment, the imaging method comprises the steps: (i) measuring a first two dimensional spatial distribution of electromagnetic radiation transmitted, scattered or reflected by the plasmonic crystal prior to the step of providing the analyte proximate to the sensing surface; (ii) measuring a second two dimensional spatial distribution of electromagnetic radiation transmitted, scattered or reflected by the plasmonic crystal prior to the step of providing the analyte proximate to the sensing surface; and (iii) comparing the first two dimensional spatial distribution and the second two dimensional spatial distribution. Alternatively, the present invention includes methods wherein a two dimensional spatial distribution of electromagnetic radiation transmitted, scattered or reflected by the plasmonic crystal is measured and analyzed by comparing reference regions of the image to active regions wherein sensing is desired. These embodiments are attractive for many sensing applications because two dimensional sensing/imaging is achievable for each two dimensional spatial distribution of electromagnetic radiation collected and analyzed.

The present invention provides methods for making plasmonic crystals for SPR sensing using a combination of soft lithography patterning and thin film deposition technologies. Method of this aspect of the present invention provides a production platform for the low cost and high throughput fabrication of plasmonic crystals and SPR sensors. In one embodiment, a method of making a plasmonic crystal comprises the steps of: (i) providing a dielectric layer having a receiving surface; (ii) patterning an array of features on the receiving surface of the dielectric layer using a soft lithographic patterning technique, thereby generating the array features on the receiving surface of the dielectric layer; and (iii) depositing one or more films comprising electrically conducting material on at least a portion of the receiving surface of the dielectric layer having the array of features, thereby generating the plasmonic crystal. Soft lithography techniques useful for this aspect of the present invention include, but are not limited to, nanomolding, nanoimprinting, nanoembossing, nanotransfer printing, near phase-shifting photolithgrpahy, microcontact printing, replica molding, microtransfer molding, and solvent assisted micromolding. Soft lithographic techniques useful in the present invention are capable of generating high resolution arrays features having physical dimensions ranging from a few nanometers to 1000s of microns and are capable of patterning large areas of the dielectric layer. Deposition techniques useful in this aspect of the present invention, include, but are not limited to, chemical and physical thin film deposition techniques such as ion beam sputtering, plasma enhanced chemical thin film deposition, electron beam evaporation and thermal evaporation.

Useful electrically conducting films comprise metal films, semiconductor films or a combination of more metal films and semiconductor films. Deposition techniques useful in the present invention include deposition steps whereby one or more adhesion layers are provided to facilitate positioning and/or bonding of films of the electrically conducting material to a substrate, such as a nanostructured dielectric substrate. Use of adhesion layers and adhesion materials that do not significantly impact or degrade surface plasmon excitation in the layer of electrically conducting material are preferred in some embodiments. Non metal adhesion layers and materials, for example, are preferred in some embodiments. The present invention includes films and film structures of electrically conductive material comprising a conductor or semiconductor in combination with one or more nonmetal adhesion layers, such as tin oxide, barium oxide and organosilane, to facilitate binding to the dielectric substrate. The present invention includes methods wherein the deposition step generates a plurality of films have uniform thicknesses, and also comprises deposition steps capable of generating films having a selected non-uniform distribution of thicknesses. Electrically conducting films useful for some embodiments have thicknesses selected over the range of about 5 nanometers to about 5 microns. As discussed above, selection of film thicknesses is in part determined by whether transmitted or reflected electromagnetic radiation is detected.

In one embodiment, the present invention provides imprinting based methods of making plasmonic crystals using soft lithographic imprinting/molding methods and/or nanoimprinting/nanomolding methods. In one embodiment, a method of making a plasmonic crystal for SPR sensing comprises the steps of: (i) providing a template having an array of master features; (ii) imprinting the array of master features of the template onto a dielectric layer by contacting the template and the dielectric substrate, thereby generating an array of imprinted features on an imprinted surface of the dielectric layer; and (iii) depositing one or more electrically conducting films on at least a portion of the imprinted surface of the dielectric layer. Arrays of master features of templates useful in the present invention include periodic arrays of features, optionally including periodic arrays having one or more defects. In an embodiment, the first array of master features and the second array of imprinted features have a periodicity selected form the range of about 5 nanometers to about 5 microns.

In an embodiment of this aspect, the master features are an array of relief features, recessed features or both relief features and recessed features. In an embodiment, the master features of the first array and the imprinted features of the dielectric substrate have cross sectional areas selected from the range of about 25 nanometers$^2$ to 25 micron$^2$. In an embodiment, the master features of the first array and the imprinted features of the dielectric substrate have longitudinal dimensions (e.g., heights) selected from the range of about 5 nanometers to 5 micron. In some embodiments, the array of imprinted features have submicron cross sectional dimensions (length, width, radius, diameter etc.) and/or occupy an area of the imprinted surface of the dielectric layer selected over the range of about 500 nanometers$^2$ to about 1000 microns$^2$.

In a specific embodiment, the array of features of the imprinted surface of the dielectric substrate comprises a plurality of recessed features and/or relief features; wherein the step of depositing one or more electrically conducting films on at least a portion of the imprinted surface of the dielectric layer generates an a continuous film supported by the imprinted surface of the dielectric substrate, and optionally in conformal contact with imprinted surface of the dielectric substrate, that at least partially covers the features of the imprinted surface. In another embodiment, the step of depositing one or more electrically conducting films on at least a portion of the imprinted surface of the dielectric layer generates an electrically conducting film having an array apertures on a surface of the imprinted surface and a plurality of electrically conducting films on bottom surfaces or top surfaces of at least a portion of the recessed features or relief features, respectively.

In some embodiments, a master template having an array of relief features is used to imprint features comprising apertures that extend entirely through the thickness of the dielectric layer. In these embodiments, imprinting results in an array of apertures, optional a nanohole array, extending through a dielectric substrate layer.

In an embodiment the template having an array of master features comprises a polymeric stamp or mold, for example, a stamp or mold comprising poly(dimethylsiloxane). In an specific embodiment, a polymeric stamp or mold useful in the present methods comprises a composite stamp or mold having a first h-PDMS layer having the array of master features in contact with a second s-PDMS backing layer.

In a specific embodiment, the dielectric layer in the present method comprises a curable polymer or prepolymer layer. Useful curable polymers or prepolymers for this aspect of the present invention include, but are not limited to, polyurethane. An imprinting step in this embodiment comprises the steps of: (i) contacting the template with the curable polymer or prepolymer layer; (ii) curing the curable polymer or prepolymer layer in contact with the template, thereby generating a cured imprinted polymer layer; and (iii) separating the cured imprinted polymer layer and the template. In an embodiment providing a high throughput method for making plasmonic crystals and sensors the steps of: contacting the template with the curable polymer or prepolymer layer, curing the curable polymer or prepolymer layer in contact with the template; and separating the cured imprinted polymer layer and the template are repeatedly carried out to generate the array of features on the imprinted surface of the dielectric layer or on the imprinted surfaces of a plurality of dielectric layers. In an embodiment, the curing step comprises exposing the curable polymer or prepolymer layer in contact with the template to electromagnetic radiation or raising the temperature of the curable polymer or prepolymer layer in contact with the template.

Master features include relief features, recessed features or a combination both relief features and recessed features. Arrays of relief features include, but are not limited to arrays of cubes, columns, ribbons, posts and rectangular solids or any combination of these. Arrays of recessed features include, but are not limited to, depressions, channels, grooves, bores, openings, slits or any combination of these. In some embodiments, master features of the first array and the imprinted features of the dielectric substrate have cross sectional areas selected from the range of about 25 nanometers$^2$ to 25 micron$^2$ and vertical dimensions (e.g. height) selected from the range of about 5 nanometers to 5 micron. Use of master features having submicron cross section dimensions (e.g. lateral dimensions) is beneficial for some applications.

In an embodiment, the array of features of the imprinted surface of the dielectric substrate comprises a plurality of recessed features. In this fabrication process the step of depositing one or more electrically conducting films on at least a portion of the imprinted surface of the dielectric layer generates an electrically conducting film having an array apertures on a surface of the imprinted surface and a plurality of electrically conducting films on bottom surfaces of at least a portion of the recessed features. In another embodiment, the array of features of the imprinted surface of the dielectric substrate comprises a plurality of relief features. In this process the step of depositing one or more electrically conducting films on at least a portion of the imprinted surface of the dielectric layer generates a plurality of electrically conducting films on top surfaces of at least a portion of the relief features and an electrically conducting film having an array apertures on the imprinted surface of the dielectric substrate.

Templates useful for imprinting in these fabrication methods include polymeric stamps or molds, including stamps and molds comprising poly(dimethylsiloxane). In an exemplary embodiment, the template comprises a composite polymeric stamp or mold having a first h-PDMS layer having the array of master features in contact with a second s-PDMS backing layer. Templates in the present invention may comprise materials other than polymeric materials. In some embodiments, for example, methods of the present invention use a template comprising a patterned semiconductor wafer for fabricating plasmonic crystals.

BRIEF DESCRIPTION OF THE DRAWINGS

FIGS. 1A-1P provide schematic diagrams illustrating a variety of three-dimensional plasmonic crystal geometries of the present invention comprising multilayer thin film structures. FIGS. 1Q and 1R provide schematic diagrams of SPR sensors employing three dimensional plasmonic crystals of the present invention. FIG. 1T shows atomic force micrographs (SEM) of multilayer plasmonic crystals of the present invention.

As shown in FIG. 21, the spectra is observed to shift to higher wavelengths for plasmonic crystals having larger periods.

As shown in FIG. 22 the depth of the holes increases systematically as the stamp is reused sequentially.

As shown in FIG. 23 the diameter of the holes increases systematically as the stamp is reused sequentially.

DETAILED DESCRIPTION OF THE INVENTION

Figure 1:
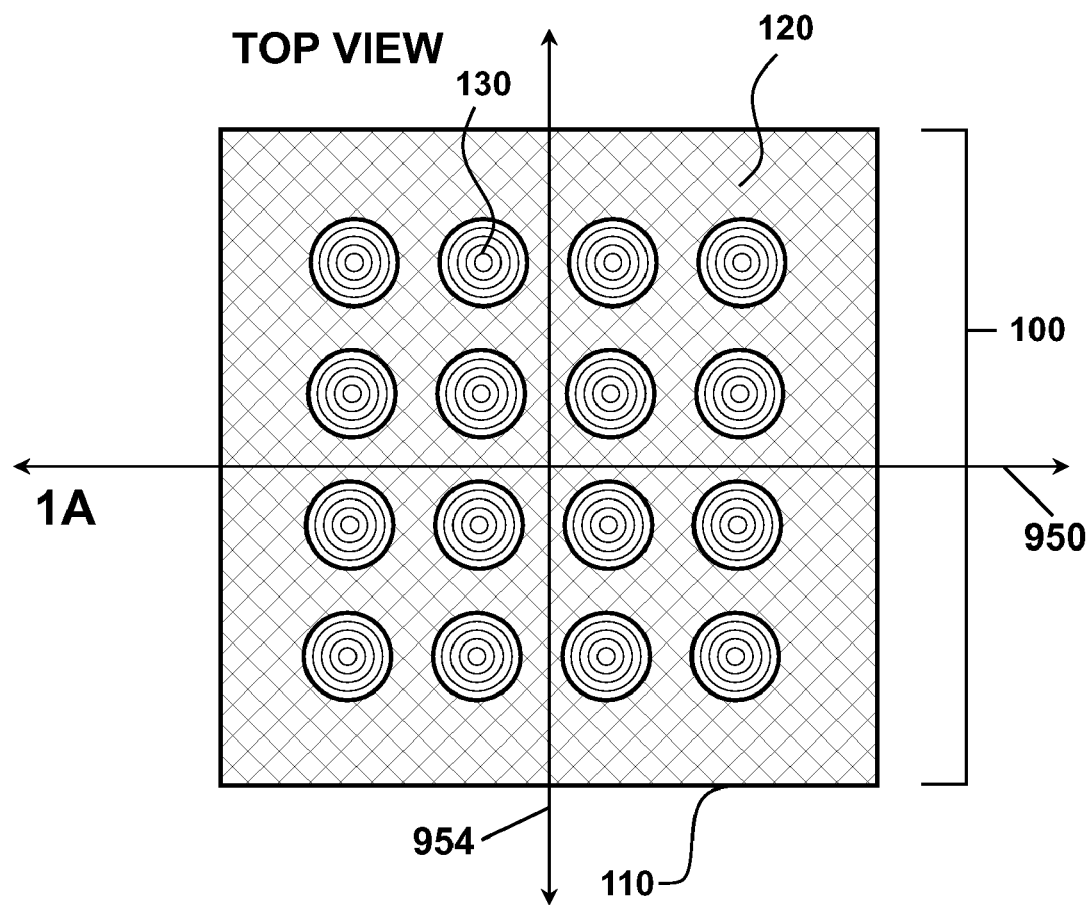
FIG. 1.
Figure 1:
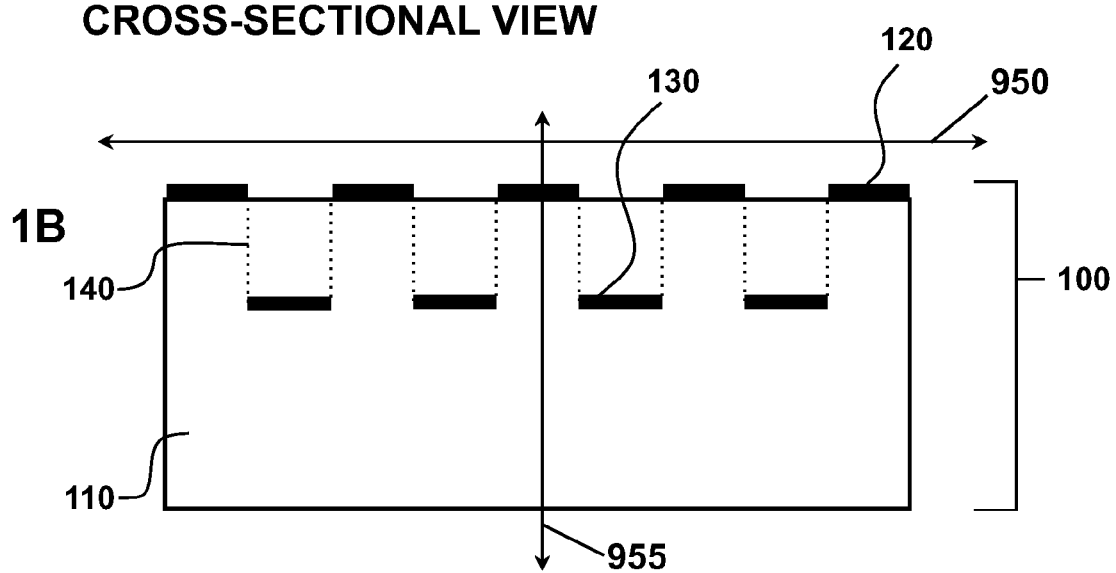
Figure 1:
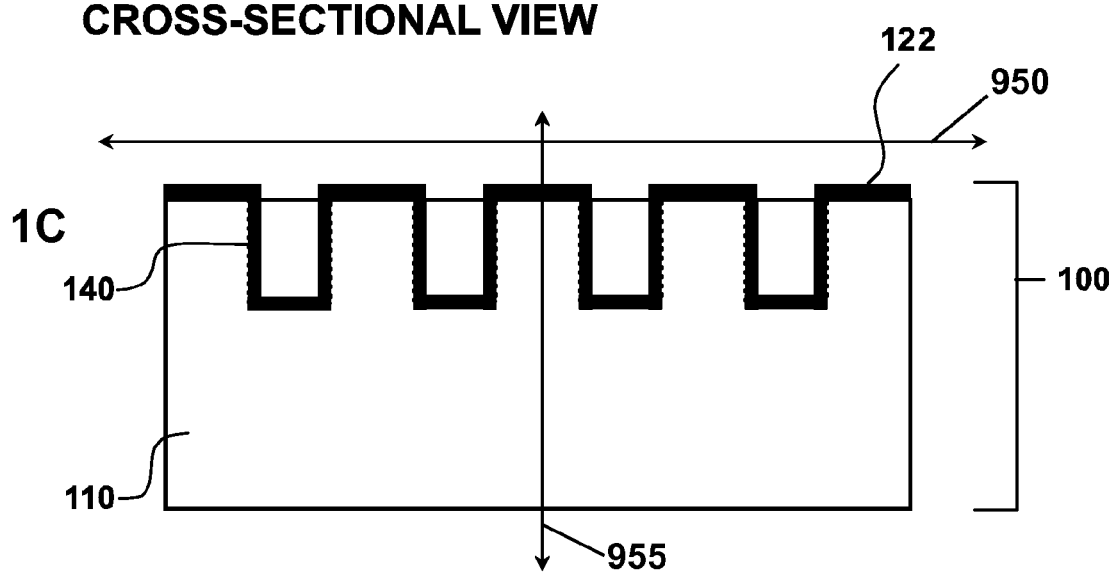
Figure 1:
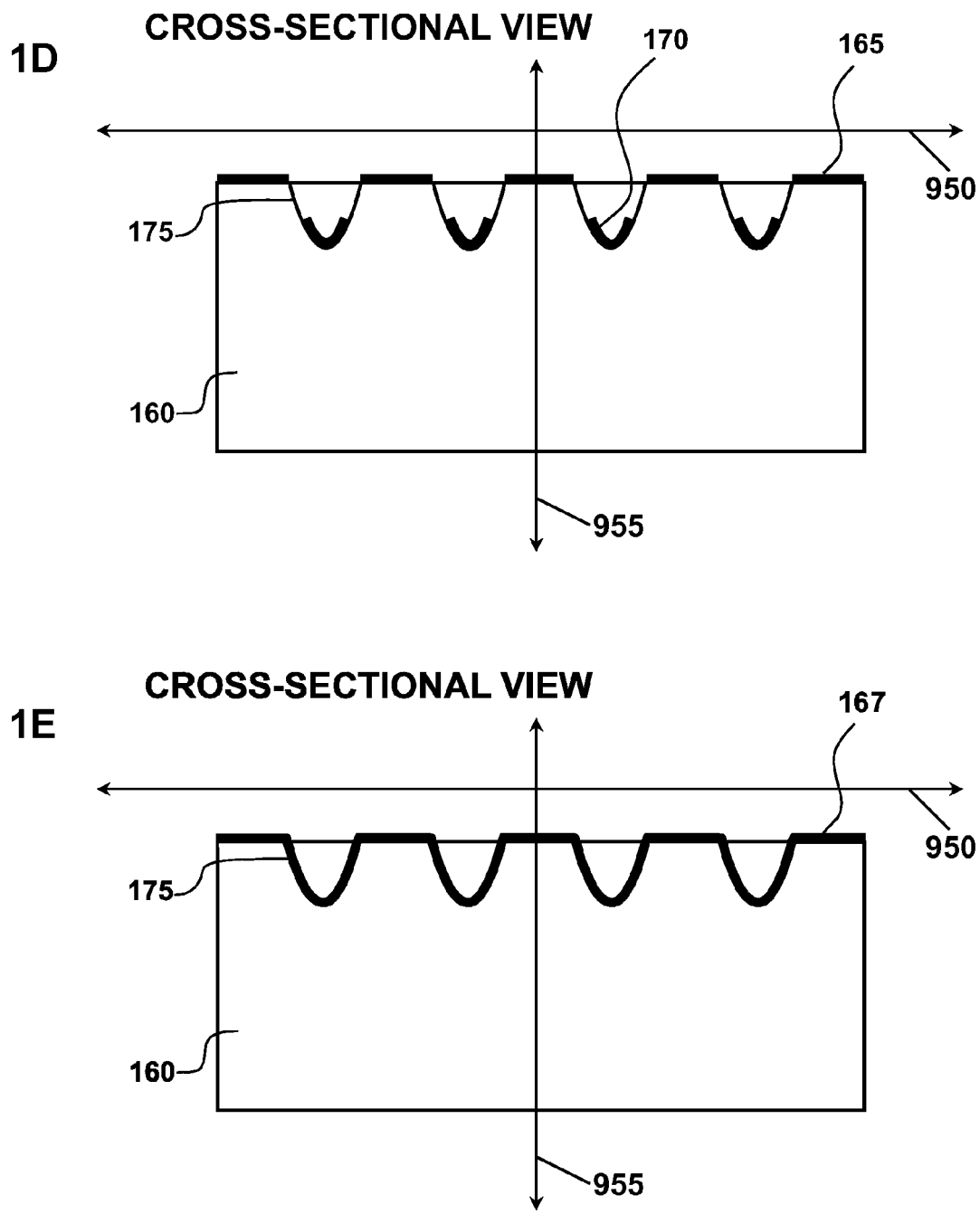
Figure 1:
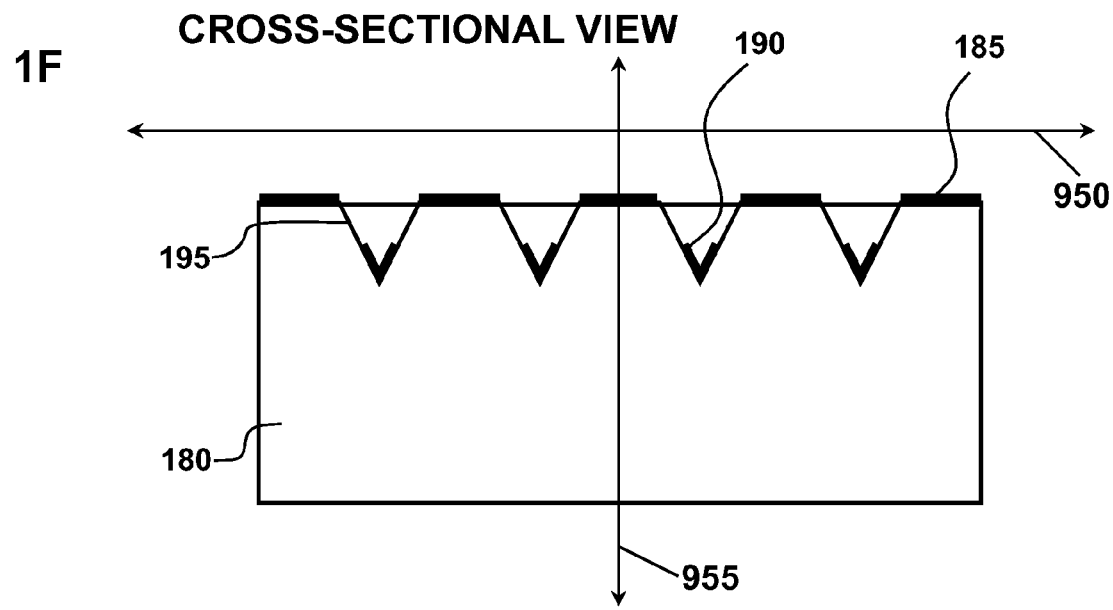
Figure 1:
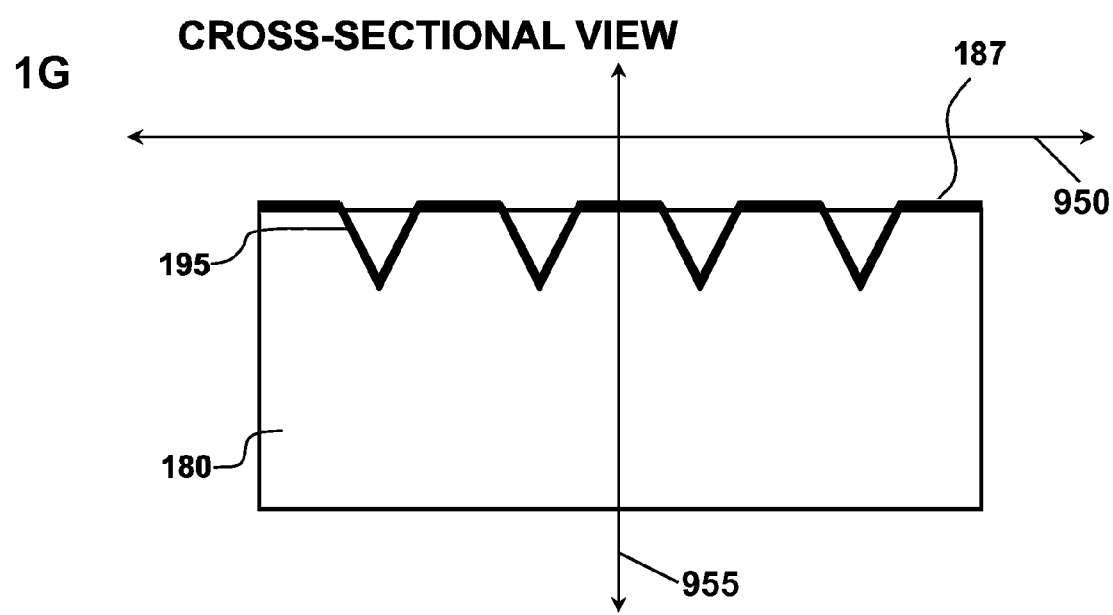
Figure 1:
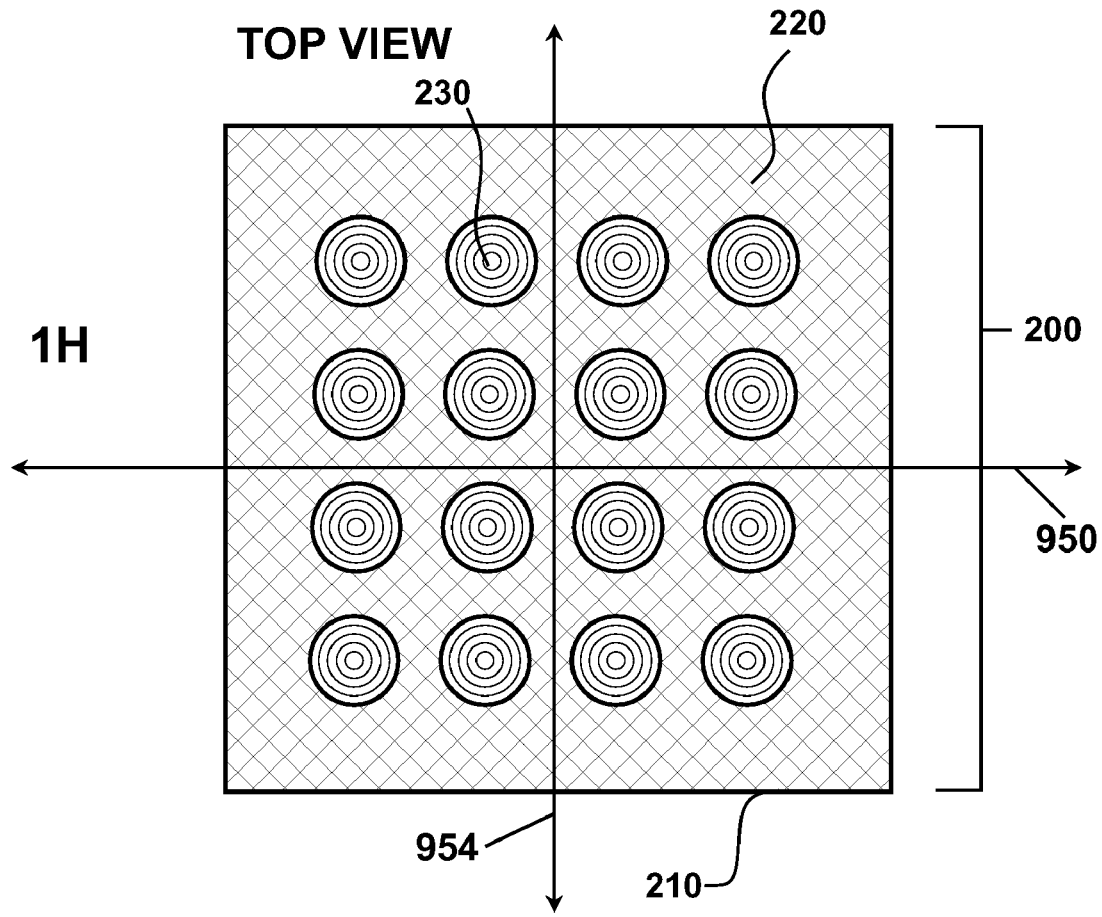
Figure 1:
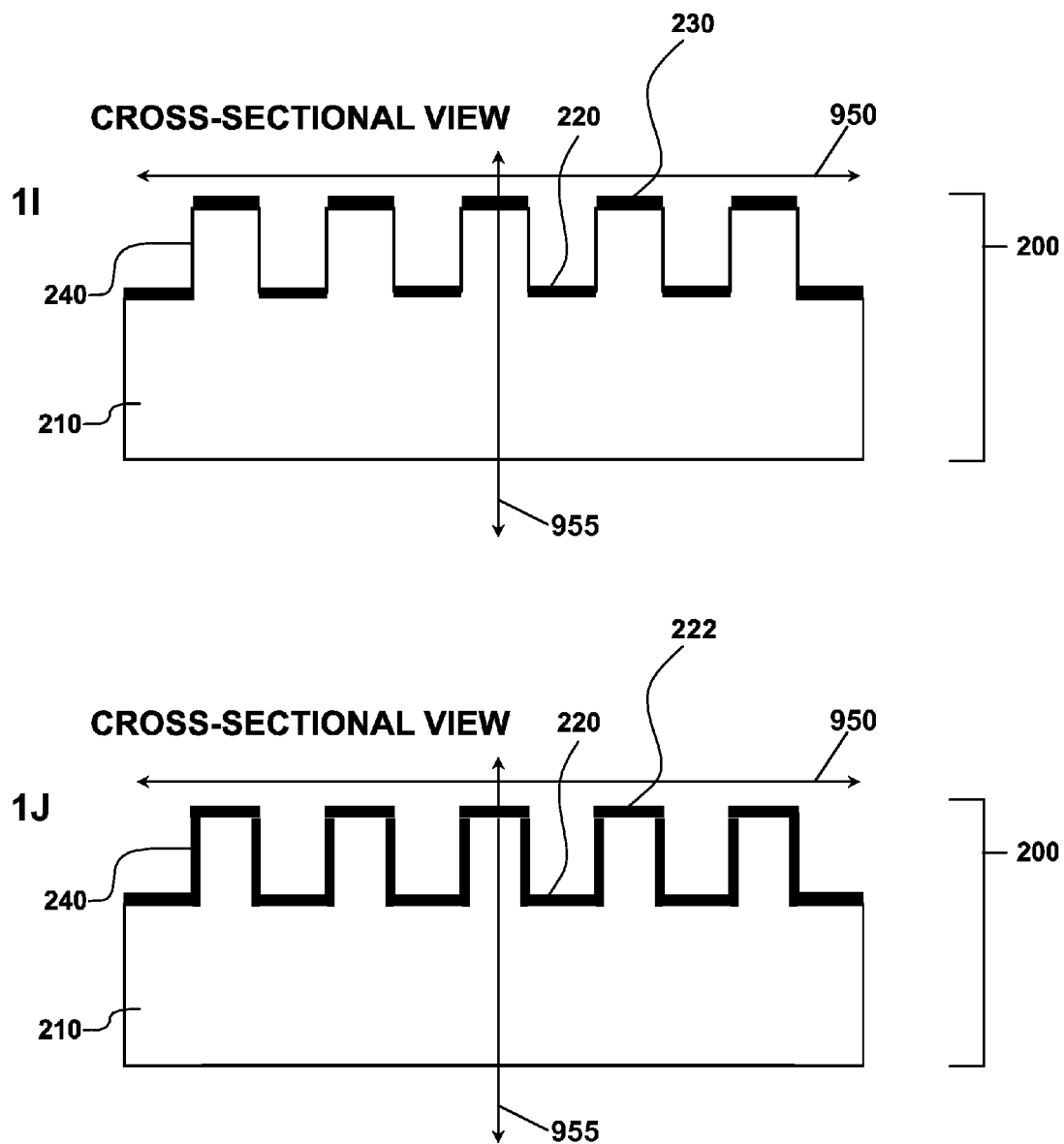
Figure 1:
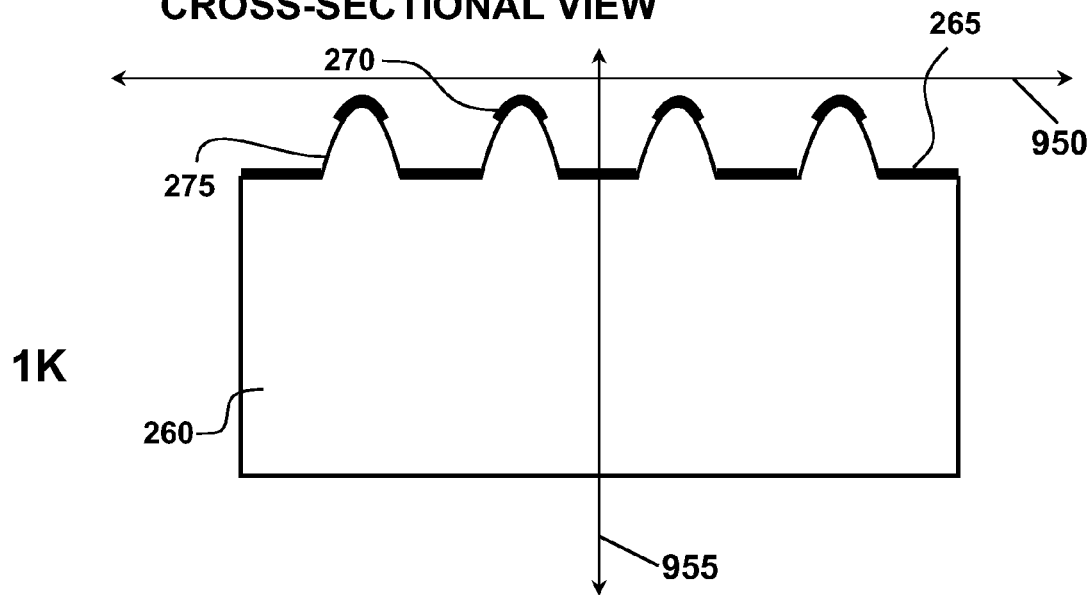
Figure 1:
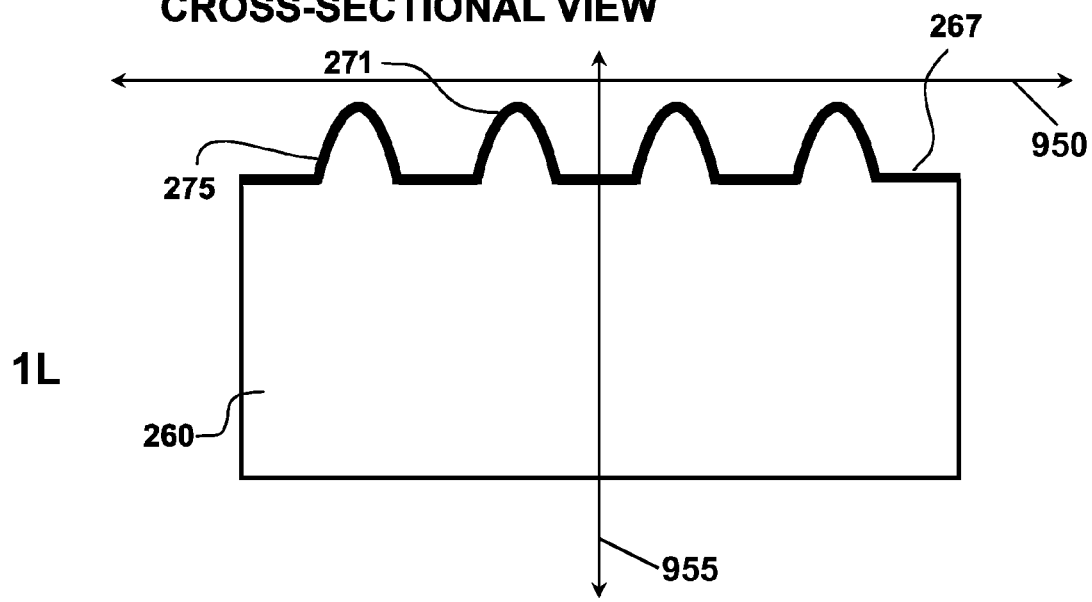
Figure 1:
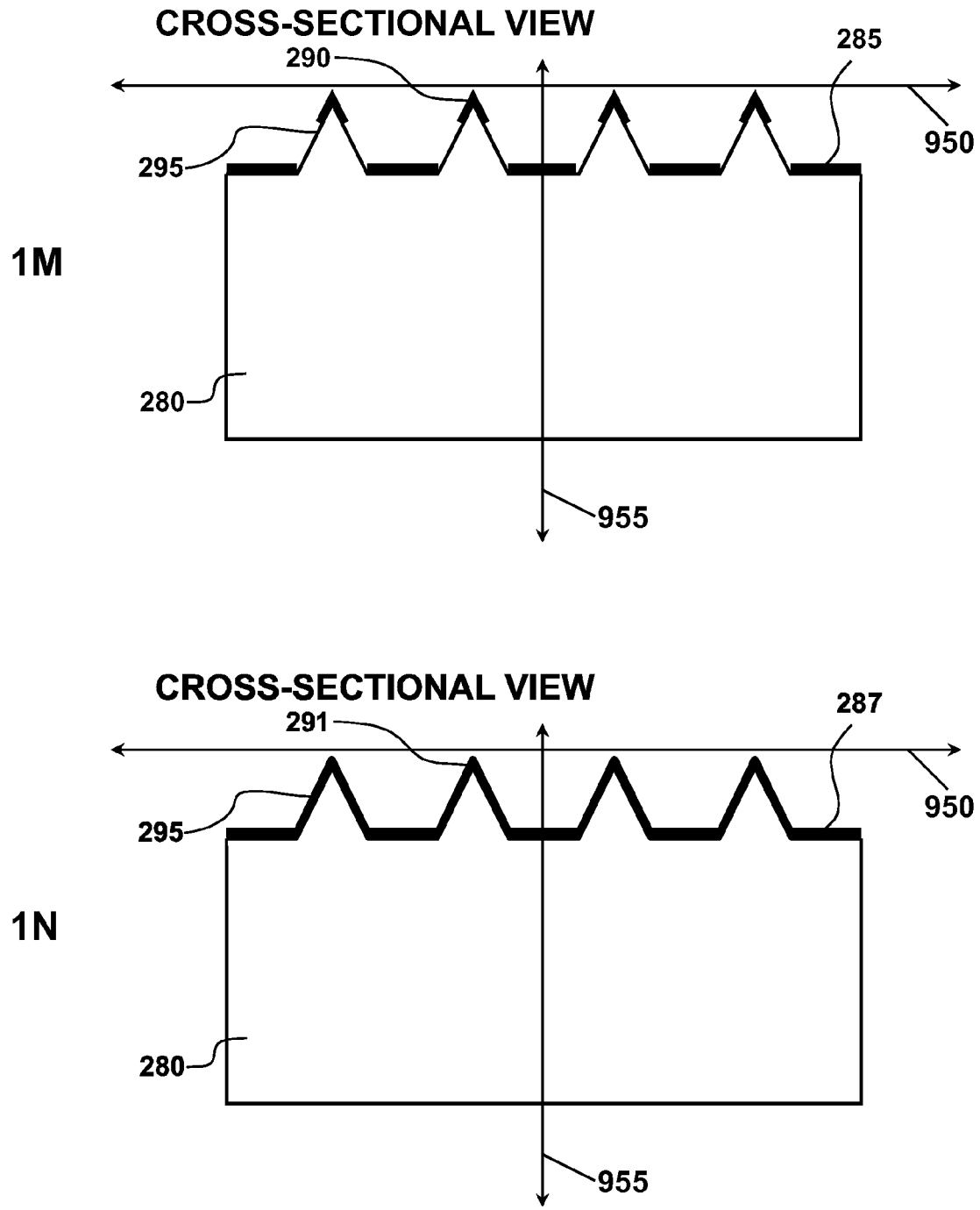
Figure 1:
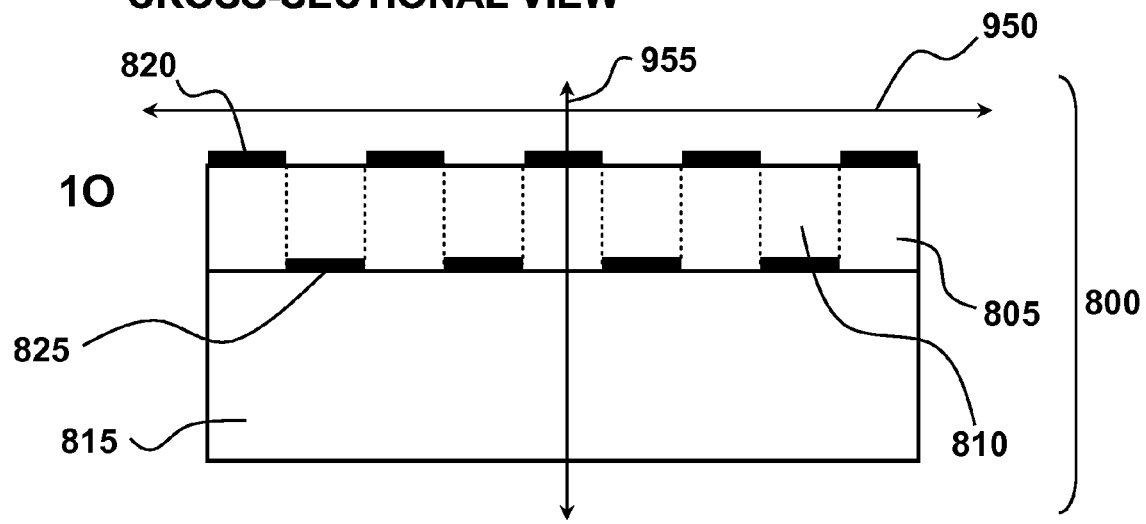
Figure 1:
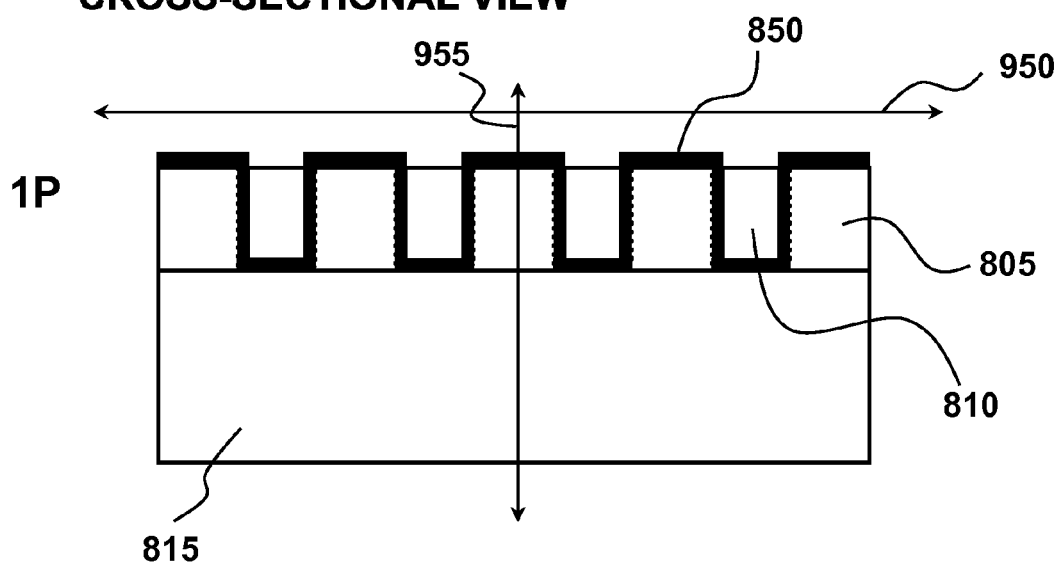
Figure 1:
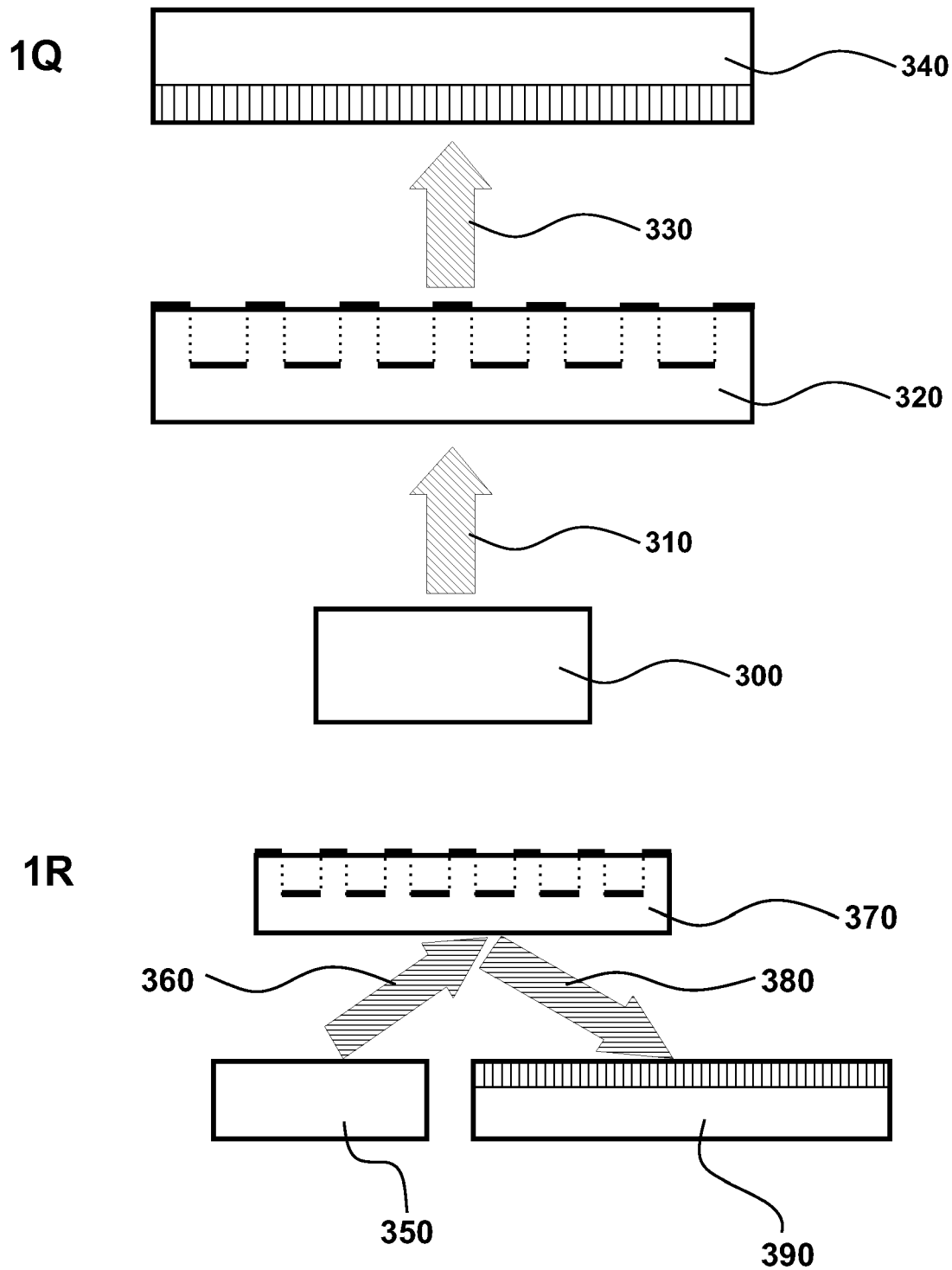

The terms "electromagnetic radiation" and "light" are used synonymously in the present application and refer to waves of electric and magnetic fields. Electromagnetic radiation useful for the methods of the present invention includes, but is not limited to, infrared light, ultraviolet light, visible light or any combination of these.

"Beam of light", "light beam", "electromagnetic radiation beam" and "beam of electromagnetic radiation" are used synonymously and refer to electromagnetic radiation propagating in the same direction. In the present description, use of the term beam of light is intended to be consistent with use of this term in the art of optics and spectroscopy. Beams of light useful in the methods of the present invention included coherent beams of light, pulses of light and coherent pulses of light. Beams of light useful in some applications comprise photons having substantially parallel propagation axes. In this context the term "parallel" refers to a geometry in which two axes are equidistant from each other at all points and the term "substantially parallel" is intended to refer to a geometry including some deviations from absolute parallelism. Beams of light useful in the present methods may be focusing, diverging, collimated, semicollimated or noncollimated.

"Molecule" refers to a collection of chemically bound atoms with a characteristic composition. As used herein, a molecule can be neutral or can be electrically charged. The term molecule includes biomolecules, which are molecules that are produced by an organism or are important to a living organism, including, but not limited to, proteins, peptides, lipids, DNA molecules, RNA molecules, oligonucleotides, carbohydrates, polysaccharides; glycoproteins, lipoproteins, sugars and derivatives, variants and complexes of these, including labeled analogs of these. The term molecule also includes candidate molecules, which comprise any molecule that it is useful, beneficial or desirable to probe its capable to interact with a molecule such as a target molecule. Candidate molecules include therapeutic candidate molecules which are molecules that may have some effect on a biological process or series of biological processes when administered. Therapeutic candidate molecules include, but are not limited to, drugs, pharmaceuticals, potential drug candidates and metabolites of drugs, biological therapeutics, potential biological therapeutic candidates and metabolites of biological therapeutics, organic, inorganic and/or hybrid organic-inorganic molecules that interact with one or more biomolecules, molecules that inhibit, decrease or increase the bioactivity of a biomolecule, inhibitors, ligands and derivatives, variants and complexes of these, including labeled analogs of these.

"Supported by a surface" and "supported by a substrate" refers to a structure, such as a film of electrically conducting material, that is present at least partially on a substrate/surface or present at least partially on one or more intermediate structures positioned between the structure and the substrate/surface. The term "supported by a substrate" may also refer to structures partially or fully embedded in or raised on a substrate.

"Conformal contact" refers to contact established between a device component, such as a film, and a surface, such as the surface of a dielectric substrate, useful for plasmonic crystals and plasmonic crystal sensors of the present invention. In one aspect, conformal contact involves a macroscopic adaptation of one or more films, including but not limited to a continuous film or plurality of discrete films, and a substrate surface such as the surface of a nanostructured substrate. In another aspect, conformal contact involves a microscopic adaptation of one or more films, including but not limited to a continuous film or plurality of discrete films, and a substrate surface, such as the surface of a nanostructured substrate, leading to an intimate contact with out voids. In some embodiments, for example, plasmonic crystals and plasmonic crystal sensors of the present invention comprise one or more films, including but not limited to a continuous film and/or a plurality of thin film(s), provided in conformal contact with a surface of a dielectric substrate having a plurality of features, such as recessed and/or relief features.

"Electrically conducting" refers to the characteristic of a material to conduct electric charge. Examples of electrically conducting materials include metals, inorganic and organic semiconductors, and conducting polymers.

In some embodiments, features of the first array, and optionally the films of the second array, are nanosized and/or nanostructured. In the context of the present description, the term "nanosized" refers to features or films having at least one physical dimension, such as a cross sectional dimension or longitudinal dimension (e.g., width, thickness, height, length, diameter), that is less than about one micron. In the context of the present description, the term "nanostructured" refers to a film, layer, surface or substrate having one or more nanosized features, including an array of nanosized features, and optionally a periodic array of nanosized features.

"Film" refers to one or more layers of one or more materials, such as an electrically conducting material. As used herein the term film may refer to a layer of material, such as an electrically conducting material, that is provided to one or more surfaces of a plasmonic crystal using a deposition method, including but not limited to, physical vapor deposition, chemical vapor deposition, ion beam sputtering deposition, plasma enhanced chemical thin film deposition, electron beam evaporation deposition, atomic layer deposition, and thermal evaporation deposition. The term film includes one or more thin films, for example films having a thickness dimension selected from the range of 5 nanometers to 5 microns. Electrically conducting films of the present invention include metal and semiconductor films (inorganic or organic), and optionally include one or more additional layers such as adhesion layers to facilitate bonding of the film(s) to the surfaces of dielectric substrates, including nanostructured dielectric substrates.

"Spatially aligned" refers to the position of films with respect to features provided in a substrate of a photonic crystal of the present invention. Spatially aligned films are provided such that they have preselected positions relative to features of the substrate. In an embodiment, spatially aligned films are provided such that they line up with components of the features in the substrate, such as top surfaces of relief features, bottom surfaces of recessed features and apertures extending through a substrate. An example of a spatially aligned film is a film that is positioned on the top surface of a relief feature. Another example of a spatially aligned film is a film that is positioned on the bottom surface of a recessed feature. Another example of a spatially aligned film is a film that is positioned on an area that is exposed by an aperture extending through a substrate.

As used herein, the term "array" refers to an ordered arrangement of structural elements, such as an ordered arrangement of individually addressed and spatially localized elements. Arrays useful in the present invention include arrays of recessed features, relief features and/or apertures useful for fabricating, positioning and/or supporting film elements of a photonic crystal.

The present invention provides plasmonic crystals comprising three-dimensional and quasi-three dimensional distributions of metallic or semiconducting films, including layered nanostructured and/or nanosized films and film arrays, that enable an advanced sensing platform for chemical and biological sensing. Sensors, sensing methods and sensing systems provide enhanced sensitivities relative to conventional SPR based sensors and are compatible with direct, low cost integration into a range of delivery and high throughput screening systems, including microfluidic, nanofluidic and microarray systems. The present invention also provides methods for fabricating plasmonic crystals via soft lithography patterning and thin film deposition techniques.

FIGS. 1A-1P provide schematic diagrams illustrating a variety of three-dimensional plasmonic crystal geometries of the present invention comprising multilayer thin film structures and continuous thin film structures. FIGS. 1Q and 1R provide schematic diagrams of SPR sensors employing three dimensional or quasi-three dimensional plasmonic crystals of the present invention.

FIGS. 1A (top view) and 1B (cross sectional view) illustrate a three-dimensional plasmonic crystal 100 having a recessed feature multilayer design. Plasmonic crystal 100 comprises a first metallic film 120 and periodic array of metallic films 130, all of which are supported by dielectric substrate 110. Dielectric substrate 110 has a periodic array of recessed features 140, each having a rectangular shape. As shown in FIGS. 1A and 1B, periodic array of recessed features 140 of dielectric substrate 110 is periodic with respect to lateral axes 954 and 950. Recessed features 140 extend along axes parallel to vertical axis 955. As shown in the figures, metallic film 120 has an periodic array of apertures that are spatially aligned with the positions of recessed features 140 of dielectric substrate 110.

FIGS. 1A and 1B illustrate the multilevel geometry of plasmonic crystal 100 provided by the recessed features of dielectric substrate 110. Metallic film 120 is provided in a first layer and metallic films 130 are provided in a second layer physical displaced from the first layer along vertical axis 955. As illustrated in FIGS. 1A and 1B, an external surface of dielectric substrate 110 supports metallic film 120 and the bottom surfaces of recessed features 140 of support metallic films 130. This layered plasmonic crystal geometry provides metallic films 130 in positions such that they are precisely aligned with the apertures extending through metallic film 120. In a useful embodiment, metallic film 120 is a nanostructure film and has apertures with submicron sized cross sectional dimensions. In a useful embodiment, metallic films 130 are nanosized films having submicron sized cross sectional dimensions and are provide in a periodic array.

FIG. 1C provides a cross sectional view of an alternative plasmonic crystal configuration having continuous metal film 122 supported by the dielectric substrate 110. In this configuration, continuous metal film 122 covers the external surface of dielectric substrate 110 including covering recessed features 140. As shown in FIG. 1C, continuous metal film 122 covers the side surfaces and bottom surfaces of recessed features 140. Optionally, continuous metal film 122 is provided such that it physical contacts, and optionally conformally covers, the external surface of dielectric substrate 110 including conformally covering recessed features 140.

FIGS. 1D and 1F provide cross sectional views of an alternative multilayer plasmonic crystal geometries wherein recessed features 175 and 195 of dielectric substrates 160 and 180, respectively, have dimpled and triangular shapes, respectively. In these schematic diagrams, metallic films having the periodic array of apertures are designated by drawing elements 165 and 185, and the periodic array of metallic films supported by bottom surfaces of the recessed features are designated by drawing elements 170 and 190.

FIGS. 1E and 1G provides a cross sectional views of alternative plasmonic crystal configurations having continuous metal films 167 and 187 supported by dielectric substrates 160 and 180. In this configuration, continuous metal films 167 and 187 cover the external surfaces of dielectric substrates 160 and 180 including covering recessed features 175 and 195, respectively. As shown in FIGS. 1E and 1G, continuous metal films 167 and 187 cover the side surfaces and bottom surfaces of recessed features 175 and 195, respectively. Optionally, continuous metal films 167 and 187 physical contact, and optionally conformally cover, the external surfaces of dielectric substrates 160 and 180 including conformally covering recessed features 175 and 195.

FIG. 1H (top view) and 1I (cross sectional view) illustrate a three-dimensional plasmonic crystal 200 having a relief feature multilayer design. Plasmonic crystal 200 comprises a first metallic film 220 and periodic array of metallic films 230, all of which are supported by dielectric substrate 210. Dielectric substrate 210 has an periodic array of relief features 240, each having a rectangular shape (i.e. columns). As shown in FIGS. 1H and 1I, periodic array of relief features 240 of dielectric substrate 210 is periodic with respect to lateral axes 954 and 950. Relief features 240 extend along axes parallel to vertical axis 955. As shown in the figures, metallic film 220 has a periodic array of apertures that are spatially aligned with the positions of relief features 240 of dielectric substrate 210.

FIGS. 1H and 1I illustrate the multilevel geometry of plasmonic crystal 100 provided by the relief features of dielectric substrate 210 Metallic film 220 is provided in a first layer and metallic films 230 are provided in on top of the relief features in a second layer physical displaced from the first film along vertical axis 955. As illustrated in FIGS. 1H and 1I, an external surface of dielectric substrate 210 supports metallic film 220 and the top surfaces of relief features 240 of support metallic films 230. This layered plasmonic crystal geometry provides metallic films 230 in positions such they are precisely spatially aligned with the apertures extending through metallic film 220. In a useful embodiment, metallic film 220 is a nanostructure film and has apertures with submicron sized cross sectional dimensions. In a useful embodiment, metallic films 230 are nanosized films having submicron sized cross sectional dimensions and are provide in a periodic array.

FIG. 1J provides a cross sectional view of an alternative plasmonic crystal configuration having continuous metal film 222 supported by the dielectric substrate 210. In this configuration, continuous metal film 222 covers the external surface of dielectric substrate 210 including covering relief features 240. As shown in FIG. 1J, continuous metal film 222 covers the side surfaces and top surfaces of relief features 240. Optionally, continuous metal film 222 is provided such that it physical contacts, an optionally conformally covers, the external surface of dielectric substrate 210 including conformally covering relief features 240.

FIGS. 1K and 1M provide cross sectional views of alternative multilayer plasmonic crystal geometries wherein relief features 275 and 295 of dielectric substrates 260 and 280, respectively, have buldged and triangular shapes, respectively. In these schematic diagrams, metallic films having the periodic array of apertures are designated by drawing elements 265 and 285, and the periodic array of metallic films supported by top surfaces of the relief features are designated by drawing elements 270 and 290.

FIGS. 1L and 1N provides a cross sectional views of alternative plasmonic crystal configurations having continuous metal films 271 and 291 supported by dielectric substrates 260 and 280, respectively. In this configuration, continuous metal films 271 and 291 cover the external surfaces of dielectric substrates 260 and 280 including covering relief features 275 and 295, respectively. As shown in FIGS. 1L and 1N, continuous metal films 271 and 291 cover the side surfaces and bottom surfaces of relief features 275 and 295, respectively. Optionally, continuous metal films 271 and 291 are provided such that they physical contact, an optionally conformally covers, the external surfaces of dielectric substrates 260 and 280, including conformally covering relief features 275 and 295.

FIG. 1O provides a cross sectional view of a multilayer plasmonic crystal 800 comprising a first dielectric substrate 805 having an array of features comprising apertures 810 extending entirely thorough first dielectric substrate 805. Multilayer plasmonic crystal 800 further comprises second dielectric substrate 815 provided in contact with first dielectric substrate 805. As shown in FIG. 1O, apertures 810 of first dielectric substrate 805 expose exposed areas of second dielectric substrate 815. A first film 820 is provided on the external surface of the first dielectric substrate 805 having an array of features. A plurality of films 825 is provided in a second array, wherein films 825 of the second array are provided on the exposed areas of second dielectric substrate 815. FIG. 1O illustrate a multilayer plasmonic crystal configuration of the present invention provided using a first dielectric layer having an array of apertures and a second dielectric substrate provided in contact with the first dielectric substrate.

FIG. 1P provides a cross sectional view of an alternative plasmonic crystal configuration having continuous metal film 850 supported by first and second dielectric substrates 805 and 815. In this configuration, continuous metal film 850 covers the external surface of first dielectric substrate 805, including covering the side surfaces of apertures 810, and also cover the exposed areas of second dielectric substrate 815. As shown in FIG. 1O, continuous metal film 850 covers the side surfaces of apertures 810 along the entire thickness of first dielectric substrate 805. Optionally, continuous metal film 850 is provided such that it physical contacts, an optionally conformally covers, the external surface of first dielectric substrate 805, including conformally covering the side surfaces of apertures 810, and conformally covers exposed areas of second dielectric substrate 815.

FIG. 1Q shows a SPR sensor of the present invention provided in transmission mode. SPR sensor comprises optical source 300, three dimensional multilayered plasmonic crystal 320 and photodetector 340. In this embodiment, optical source 300 generates electromagnetic radiation 310 that is directed on plasmonic crystal 320. The electromagnetic radiation 310 generates coupled plasmonic responses in metallic films of first and second layers of plasmonic crystal 320. Electromagnetic radiation 330 transmitted by plasmonic crystal 320 is detected by detector 340. In some embodiments, detector 340 is a multispectral detector capable of measuring the spectra of electromagnetic radiation transmitted by plasmonic crystal 320. In some embodiments, detector 340 is a two dimensional detector capable of imaging sensor surface areas. By monitoring changes in the intensities and/or spatial distributions of electromagnetic radiation transmitted by plasmonic crystal 320 at a plurality of wavelengths changes in the refractive index proximate to a sensing surface of plasmonic crystal 320 may be accurately detected, characterized and/or imaged. As will be understood by those skilled in the art the optical geometry shown in 1Q is equally applicable to plasmonic crystal sensors having a plasmonic crystal with a continuous film provided on the surface of a dielectric substrate, as opposed to a multilayer geometry.

FIG. 1R shows a SPR sensor of the present invention provided in reflection mode. SPR sensor comprises optical source 350, three dimensional multilayered plasmonic crystal 370 and photodetector 390. In this embodiment, optical source 350 generates electromagnetic radiation 360 that is directed on plasmonic crystal 320. The electromagnetic radiation 360 generates coupled plasmonic responses in metallic films of first and second layers of plasmonic crystal 370. Electromagnetic radiation 380 reflected by plasmonic crystal 370 is detected by detector 390. In some embodiments, detector 390 is a multispectral detector capable of measuring the spectra of electromagnetic radiation reflected by plasmonic crystal 370. In some embodiments, detector 390 is a two dimensional detector capable of imaging sensor surface areas. By monitoring changes in the intensities and/or spatial distributions of electromagnetic radiation reflected by plasmonic crystal 370 at a plurality of wavelengths changes in the refractive index proximate to a sensing surface of plasmonic crystal 370 may be accurately detected, characterized and/or imaged. As will be understood by those skilled in the art the optical geometry shown in 1R is equally applicable to plasmonic crystal sensors having a plasmonic crystal with a continuous film provided on the surface of a dielectric substrate, as opposed to a multilayer geometry.

Figure 1S:
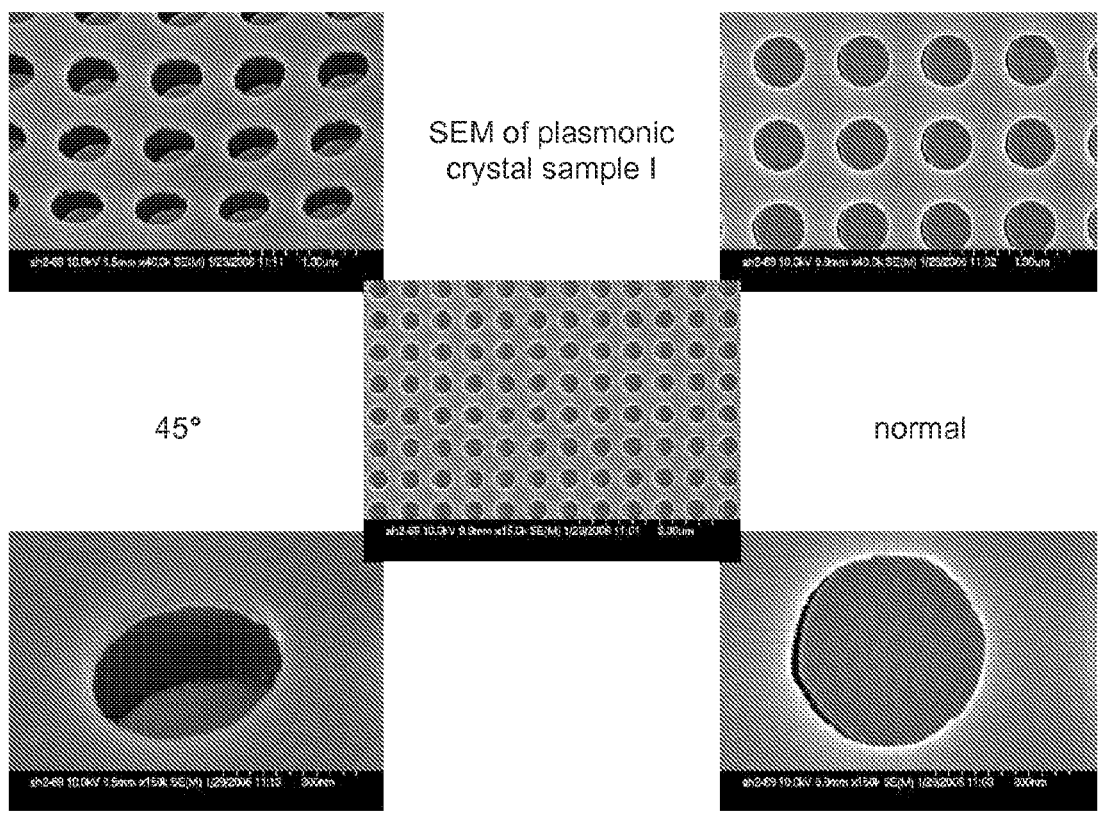
FIG. 1S shows scanning electron micrographs (SEM) of multilayer plasmonic crystals of the present invention.

FIG. 1S shows scanning electron micrographs (SEM) of multilayer plasmonic crystals of the present invention. FIG. 1T shows atomic force micrographs (SEM) of multilayer plasmonic crystals of the present invention.

Figure 2A:
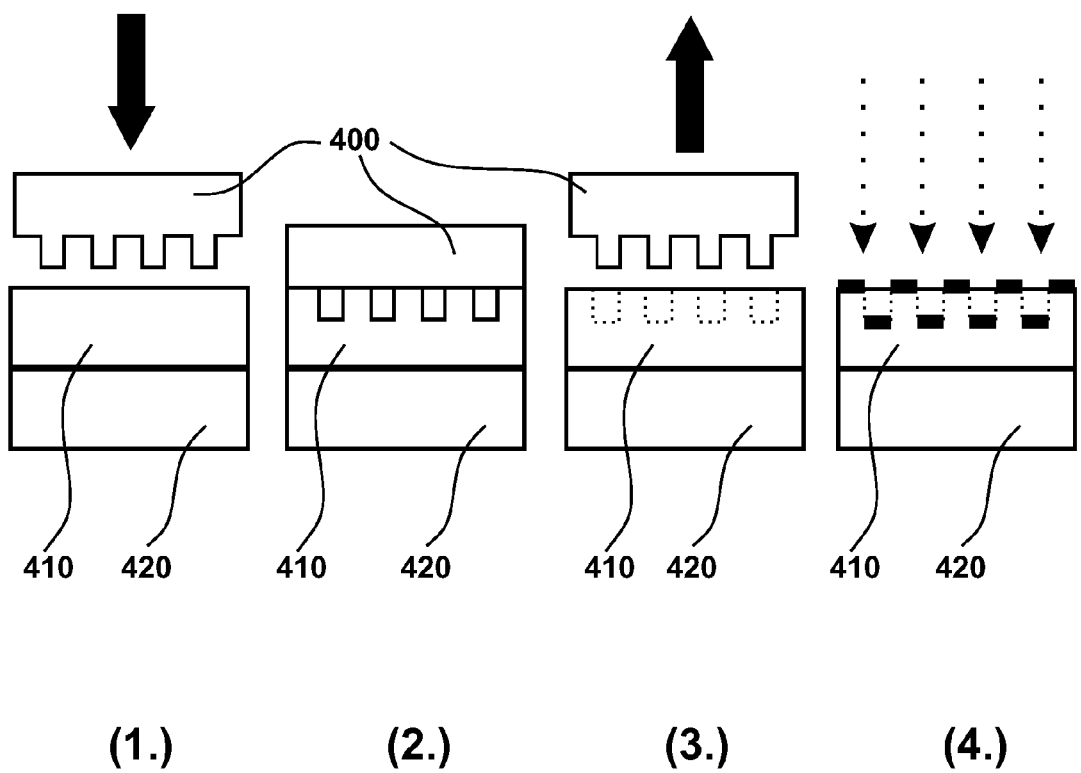
FIG. 2 provides a schematic diagram illustrating a method of fabricating plasmonic crystals using a combination of imprint lithography and thin film deposition techniques.

FIG. 2 provides a schematic diagram illustrating a method of fabricating plasmonic crystals using a combination imprint lithography and thin film deposition techniques. As shown in panel 1, a curable layer 410 is provided on substrate 420, for example via spin coating. Template 400 having a periodic array of master relief features is provided and brought into contact with curable layer 410, thereby imprinting a surface of curable layer 410 (see panel 2). While in contact with Template 400, curable layer is cured, thereby generating an array of imprinted features on an imprinted surface of the now cured layer. As shown panel 3, template 400 and curable layer 410 are subsequently separated from each other thereby exposing the imprinted features of the cured layer. As shown in panel 4, a plurality of thin metal films are deposited on the imprinted features of the imprinted surface of the cured layer, thereby generating the multilayered plasmonic crystal. In panel 4, the metal deposition processing step is schematically illustrated by dotted arrows.

Example 1

High Performance Plasmonic Crystal Sensor Formed by Soft Nanoimprint Lithography Abstract This Example describes a new type of plasmonic sensor fabricated by imprint lithography using a soft, elastomeric mold. Angle-dependent, zero-order transmission experiments demonstrate the sensing potential of this device, which uses a two dimensional plasmonic crystal. Full angle-dependent mapping shows that the sensitivity to surface chemical binding events reaches maxima near regions of the plasmonic Brillouin zone where the dispersion curves of multiple surface plasmon polariton modes converge. This behavior, together with the simple, low cost procedures for building the structures, demonstrates an important role for these devices in high performance chemical and biological sensing.

Introduction

The field of biosensing exploits many technologies that are optically based. While heavily dominated by spectroscopic protocols that employ fluorescence, label-less methods that exploit the surface plasmon polariton (SPP) resonances of uniform metal films such as gold or silver have become increasingly important. In such systems, the spectral position and the quality of resonance are completely defined by the intrinsic properties of the metal used, the thickness and refractive index of the analyte film, and the prism used to couple light into and out of the SPP. These device features make it impossible to improve their performance by, for example, moving the SPP resonance to an absorption band of a molecule to be detected—some limited change in resonance position can be induced by changing the material, and therefore the index, of the coupling prism. One strategy for eliminating this restriction is to replace the prism-flat metal film combination with a metal grating. In this case, the geometry of the grating can be used to control the position of the SPP resonance and further provide capacities needed to develop new types of compact form factor sensors. The required submicron features needed to couple SPPs with light at visible wavelengths are difficult, and expensive, to fabricate using conventional means. Low cost lithographic procedures based on printing and molding have the capabilities to fabricate high quality metal structures with the necessary dimensions needed to couple to the SPPs. This Example describes the use of a nanoimprinting technique that uses soft elastomeric molds and photo-curable polymers to form high resolution two dimensional plasmonic crystal sensors. Angle-dependent, zero-order transmission experiments using a model system consisting of an alkanethiolate self-assembled monolayer (SAM) on Au, reveal sensitivity "maps" for these devices. The results indicate high performance at angles that correspond to locations in the plasmonic Brillouin zone (PBZ) where dispersion curves of multiple SPPs converge.

Nanoprinted Plasmonic Crystal

Figure 3:
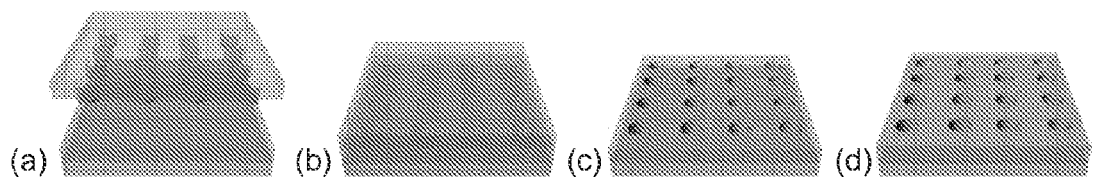
FIG. 3. Plasmonic crystal fabrication process: (a) imprinting; (b) curing; (c) removing; and (d) gold deposition.

Since the discovery of extraordinary optical transmission through subwavelength hole arrays, plasmonic crystals have attracted significant interest in the scientific community. The required structures are typically fabricated either by electron beam lithography in a serial fashion over limited areas with imperfect spatial coherence, or by expensive, advanced forms of projection mode photolithography. A simple, soft imprinting procedure illustrated in FIG. 3 formed the structures used for the work described here. Casting and curing a prepolymer of poly(dimethylsiloxane) (PDMS) against a master of photoresist on a silicon wafer, patterned by projection mode deep ultraviolet lithography, formed the molds according to the following procedures. The master was first placed in a vacuum chamber along with 100 mL of (tridecafluoro-1,1,2,2-tetrahydrooctyl)-1-trichlorosilane (United Chemical Tech) for 2 hours. The resulting silane layer prevents adhesion of the PDMS to the bare $SiO_2$. The stamp was prepared as a bilayer of hard PDMS (h-PDMS) to reproduce accurately the master's features, and soft PDMS (s-PDMS) to provide a flexible support for the brittle h-PDMS. The h-PDMS (Gelest, Inc) was prepared as follows: 3.4 g of poly(7-8% vinylmethylsiloxane)-(dimethylsiloxane), 100 mg of (1,3,5,7-tetravinyl-1, 3,5,7-tetramethylcyclotetrasiloxane) and 50 mg of platinum catalyst were mixed and placed in a vacuum chamber for 5 minutes. After removal from the chamber, 1 g poly(25-30% methylhydrosiloxane)-(dimethylsiloxane) was then added, mixed and the resulting sample was placed back into vacuum for 5 minutes. This prepolymer mixture was spin cast onto the master at 1000 rpm for 300 s and then baked at 65° C. for 2 minutes. The s-PDMS (Sylgard 184, Dow Corning), prepared by mixing base and curing agent at a ratio of 10:1, was then poured onto the h-PDMS. The typical thicknesses used to construct the stamp were 10 μm for the h-PDMS and 3 mm for the s-PDMS. Baking at 65° C. for 2 hours completed the curing of the polymers. Peeling the composite h-PDMS/s-PDMS replica away from the master completed the fabrication of a PDMS mold with the corresponding relief of the master. Many such molds can be produced from a single master, and each mold can be used many times. In the first step of the imprinting procedure, a layer of photo curable polyurethane (PU) (NOA 73, Norland Products) was spin cast onto a glass slide (FIG. 3a). Placing the PDMS mold into contact with this layer and then exposing it to ultraviolet light (350-380 nm; long wavelength ultraviolet lamp, UVP) at ~19 mW/cm$^2$ for 1 hour through the transparent mold cured the polyurethane into a solid form (FIG. 3b). The resulting PU film was ~10 μm thick and presented a relief structure in the geometry of the PDMS stamp. Removing the mold (FIG. 3c), completed the process. The imprinted polyurethane/glass substrate served as a dielectric template for the production of a plasmonic crystal by blanket evaporation of a thin layer of gold (50 nm) on top of a titanium adhesion layer (5 nm). The gold layer was selected to be sufficiently thin to enable operation in transmission mode but thick enough to support SPPs. These simple, low cost fabrication procedures are reliable, robust, and can be applied over large areas. The resolution is exceptionally high; relief features as small as 1-2 nm have been successfully produced with this method.

Figure 4:
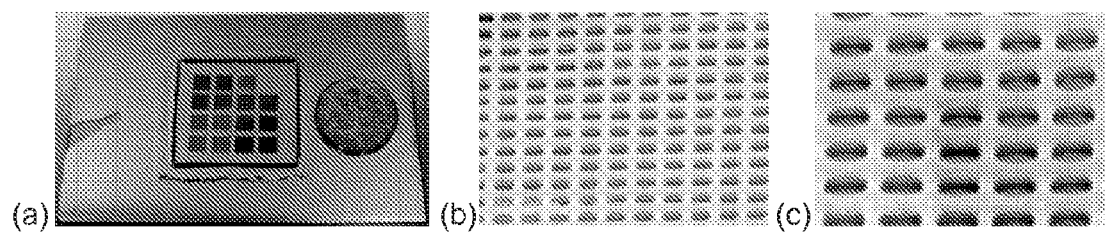
FIG. 4. Two dimensional plasmonic crystal sensor: (a) low resolution image; (b) scanning electron micrograph (SEM); (c) high resolution SEM showing that walls of the depression are free from metal.

FIG. 4 shows scanning electron micrographs of a typical device. The crystal used in this work has a square lattice consisting of depressions with diameters and depths of 545 nm and 300 nm, respectively, and with a periodicity of 700 nm. The walls of the depressions are not coated with metal, due to the directional nature of the gold flux in the electron beam evaporation system that was used.

The SPPs involve evanescent electromagnetic fields in the direction perpendicular to metal/dielectric interface. The depth of the depressions (300 nm) is comparable to the SPP penetration depth into the dielectric medium. In such a geometry, our system consists of a three dimensional plasmonic crystal comprising a continuous metallic layer on the upper surface weakly coupled to an array of isolated metallic islands (positioned on the bottom surfaces of the depressions).

Experiment & Results

Figure 5:
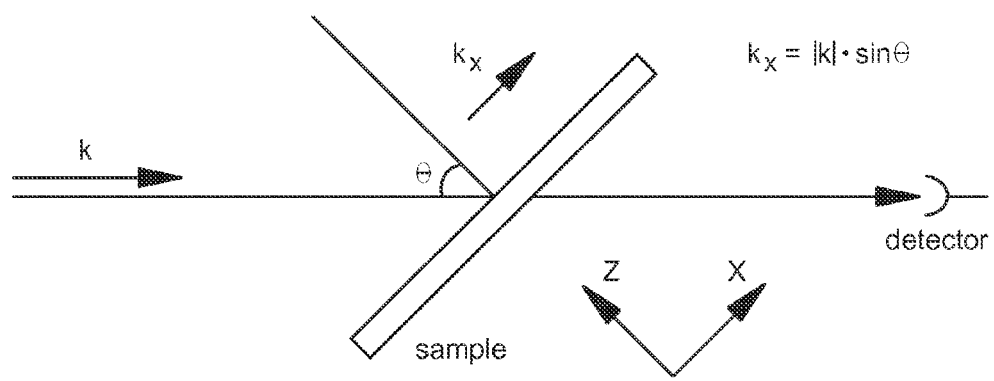
FIG. 5. Experimental zero-order transmission setup.

We performed zero-order transmission experiments in order to obtain the PBZ map of these structures. The scheme of the setup is presented in FIG. 5. The sample was fixed on a 2-axis rotation stage mounted inside of a UV-Vis-NIR spectrophotometer (Cary 5G). One axis turned the device to the required polar angle of incidence θ. The other rotated the sample around the Z axis (FIG. 5). This stage defines the direction for excitation and propagation of the plasmonic modes on the metal surface. The transmission spectra have a nominal spectral resolution of 1 nm, and are collected in a dual beam configuration to account for any intensity fluctuations in the light source.

PBZ maps were acquired by fixing the desired polar angle of incidence (θ) and recording a transmission spectrum over a predefined wavelength range. The angle θ was varied between 0° and 75° with incremented steps of 0.5°. Two main directions inside PBZ were mapped. One corresponded to the Γ-X direction (sample rotated along the axis perpendicular to the grating period), the other to the Γ-M direction (sample rotated around the axis perpendicular to the grating diagonal).

The baseline for background correction was measured using the unstructured and uncoated region of the sample. The 50 nm thick gold film was slightly transparent at a level consistent with expectations for an unstructured film. In contrast, the plasmonic crystal shows strong resonances in transmission intensity that reach ~14% at the maximum and ~0.3% at the minimum for our sample at normal incidence. The overall transmission intensity decreases as the polar angle (θ) increases and shows a value of ~5% at the maximum and ~0.3% at the minimum for E=75°. These spectra are then used for PBZ mapping. The momentum of the SPP at the Γ point in the PBZ is $k_{sppΓ}=0$, at X, $k_{sppX}=\pi/p$, and at M, $k_{sppM}=2\pi/d$, where p is the period of the grating and d its diagonal.

Figure 6:
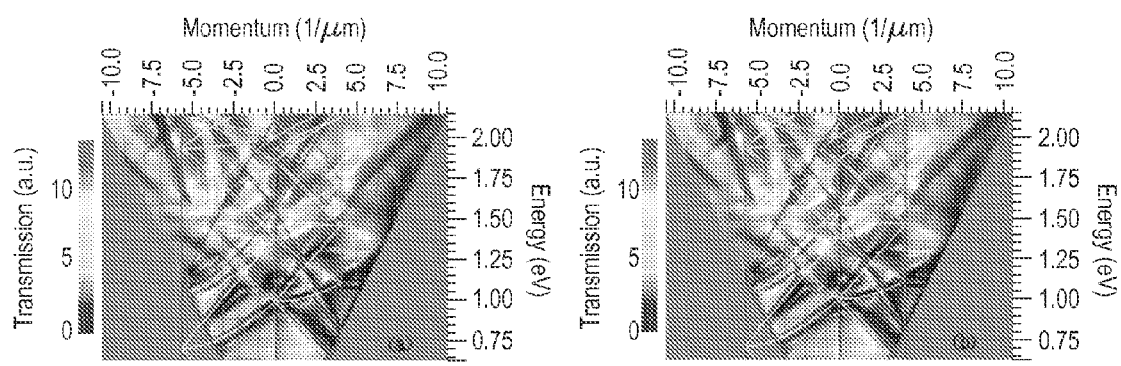
FIG. 6. Plasmonic Brillouin zones (a) before and (b) after the formation of a hexadecanethiol SAM.

The PBZ of the plasmonic crystal measured immediately after gold deposition is presented in FIG. 6a. The surface sensing capability of the device was tested by measuring a sample with a self assembled monolayer (SAM) on the exposed gold formed by contact transfer from a PDMS slab inked in a 1 mM ethanolic solution of hexadecanethiol. Slight changes in the plasmonic dispersion caused by the formation of the SAM are evident upon visual inspection, as revealed by the data presented in FIG. 6b. The large blue triangular regions in the lower left and right corners of FIG. 6 correspond to regions that lie beyond the rotation stage's upper limit of θ=75°.

In order to highlight the effects of the SAM on the PBZ, we recast the data in the form of a sensitivity map using equation (1).

$$\text{Sensitivity} = \text{Transmission}_{SAM} - \text{Transmission}_{initial} \quad (1)$$

Figure 7:
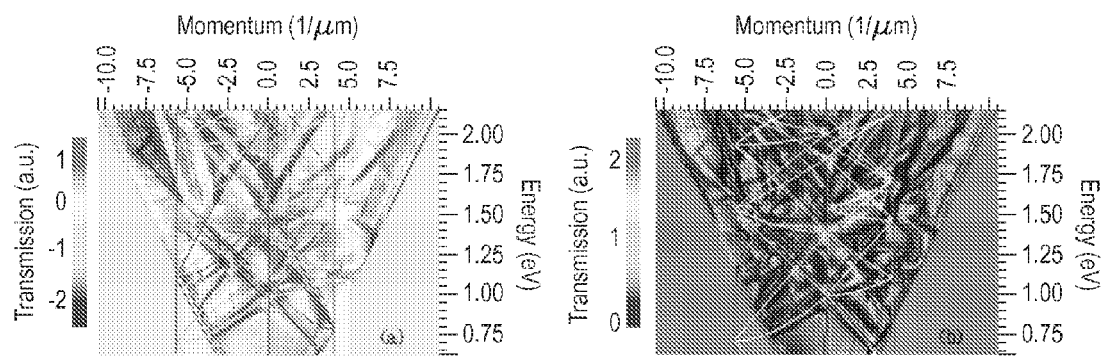
FIG. 7. Plasmonic crystal surface sensitivity: (a) sensitivity map; (b) absolute values of the sensitivity map.

The resulting image is presented in FIG. 7a. The essence of any sensing application is in the accurate detection of the change in signal (here a shift in the position and intensity of the SPP resonances) due to the presence of an analyte. A straightforward way to visualize the response is to examine only the absolute values of such changes. The corresponding absolute sensitivity map is shown in FIG. 7b.

The simplest approach to describe the plasmonic Brillouin zone is to utilize the dispersion relation for SPPs on a smooth metal surface (2).

$$k_{spp} = \frac{\omega}{c}\sqrt{\frac{\varepsilon_d \cdot \varepsilon_m}{\varepsilon_d \cdot \varepsilon_m}}$$

Here ω is the SPP frequency, c is the speed of light, $\varepsilon_d$ and $\varepsilon_m$ are the respective dielectric constants for the corresponding dielectric and the metallic media. The value $\varepsilon_m$ is complex and strongly dependent on frequency. We obtained the dispersion relation of the SPP using experimental data for the dielectric constant of gold. One can build the PBZ by taking into account the periodicity of the plasmonic crystal and folding the SPP dispersion line at the corresponding critical points. The results of this analysis are superimposed onto FIGS. 6 and 7. The black and brown lines represent SPPs localized at the metal/air interface of the plasmonic crystal and propagating in directions perpendicular and parallel to the rotation axis, respectively. The white and yellow lines represent SPPs lying at the metal/polyurethane interface and propagating in directions perpendicular and parallel to the rotation axis, respectively. The red lines represent the critical points: the left line is the M-point; the middle line is the Γ-point; and the right line is the X-point. While the use of the folded dispersion relation for a flat metal is an oversimplification of this grating system, it delivers fairly good agreement for most of the SPP resonance bands. This model however, is not able to correctly describe all of the features observed in the PBZ, but provides very useful description none the less.

The sensitivity map shows that regions with strong resonances exhibit high sensitivity. Some increased sensitivity regions occur, however, near intersections of SPPs on the substrate/metal and air/metal interfaces. At these locations, coupling between the modes can be expected, leading an increase in lifetime and propagation length of the SPP. The highest sensitivity occurs at the Γ-point (maximum ~1.03 eV) where 5 substrate/metal and 1 air/metal modes are interacting.

Figure 8:
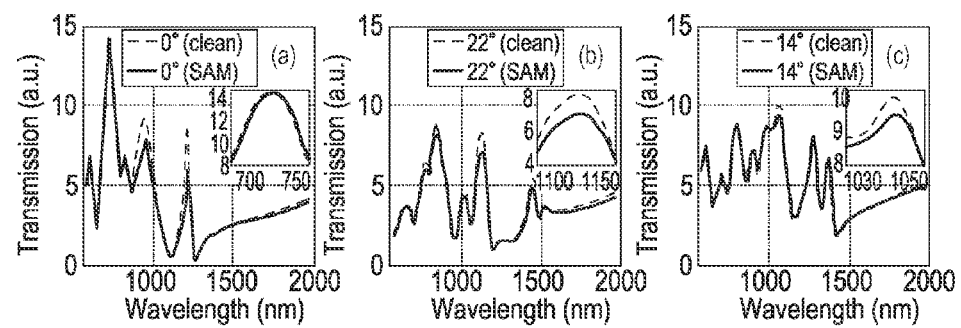
FIG. 8. Transmission spectra at chosen points: (a) 0° (Γ-point); (b) 220 in Γ-X region (maximum sensitivity at $k_x$=2.1 μm; and (c) 140 in Γ-M region (maximum sensitivity at $k_x$=−1.2 μm). Insets show the magnified parts of the spectra in order to highlight the change due to the formation of a hexadecanethiol SAM.

The trends in sensitivity can be better understood from spectra extracted from the maps. The data shown in FIG. 8 correspond to representative angle-dependent transmission spectra measured for both a clean and SAM-modified sensor. Spectra are shown for the Γ-point and for regions where air/metal and substrate/metal modes are crossing showing anomalously high sensitivity. FIG. 8b is for the Γ-X region and FIG. 8c is for the Γ-M region. The wavelength shifts of the resonances in FIG. 8 correlate well with the types of responses seen in conventional SPR systems; these changes largely reflect a modest (~4 nm) red shifting of the position of the resonance due to the refractive index change at the dielectric/metal interface that results from the formation of the ~21 Å thick SAM on the surface. The changes of the relative intensities of the different resonances, however, are more unusual and may provide enhanced sensing capabilities.

Conclusions

In conclusion, we have demonstrated the potential of soft imprinting technology for fabricating plasmonic crystal sensors. Sensitivity maps of representative device were constructed from angle-dependent transmission experiments. The sensors exhibit high sensitivity when operated at certain angles. These angles correspond to locations in the plasmonic Brillouin zone where dispersion curves of unperturbed SPP modes converge. This observation enables a future classes of advanced plasmonic crystal biosensors.

Example 2

Quantitative Multispectral Biosensing and Imaging Using 3D Plasmonic Crystals

Abstract

We have developed a class of three dimensional plasmonic crystal that consists of multi-layered, regular arrays of subwavelength metal nanostructures. When coupled with quantitative electrodynamics modeling of their optical response, these crystals enable full multi-wavelength spectroscopic detection of molecular binding events with sensitivities that correspond to small fractions of a monolayer. The high degree of spatial uniformity in the crystals, which are formed by a soft nanoimprint technique, provides the ability to image these binding events with micron spatial resolution. These features, together with compact form factors, low cost fabrication procedures, simple readout apparatus, and ability for direct integration into microfluidic networks and arrays, suggest promise for these devices in label free bioanalytical detection systems.

Background and Results

Macromolecular biological interactions are critically important to the complex signaling and molecular recognition processes that occur in virology, cell signaling, DNA hybridization, immunology, DNA-protein interactions, and drug discovery, among others. (cite references here) These systems can be probed by immobilizing one component of a binding pair on a surface and following the mass coverage changes upon exposure to the complimentary recognition element. Surface plasmon resonance (SPR) instruments capable of measuring changes in refractive index near a metal surface accomplish this aim with sub-monolayer sensitivities, without the need for fluorescent labeling. Conventional SPR systems use prisms to couple light into a single surface plasmon (SP) mode on a flat, continuous metal (typically gold) film. This cumbersome experimental setup is difficult to integrate into low-cost, portable, image based devices for rapid bioanalytical measurements or for evaluation of mass-limited samples. More recent work shows that metal nanoparticles and nanostructured metal films can be used for SPR type sensing, without coupling prisms. These systems, however, have some important limitations. First, even though some of the nanostructured films provide multiple plasmonic resonances, their current implementations involve metrics for binding sensitivities that are worse than those of conventional, single resonance SPR devices. Second, fabrication of the type of large area, spatially coherent arrays of highly uniform nanostructures (e.g. holes in films) that are best suited for sensing and imaging is cost prohibitive with conventional techniques (i.e. electron or ion beam lithography). Third, the basic nature of light interactions with these structures, which is generally thought to involve the excitation of Bloch wave surface plasmon polaritons (BW-SPPs), with contributions also arising from surface plasmon resonances localized at the edges of the holes (LSPRs), as well as Wood's anomalies and other forms of diffracted light, remains uncertain, thereby frustrating their optimized use for sensing. This Example introduces a class of three dimensional (3D) plasmonic crystal and an analysis approach that overcome these limitations. The physics of these crystals can be understood at a quantitative level through computational electrodynamics modeling. Furthermore, this understanding can be exploited in a highly sensitive, full multi-spectral plasmonic approach to chemical sensing and imaging. These capabilities are enabled, in part, by the exceedingly high quality and unusual geometries of the crystals which are formed, at low cost, with a form of soft nanoimprint lithography. Direct integration of these devices into microfluidic networks for quantitative imaging of molecular binding events at the sub-monolayer level and with micron spatial resolution demonstrates several of their attractive features.

Figure 15:
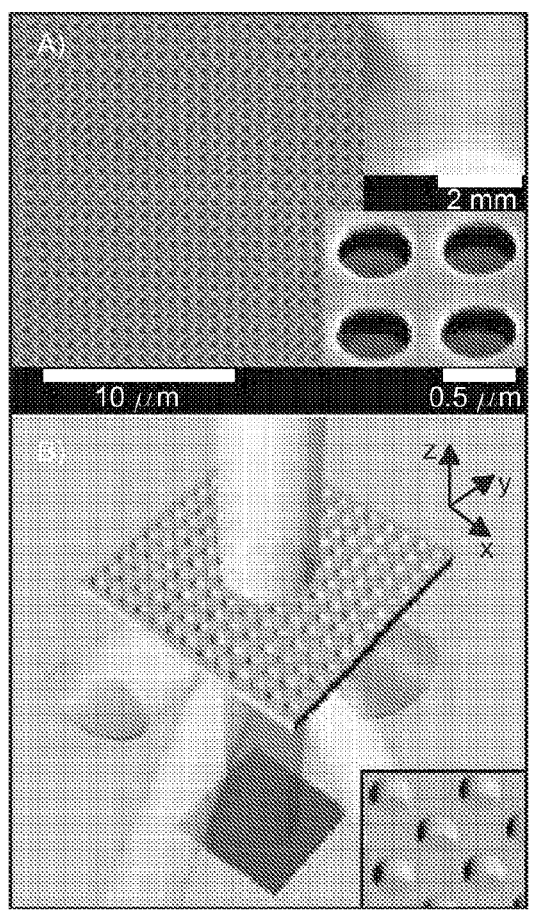
FIG. 15. Plasmonic crystal sensor design: a) Large area SEM image of the nanostructured gold surface (upper inset—optical image) consisting of a square array of circular impressions with gold disks in the embossed wells (bottom inset); b) Experimental normal incidence optical setup detecting the zeroth order transmission beam.

The crystals use large area square arrays of cylindrical wells (typically $2.6 \times 10^6$ wells per sample) with diameters of ~480 nm, depths of ~350 nm and center to center spacings of ~780 nm, fabricated by soft nanoimprint lithography in films of a photocurable polyurethane. Uniformly depositing thin films of gold (~50 nm thick) onto these samples coat the raised and recessed regions to create a 3D plasmonic crystal that consists of an array of nanoscale holes in a gold film with a second level of gold in the form of isolated disks at the bottoms of the embossed wells (FIG. 15a). Shining light on these samples stimulates multiple plasmonic and related resonances, many of which involve strong coupling between the film and the disks. The compact form factor and the simple fabrication procedures yield a low cost, but extremely high quality device that is easily probed and integrated into microfluidic or portable systems.

Figure 16:
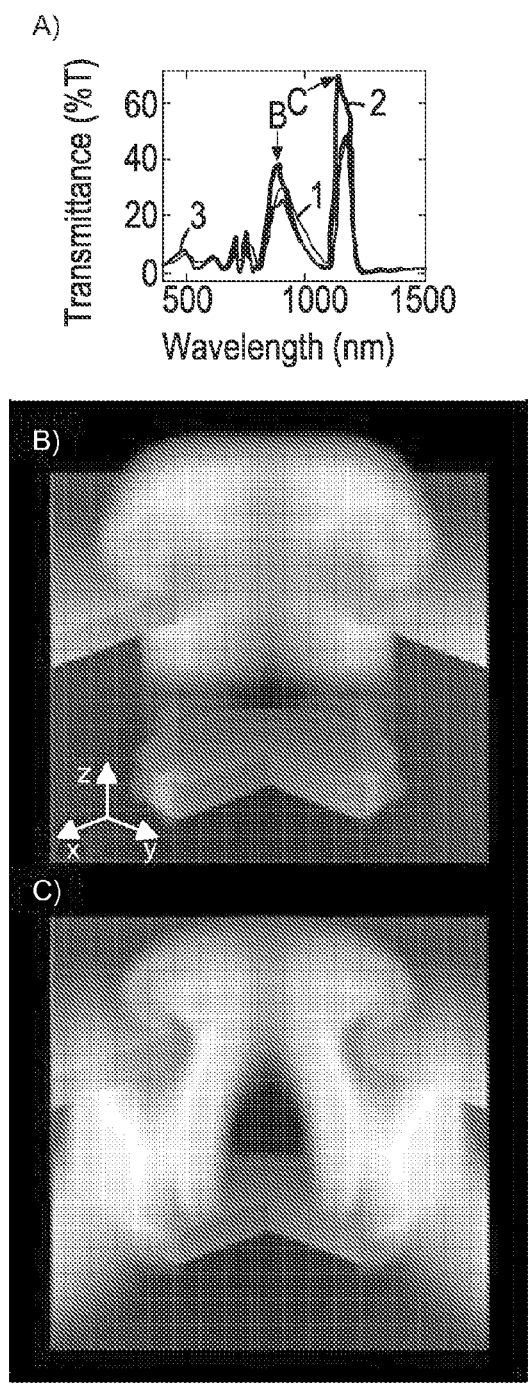
FIG. 16. Simulated optical transmission through nanostructured surfaces: a) Experimental (blue—1) plasmonic transmission spectra along with simulated spectra of an ideal square array (green—2) and a square array with gold deposits at the bottom of the wells (red—3); b) Electromagnetic field distributions in the nanowells exhibit significant intensity in the hole center extending away from the surface at 883 nm; c) Coupling between the metal disk at the bottom of the well and the top surface at 1138 nm.

When operating in normal incidence transmission mode, these devices exhibit strong spatial and wavelength-dependent intensity modulations involving absorptive, diffractive and plasmonic effects (FIG. 15b). Full three dimensional finite-difference time-domain calculations (FDTD) with appropriate periodic boundary conditions accurately model the transmission characteristics and the electromagnetic field distributions in and around the metal nanostructures of the device. The two largest features in the spectra (FIG. 16a) are associated with a Fano interference of an assignable BW-SPP excitation on the metallic surface and directly transmitted light. The near-field intensity associated with peak B is most significant in and around the top surface of the embossed holes (FIG. 16b), while the intensity associated with peak C is located around the bottom gold disk and extends vertically up to the hole opening, indicative of strong disk-hole coupling (FIG. 16c). This strong coupling implies that peak C is sensitive to the structural details of the bottom disk. Indeed, quantitative modeling of the experimental spectra requires explicit consideration of fine details, even in these extremely high quality samples, such as small (20-30 nm) isolated and sparse grains of gold that form near the edges of the disks during the physical vapor deposition process. The presence of these grains reduces substantially the overall transmission of peak C. The pronounced sensitivity of the spectra to subtle features such as these highlights the very demanding requirements placed on the fabrication procedures to realize structures with reproducible, sharp resonant features that can be modeled accurately. The soft nanoimprint technology used here, which can achieve replication fidelity down to the molecular regime, is critical to the successful formation of the crystals. In addition, the unusual, 3D geometries that result from this process involve strong electromagnetic couplings between the bottom gold disks and the top gold surface, which are absent from standard nanohole array systems. As illustrated by the modeling, this coupling contributes to enhanced sensitivities in the form of large spectral responses and additional spectral features.

Figure 17:
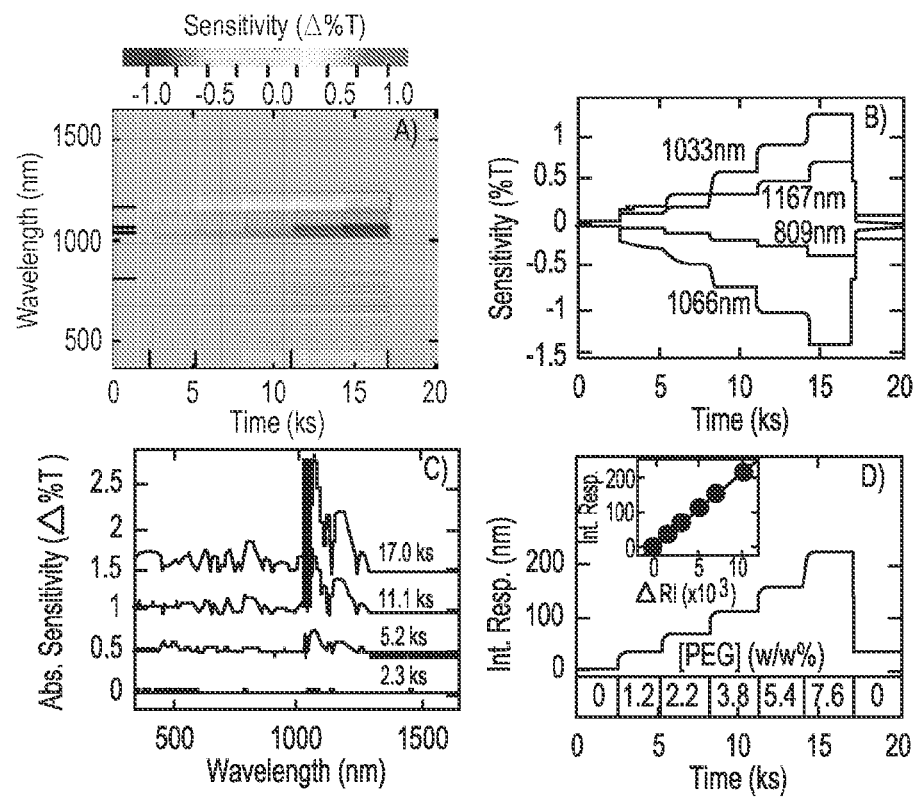
FIG. 17. Plasmonic crystal response to sequential injections of aqueous PEG calibration solutions. The injection sequence, with concentrations given as weight %'s, is indicated in the figures. A) Difference map; b) Single wavelength kinetic responses at 1167 nm (blue), 1066 nm (green), 1033 nm (red), and 809 nm (cyan) with linear correlation to index of refraction (inset); c) Absolute difference spectra with increasing PEG concentration—0% (black), 1.2% (blue), 3.8% (green), and 7.6% (red); d) Integrated multiwavelength plasmonic response with linear correlation to index of refraction (inset).

The transmission properties are strongly sensitive not only to the structural features of the samples but also, of course, to the nature of the dielectric medium immediately contacting the crystal surface. The response of a crystal mounted in a fluid flow cell to a series of poly(ethylene glycol) (PEG) solutions of increasing concentration, which results in systematic variations in the bulk index of refraction (FIG. 17), provides a means to demonstrate this sensitivity. The position of a single resonance, chosen for its high sensitivity to changes refractive index, was found to redshift by ~700 nm/RIU, which is comparable to or larger than the responses of other reported nanostructured plasmonic devices. Although surface binding events are typically monitored by following the response of individual peaks, the complex nature of the spectra coupled with their quantitative understanding enables a type of full multi-spectral analysis that offers significantly enhanced sensing capabilities. In this approach, absolute changes in transmission are measured over the entire spectral window, then integrated to yield a single multi-spectral binding metric. The series of difference spectra, as referenced to the spectrum at time t=0, show substantial changes in both peak positions and intensities (FIG. 17a). For the geometry of the crystal used in this study, the most sensitive multi-wavelength responses occur in the NIR region (900 nm-1250 nm), an aspect that can be controlled by changing the dimensions of the periodic array. These differing levels of sensitivity observed at the various wavelengths correlate to the degree of overlap between the electric field distributions associated with the plasmonic resonances and the surrounding bulk fluid (FIG. 17b). The total response at all wavelengths, including positive and negative intensity changes, is reflected in the integrated absolute difference spectra with increasing refractive index (FIG. 17c). The integrated response linearly correlates with changes in the refractive index of the bulk PEG solution (inset of FIG. 17d), similar to the single peak analysis, but with a vastly improved sensitivity (~22000 nm/RIU). (Note that the data of FIG. 17d does not return to the baseline during the final water rinse, demonstrating the sensitivity of the system to the expected irreversible adsorption of a thin layer of PEG) This linear correlation of the provides an explicit foundation on which to develop high sensitivity, fully quantitative applications of the 3D plasmonic crystals in chemical sensing—an example of which is illustrated via a protein binding assay modeled using a simple mathematical framework developed for traditional, reflection mode SPR spectroscopy.

Figure 18:
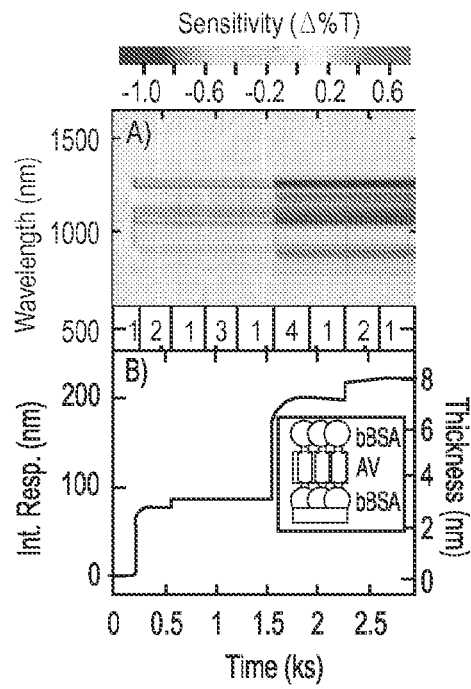
FIG. 18. Plasmonic crystal biotin-avidin binding assay: a) Difference map of specific binding assay; b) Integrated multiwavelength plasmonic response with an injection sequence of phosphate buffered saline (1—PBS), biotinylated-bovine serum albumin (2—bBSA), bovine serum albumin (3—BSA), and avidin (4—AV) along with a schematic representation of the three step bBSA-avidin-bBSA assay (inset).

The well-known biotin-avidin ligand-receptor conjugate provides a model system to illustrate the functionality of these devices in a realistic analytical bioassay (FIG. 18). Pre-exposing the surface of the sensor to a solution of biotinylated-bovine serum albumin (bBSA) leads to a large increase and subsequent plateau in the integrated response of the sensor (FIG. 18b) upon the formation of a bBSA monolayer. This layer renders the surface of the sensor inert to further nonspecific adsorption, as demonstrated by the lack of sensor response after rinsing this monolayer with buffer and then exposing it to a solution of non-functionalized BSA. Subsequent exposure to avidin, however, yields a large response due to a specific binding interaction of the avidin to the surface-bound bBSA. The surface-immobilized avidin was then used to complete a sandwich-based assay by binding a final terminating layer of bBSA to the remaining free biotin binding sites on the avidin layer (inset FIG. 18b). This procedure resulted in a response that was smaller than that observed for the adsorption of the initial bBSA, an observation that follows the patterns of layer dependent mass coverage generated in assays of this sort. The integrated response can be correlated to an effective thickness of protein at each step in the assay by using the bulk refractive index sensitivity factor determined from the PEG calibration (~22,000 nm/RIU). The resulting effective thicknesses agree quantitatively with values reported in the literature. The resolution, defined as the minimum measurable refractive index change, is determined by the noise inherent in the baseline of the integrated signal. For the plasmonic devices introduced here, the resolution ($1 \times 10^{-5}$ RIU, which corresponds to an effective thickness of 0.02 nm) approaches the limits of the very highest resolution systems currently available.

Figure 19:
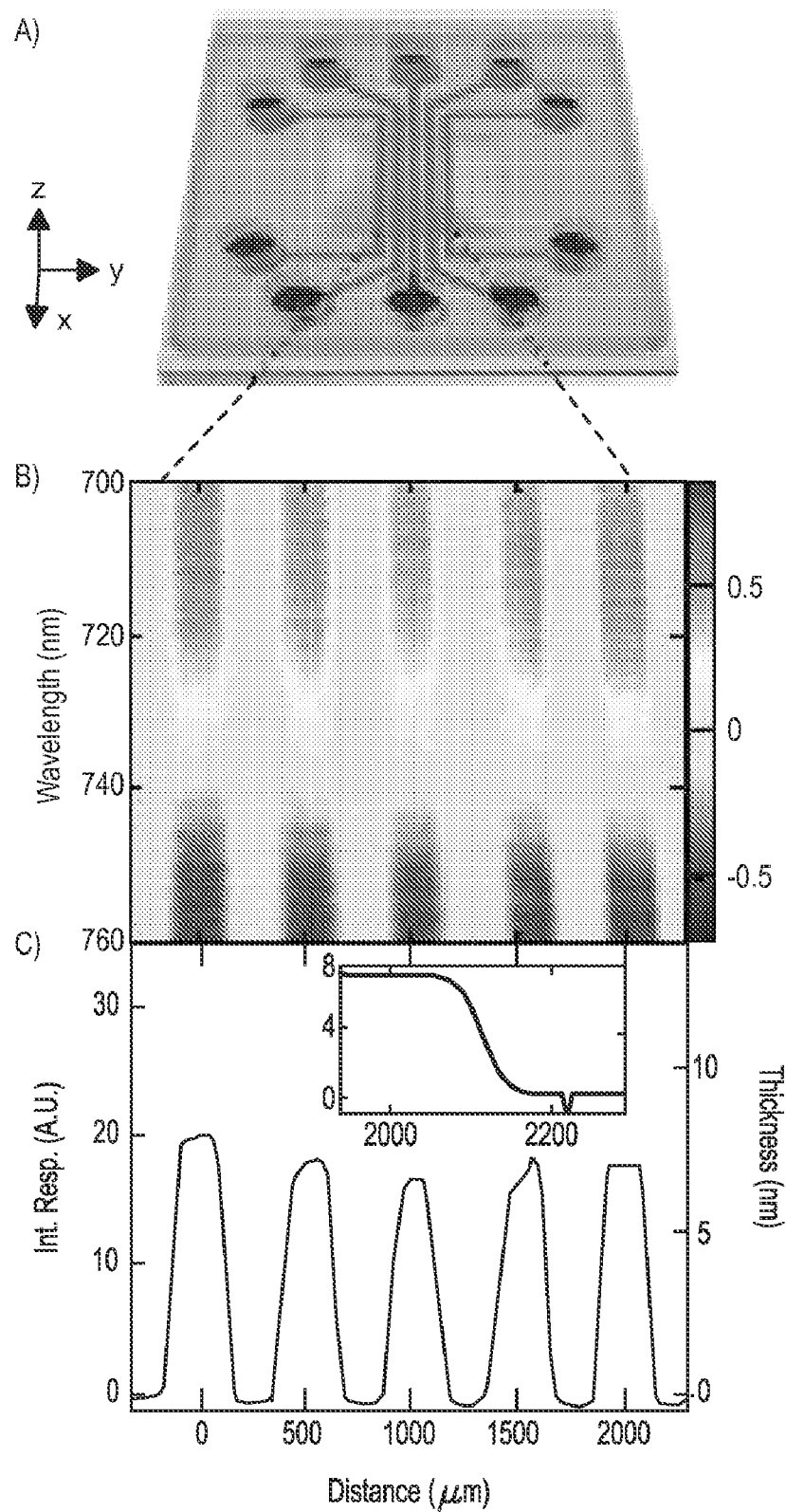
FIG. 19. Imaging of microfluidically patterned fibrinogen adsorbed on a nanostructured plasmonic crystal: a) Schematic representation of microfluidically defined protein patterns on a plasmonic crystal; b) spectroscopic imaging of plasmonic response; c) Integrated spectral response of fibrinogen adsorption with a spatial resolution of ~20 μm.

The capacities for quantitative biosensing also provide new foundations for analytical imaging of large area multiplexed bioassays. This capability was demonstrated using nonspecifically adsorbed fibrinogen patterned on the surface of a plasmonic crystal with an integrated microfluidic channel system (FIG. 19a). The resulting spatially varying protein regions were spectroscopically imaged using dispersion optics in conjunction with a CCD array detector. and then differenced (relative to inter-channel region) to reflect the spectral shifts in regions of high protein coverage (FIG. 19b). The spectral image shows five stripes with the expected geometries, each corresponding to a fibrinogen line. The procedure used to obtain quantitative protein coverages in the biotin-avidin case was then applied to the spectroscopic image, using an appropriate (frequency truncated) version of the PEG calibration data given in FIG. 17. The result is an integrated spatial profile of the protein lines that corresponds to an effective thickness of ~7 nm (FIG. 19c), which is a reasonable value based on the molecular dimensions of fibrinogen. The edge resolution of the features in this profile is ~20 µm, while the imaging system was found to have a limiting resolution of ~17 µm. The subsequent 3 µm loss in resolution of the plasmonic image can be associated with the characteristic propagation lengths of plasmons in these crystals, which are significantly shorter than those on flat metallic films due to scattering from the nanostructured features on the crystal. An imaging resolution at micron scales combined with the large area defect-free aspect of the crystals suggest a promising platform for massively parallel diagnostic bioassays.

In summary, this work demonstrates a new form of highly sensitive quantitative chemical sensing that uses multi-spectral and spatially resolved techniques with integrated 3D plasmonic crystals. Theoretical modeling quantitatively accounts for the observed unique optical properties of these architectures and illustrates the complex electromagnetic field distributions around the multilevel nanostructured features in these systems. These devices can be fabricated at low cost and provide a platform from which to perform quantitative biochemical (and other forms of) sensing with extremely high sensitivities—in ways that facilitate miniaturization and integration into portable microfluidic lab-on-a-chip instrumentation.

Materials and Methods

Fabrication of Plasmonic Crystals. Polydimethylsiloxane (PDMS; Dow Corning Sylgard 184) and a photocurable polymer (PU; Norland Products NOA 73) were used to fabricate nanostructured molds using soft UV nanoimprint lithography, as described in Example 1. Briefly, a PDMS stamp bearing various square arrays of posts with diameters of 480 nm, heights of ~350 nm and pitches of 780 nm were replicated from a master—many PDMS stamps were produced from a single master. The elastomeric stamp was used to emboss a layer of NOA on a glass slide, which was cured by exposing the NOA to UV light through the PDMS stamp for 3 minutes. Removing the PDMS stamp after curing yielded an NOA mold having a relief structure with the geometry of the PDMS stamp. Each PDMS stamp could be used to make ~8 NOA molds before degradation of the pattern was observed—caused by cohesive failure of the PDMS posts and transfer to the cured NOA. The imprinted NOA samples were directly covered with a 50 nm thick layer of gold by electron beam evaporation (Temescal FC-1800). A titanium adhesion layer was found to be unnecessary and undesirable, as it reduced and broadened the observed transmission peaks. The resulting plasmonic devices were found to be of high quality with few pixel defects over large areas (~20 mm$^2$) as determined by SEM (Hitachi S4700, 10 kV) imaging.

Figure 9:
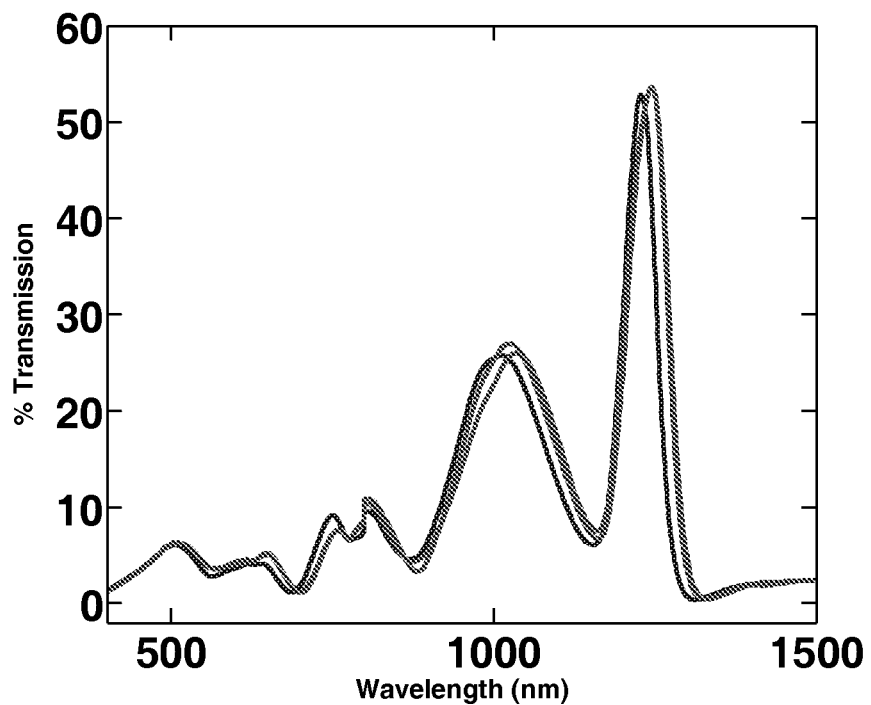
FIG. 9. Normal incidence transmission spectra of three independently patterned plasmonic crystals.
Figure 10:
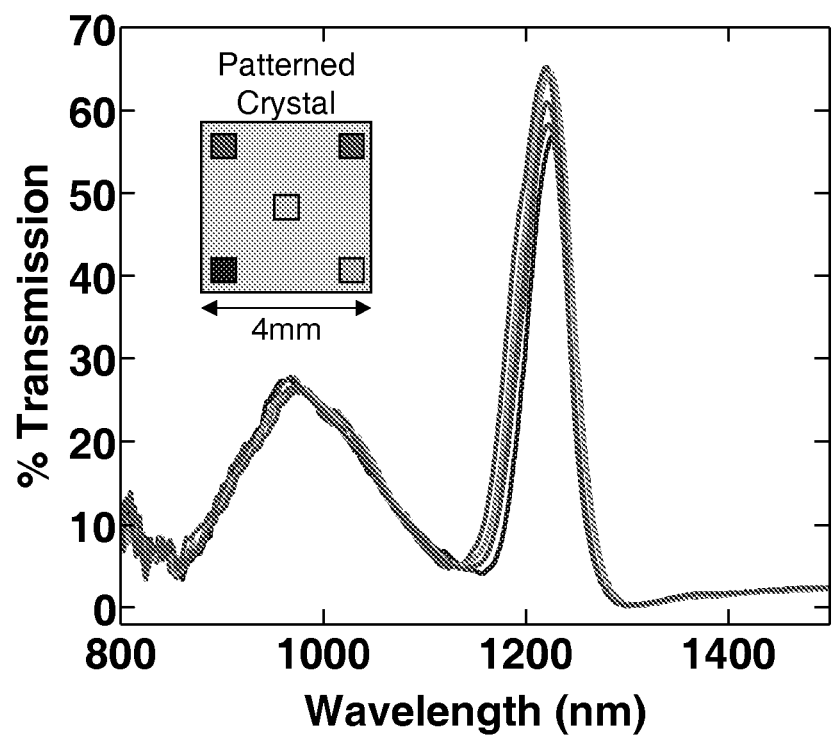
FIG. 10. Normal incidence transmission spectra of the two lowest energy plasmonic resonances seen in different regions of the nanopatterned area of a crystal (blue—lower left quadrant; green—upper left quadrant; red—upper right quadrant; cyan—lower right quadrant; violet—middle).
Figure 11:
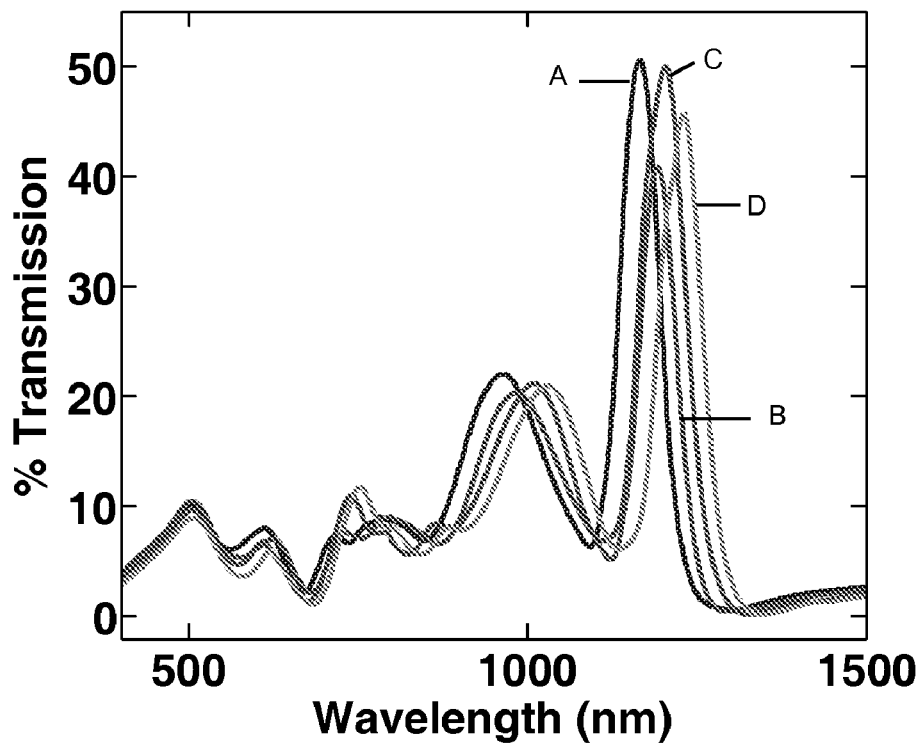
FIG. 11. Normal incidence transmission spectra of plasmonic crystals with increasing nanohole diameter and pitch (blue (A)—d=420 nm, p=720; green (B)—d=440 nm, p=740 nm; red (C)—d=460 nm, p=760 nm; cyan (D)—d=480 nm, p=780 nm).

Transmission-Mode SPR Spectroscopy. Spectra of the plasmonic crystals were acquired on a Varian 5G UV-Vis-NIR spectrophotometer, operating in normal incidence transmission mode. FIG. 9 shows the transmission spectra of multiple crystals fabricated from a single PDMS stamp all exhibit nearly identical spectra. The high spatial uniformity of a single plasmonic crystal is demonstrated in FIG. 10, where spectra taken using a microscope attached to a Bruker FT spectrometer at several separate and distinct regions of a single crystal appear nearly identical. The transmission spectra of these devices depend strongly on the properties of the fabricated holes (shape, size, period, and structure). Using these parameters the gratings can be tuned to offer maximum sensitivity at specific wavelengths of interest across the UV-Vis-NIR regions of the electromagnetic spectrum as demonstrated in FIG. 11 where there exists a consistent redshift in the observed plasmon resonance energies as the period and diameter of the nanostructures is increased. These data, in total, illustrate the high fidelity and reproducibility of the pattern transfer process.

Time Resolved Experiments. A home-built flow cell was constructed around the nanostructured area of the plasmonic crystal using a PDMS gasket sandwiched between a microscope slide and the sensor. Solutions were introduced into the flow cell using a mechanical syringe pump (Harvard Apparatus) at a flow rate of 0.1 ml/min. Transmission spectra were continuously acquired as solutions were passed over the plasmonic crystal with a temporal resolution of ~90 s. Introduction of a new solution was accomplished by first injecting 1 ml at 1 ml/min to completely flush the cell of the previous solution, after which the 0.1 ml/min flow rate was resumed. Solutions were generally allowed to equilibrate under constant flow for at least 30 minutes before proceeding to the next solution.

Solutions. Poly(ethylene glycol) (PEG) calibration solutions were prepared by dissolving commercially available PEG with an average molecular weight of 10,000 g/mol (Sigma) in MilliQ water. The refractive indices of these solutions were independently measured using an Abbe refractometer (Bausch and Lomb). Solutions of avidin (Molecular Probes), bovine serum albumin (BSA; Sigma), biotinylated-BSA (bBSA; Pierce), and fibrinogen from bovine plasma (Sigma) were used as received and prepared in phosphate buffered saline (PBS; Bio Whittaker).

Figure 12:
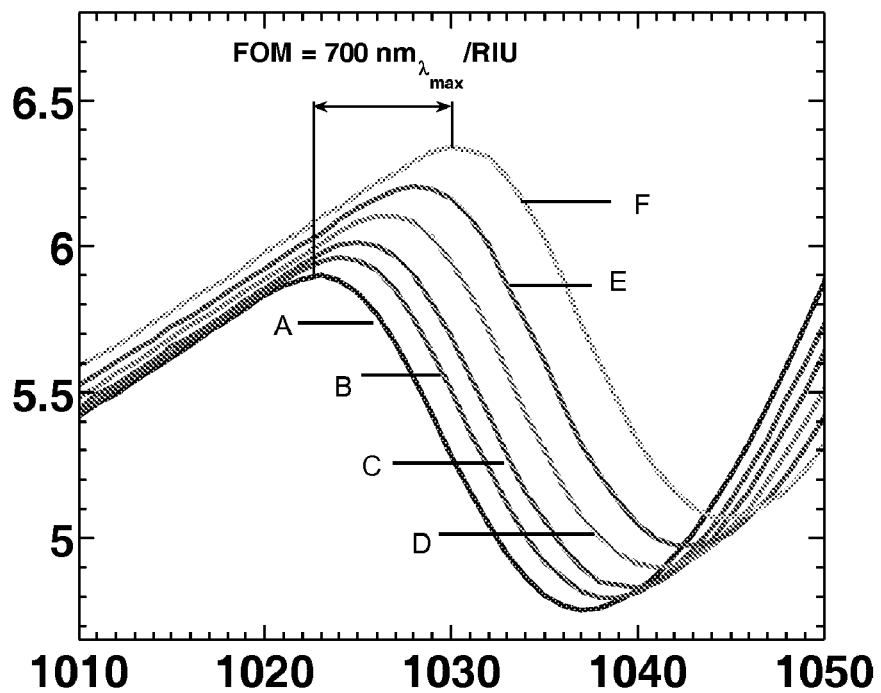
FIG. 12. Peak shift ($\lambda_{max}$) of a single plasmonic resonance as a function of increasing bulk refractive index—0% (blue—A), 1.2% (green—B), 2.2% (red—C), 3.8% (cyan—D), 5.4% (violet—E), and 7.6% (yellow—F), where the percentages indicate the weight percent of the aqueous PEG solutions used to modulate the refractive index.

PEG Calibration. The bulk refractive index sensitivity of the plasmonic crystals was determined by passing solutions of increasing concentration of PEG (0-7.6 wt %) through a fluid flow cell containing a plasmonic crystal. Both changes in peak positions and intensities were observed over most of the spectral range as the refractive index of the solution was increased. The resolved peak at ~1023 nm was found to have the largest change in spectral response, which includes a red-shift and increase in intensity with progressively more concentrated aqueous solutions of PEG (FIG. 12). The peak maxima vary linearly with a sensitivity of ~700 nm/RIU.

Figure 13:
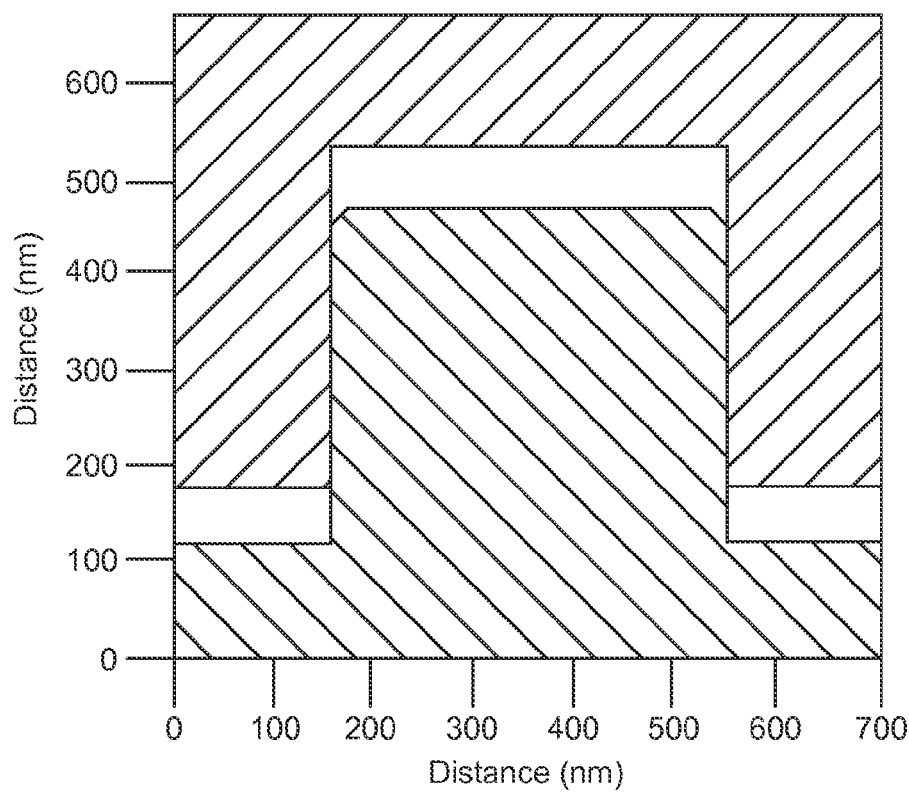
FIG. 13. Schematic diagram of the pileup features included in the field distribution simulations.
Figure 14:
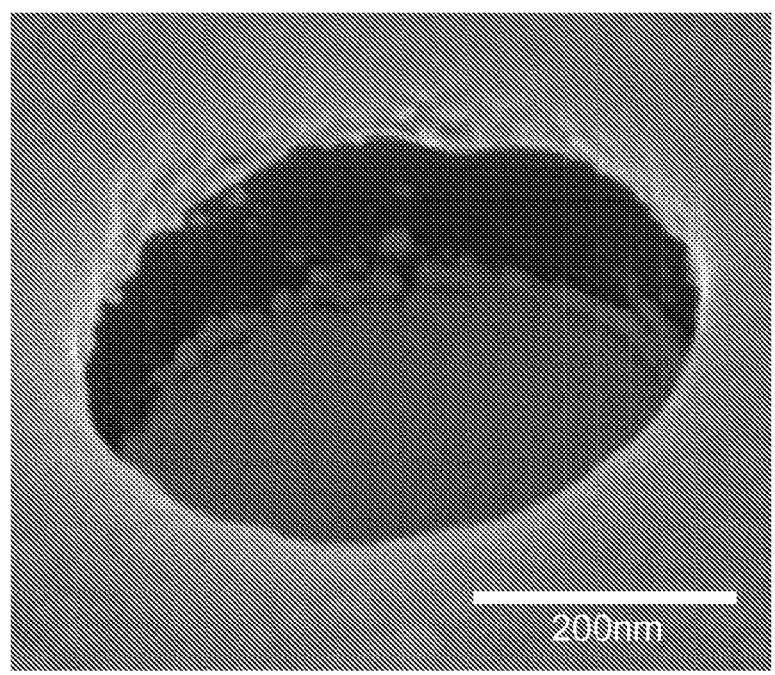
FIG. 14. Tilted SEM image of an individual plasmonic nanohole illustrating granular pileup at the gold disk/NOA interface.

Imperfections in Theoretical Simulations. Good agreement between the experimental and simulated spectra was obtained by introducing small imperfections in the structure of the modeled disk at the bottom of the wells. These imperfections consisted of a slight granular accumulation of gold along the sidewalls of the nanowells just above the edges of the gold disks (FIG. 13). This accumulation of gold at the edges of the disks was observed in the high-resolution SEM images of the nanowells (FIG. 14), and serves to illustrate the extreme structural sensitivity of the plasmonic devices.

Plasmonic Crystal Spectral Imaging. The surface of a plasmonic crystal was patterned with five lines of nonspecifically adsorbed fibrinogen using a series of PDMS microfluidic channels (250 µm wide with 500 µm pitch). These channels were filled with a 0.1 mg/ml fibrinogen solution using the channel outgas technique (COT), and the protein allowed to adsorb for 1 hour, after which they were rinsed with PBS. The PDMS was then removed and the patterned plasmonic crystal was rinsed with PBS and imaged using a home-built imaging system. A 1 mm×5 mm area of the crystal was illuminated with a white light source (Ocean Optics HL-2000) and imaged onto the slit of a monochromator (Acton Research SpectraPro 300i) using two lenses. The dispersed light exiting the monochromator was projected onto a liquid nitrogen cooled 1024×1024 CCD (Princeton Instruments) to generate a spectral image consisting of spatial information on one axis and spectral information on the other.

Example 3

Plasmonic Crystal Sensors, Systems and Sensing Methods

A soft embossing procedure has been used to construct a new form of integrated 3D plasmonic crystal sensor—one possessing unprecedented sensitivity and here-to-fore unavailable capacities for imaging based chemical detection and analysis. The device consists of a sub-wavelength optic structure comprised of a series of patterned nanometer sized impressions in a polymeric substrate, upon which metal films are subsequently deposited (such as Au and Ag along with optically passive coatings as may be required to modify the chemical properties of the sensors surfaces). An embodiment of the device fabricated in this way consists of hierarchically integrated metallic gratings that can be used to elicit strong, spectroscopically discriminatable responses to light via the excitation of plasmons. The plasmonic response in turn provides a direct means for carrying out ultrasensitive chemical detection including sensing directly within integrated novel form factor systems (96 well plates, microfluidic devices, etc.).

The subwavelength grating structures allow a direct coupling of light to the plasmonic bands of the device with reading done in their reflection or transmission mode. The frequency responses can be adjusted via the design rules used to construct the device, with the optical properties typically being selected to provide responses in a range of wavelengths best suited for a particular form of chemical analysis. The 2D and 3D integration of the sub-micron grating systems allows the coupling of optical energy (photons) into surface confined oscillations in charge density at a metal/dielectric interface (plasmons) using a simple normal incidence transmission mode optical setup.

The requirements for efficient coupling are strictly defined by the optical properties of the materials at the interface—mainly refractive index—and are highly frequency dependent, resulting in numerous peaks in the transmission spectra. Integrating the spectral response of the sensor to changes in refractive index of the dielectric layer over all observed frequencies yields a figure of merit with extremely high limits of detection—one surpassing all known forms of plasmonic sensors and approaching the limits of detection (LOD) in microbioanalytical assays typically associated with laser induced fluorescence (LIF). In addition to the multiwavelength aspect of this device, the unique nanostructured surface promotes enhanced electric field distributions at the center of the impressions allowing for extremely sensitive detection of minute quantities of surface bound species; a property useful for multiplexed protein assays. Sensing in this case is universal—being based on ultrasensitive responsiveness to the refractive index of the medium lying within a narrow boundary layer adjacent to the plasmonic crystal's surface and thus requiring no fluorescent label.

The nanostructured features can be fabricated in microarray formats as well as over large areas (~16 mm$^2$) with very low defect densities. In combination with a video detection system, it is possible to image molecular recognition events occurring on the sensor surfaces—this capacity being demonstrated via a fully quantifiable protein binding affinity assay carried out using a microfluidically patterned protein array. The devices capacities allow direct quantification of binding with both high spatial and temporal resolution.

Integrating this device into a microfluidic chip is readily accomplished using polydimethyl-siloxane (PDMS) stamps in which complex networks of fluid channels can be individually addressed. Modifying the gold surface with non-specifically bound proteins or covalently attached organic molecules results in significant spectral responses and provides a simple means to build more complex protein arrays. These unique properties present a generic sensing platform that can be scaled to multiple analytes in a small form factor portable device with extreme sensitivity. Modifications for direct gas phase sensing are also possible.

Example 4

Fabrication of Plasmonic Crystal Sensors by Imprint Lithography

The present invention includes fabrication methods wherein elastomeric stamps, molds and/or photomasks may be repeatedly used to generate two dimensional and three dimensional plasmonic crystals via soft lithographic imprinting techniques. To illustrate this capability of the present invention the spectra of plasmonic crystals generated by successive stamping protocols using the same PDMS poly(dimethylsiloxane) stamp.

Figure 20:
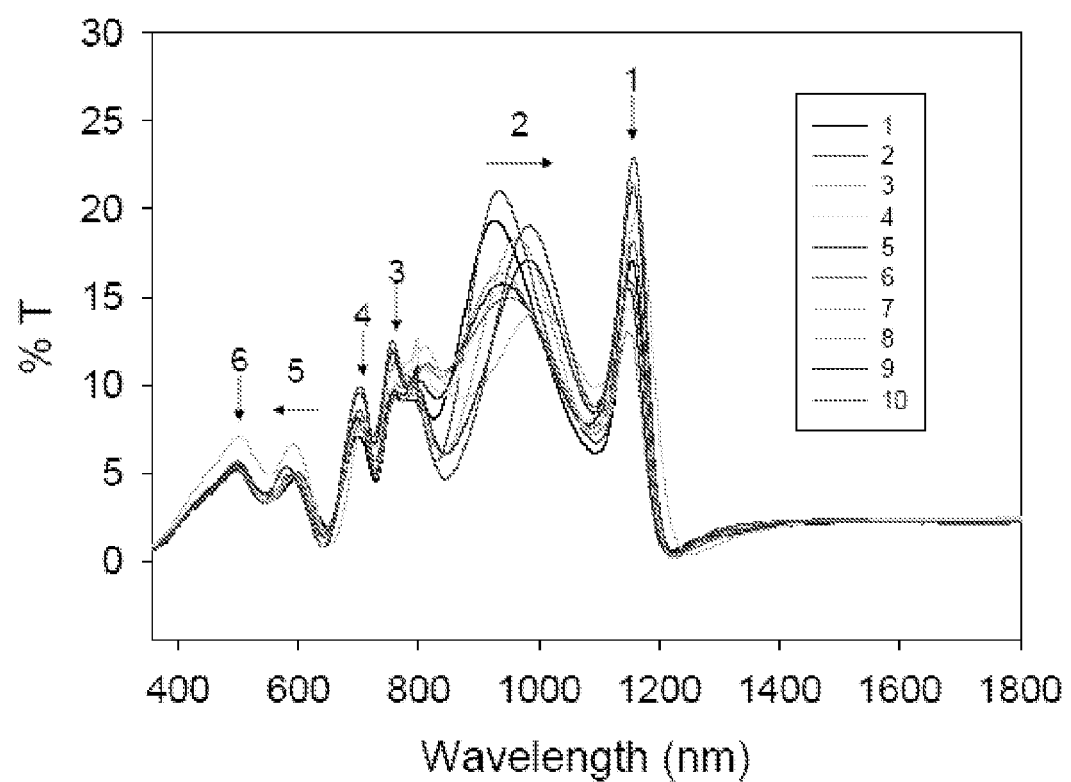
FIG. 20 provides transmission spectra of 10 sequentially stamped plasmonic crystals having a periodic array of recessed features with a diameter of 480 nm and a periodicity of 780 nm.

FIG. 20 provides transmission spectra of 10 sequentially stamped plasmonic crystals having a periodic array of recessed features with a diameter of 480 nm and a periodicity of 780 nm.

Figure 21:
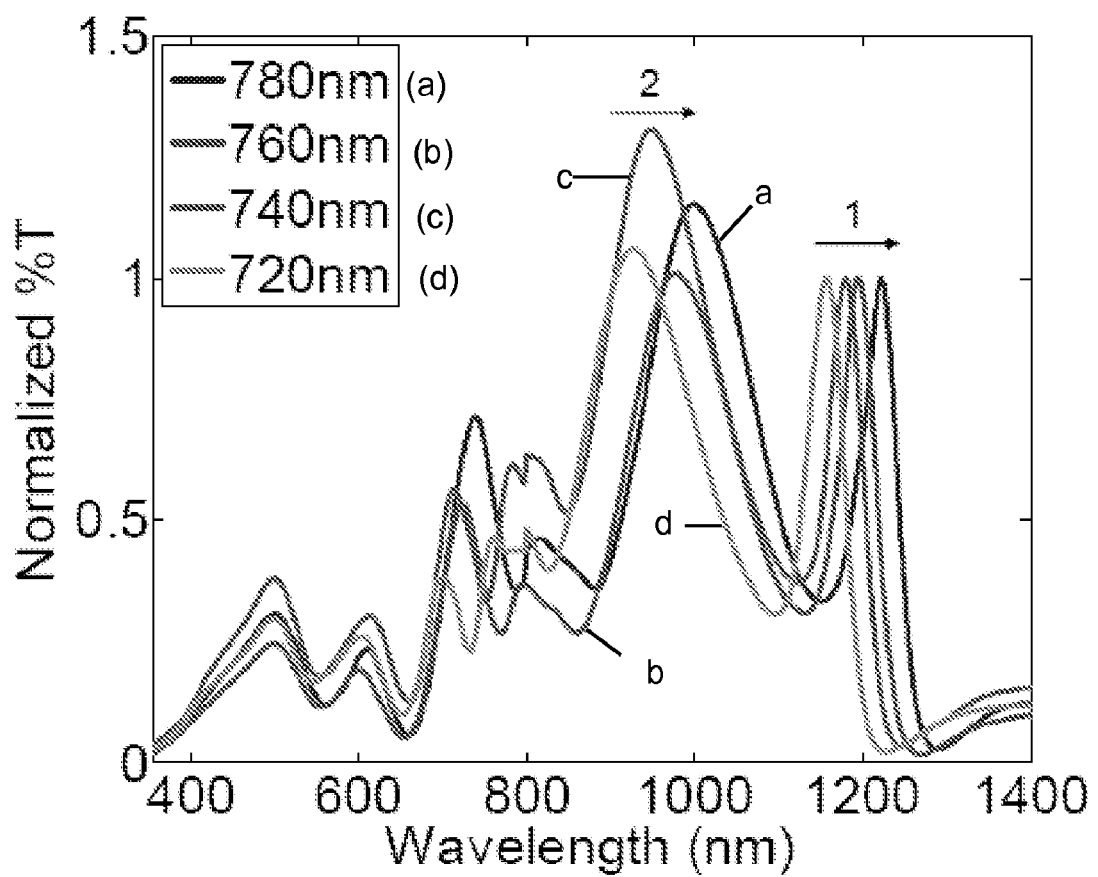
FIG. 21 provides transmission spectra for plasmonic crystals having constant depth holes and different periods ranging from 720 nm to 780 nm.

FIG. 21 provides transmission spectra for plasmonic crystals having constant depth holes and different periods ranging from 720 nm to 780 nm. As shown in FIG. 21, the spectra is observed to shift to higher wavelengths for plasmonic crystals having larger periods.

Figure 22:
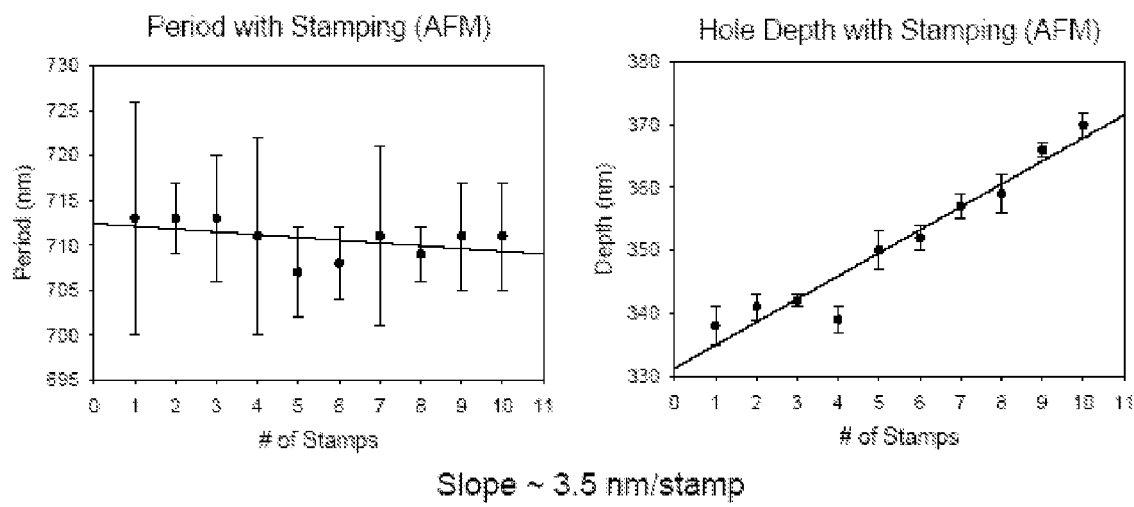
FIG. 22 provides depth and periods for sequentially stamped plasmonic crystals determined via atomic force microscopy.
Figure 23:
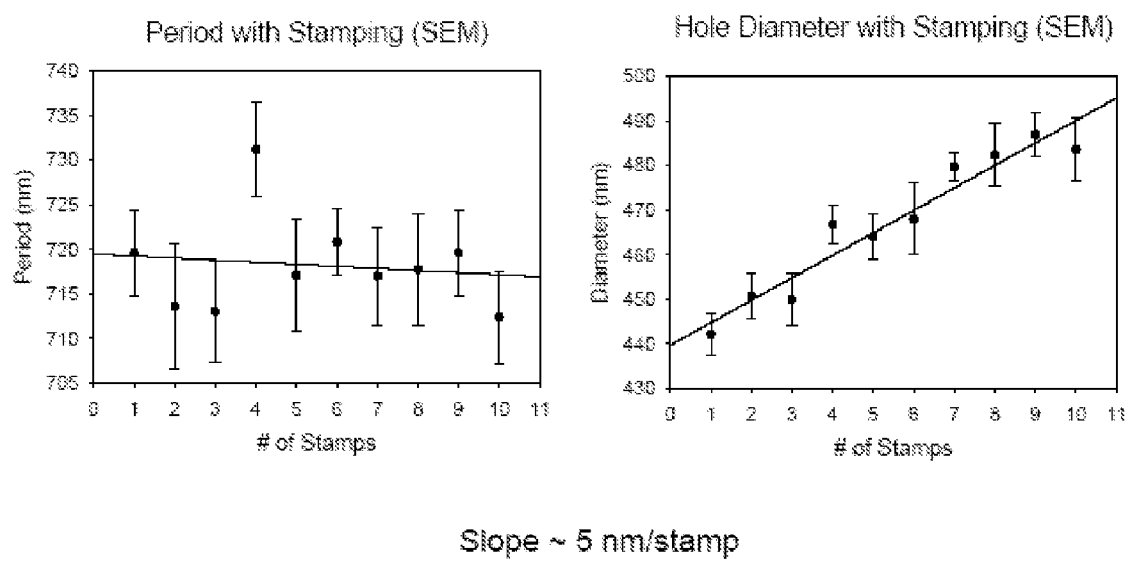
FIG. 23 provides depth and periods for sequentially stamped plasmonic crystals determined via Scanning electron microscopy.

FIG. 22 provides depth and periods for sequentially stamped plasmonic crystals determined via atomic force microscopy. As shown in FIG. 21 the depth of the holes increase systematically as the stamp is reused sequentially. FIG. 23 provides depth and periods for sequentially stamped plasmonic crystals determined via Scanning electron microscopy. As shown in FIG. 23 the diameter of the holes increase systematically as the stamp is reused sequentially.

Figure 24:
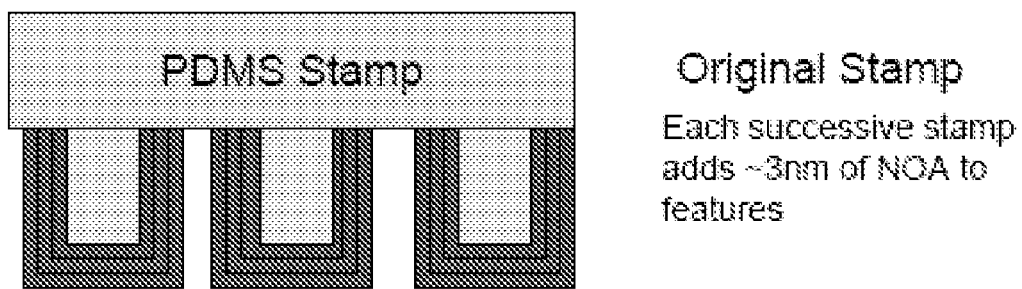
FIG. 24 shows a schematic illustrating that relief features of the stamp increase in vertical and longitudinal dimensions upon successive stamping due to accumulation of material on the features of the stamp.

FIG. 24 shows a schematic illustrating that relief features of the stamp increase in vertical and longitudinal dimensions upon successive stamping due to accumulation of material on the master features of the stamp. This aspect of the imprinting based fabrication platform is beneficial for providing selective adjustment of the physical dimensions of master relief features of master stamps used in the present methods. For example, fine tuning provided by accumulation of material on stamp features upon successive stamping protocols allows for deterministic definition and accurate selection of the geometries and physical dimensions of multilayer three-dimensional plasmonic crystals useful for SPR sensing and imaging applications.

Example 5

Plasmonic Crystals and SPR Sensors Having a Continuous Thin Film Configuration The present invention includes plasmonic crystals and SPR Sensors having a continuous thin film configuration, for example provided in a three-dimensional plasmonic crystal configuration. In these embodiments, a continuous metallic or semiconductor film is provided on an external surface of a nanostructured dielectric substrate, for example a dielectric substrate having an array of recessed and/or relief features. In embodiments useful for SPR sensing applications requiring high sensitivity or high resolution imaging capabilities, a continuous metallic film is provided such that it conformally covers an external surface of a nanostructured dielectric substrate, including conformally covering recessed and/or relief features of the substrate.

Plasmonic crystals formed by sputter deposition of a continuous gold film have several benefits over their quasi-3D counterparts. In the context of this Example, plasmonic crystals having a continuous thin film configuration are referred to as three-dimensional plasmonic crystals, wherein plasmonic crystals comprising a discontinuous multilayer configuration are referred to as quasi three dimensional plasmonic crystals. One key aspect that is important for process scale-up and mass production is that the fabrication protocol of the sputtered crystals is much less demanding than for the quasi-3D crystals. The sidewall profiles of the embossed nanoholes can be perfectly straight, undercut, or overcut, yet still provide a responsive crystal since sputter deposition covers the sidewalls of the nanoholes with gold. This is not necessarily the case for the quasi-3D crystals which require an undercut sidewall profile to physically block (shadow) the deposition of gold onto the sidewalls of the nanoholes during electron beam evaporation of gold.

Further, Quasi-3D crystals exhibit high sensitivity in the near-infrared (NIR) region of the electromagnetic spectrum, which requires the use of relatively expensive NIR cameras for imaging of binding events at the surface of the crystals. In contrast, a plasmonic crystal sensors having a sputtered continuous metallic film exhibit larger visible wavelength responses to changes in refractive index than the quasi-3D crystals. This high visible wavelength sensitivity is important for the development of inexpensive detection systems for monitoring binding events, because it allows for the use of silicon CCD cameras, which are less expensive than the NIR cameras required for use with the quasi-3D crystals. The sputtered crystals also exhibit a larger integrated response to refractive index changes (larger sensitivity/figure of merit), which allow for lower detection limits.

To demonstrate the performance capabilities of three dimensional plasmonic crystals and SPR sensors having a continuous film configuration, the sensitivities and imaging capabilities of SPR sensors comprising a continuous metallic layer in provided in conformal contact with a nanostructure dielectric substrate having a plurality of recessed features were evaluated.

Figure 25:
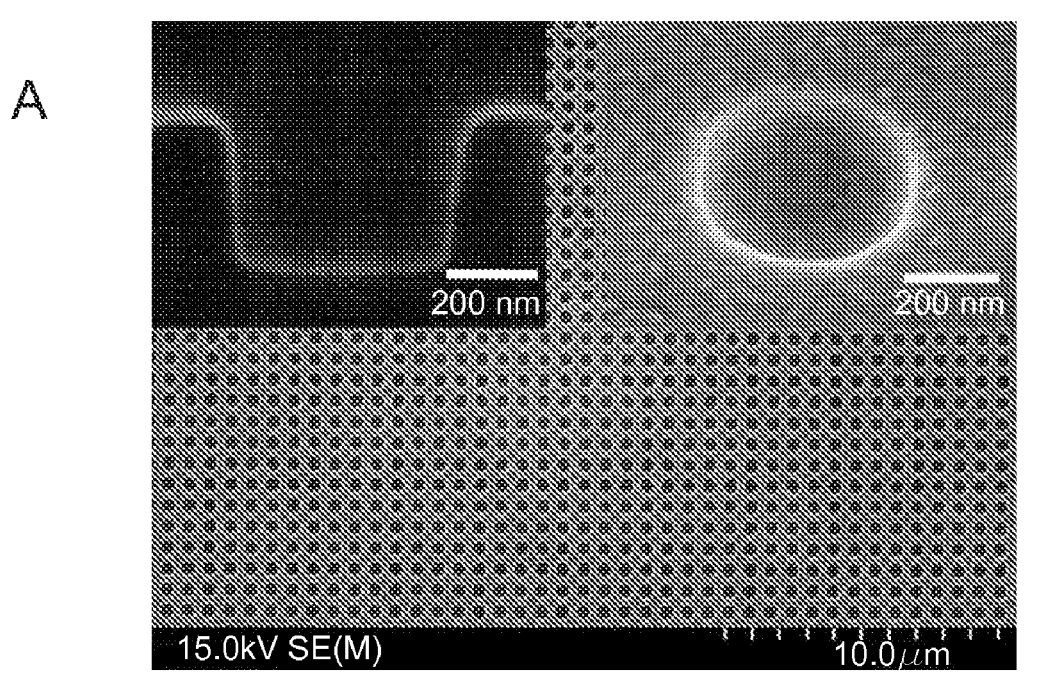
FIG. 25 (A) Scanning electron micrograph (SEM) of a crystal (Left Inset) A high magnification SEM that shows the cross-section structure of a nanohole; (Right Inset) tilted SEM showing the continuous gold coating. (B) Correlation of transmission spectral features with nanohole plasmonic excitations. (A) Normal incidence transmission spectrum of sputter coated plasmonic crystal (red) and rigorous electrodynamics modeling of the spectrum for the crystal (black).
Figure 25:
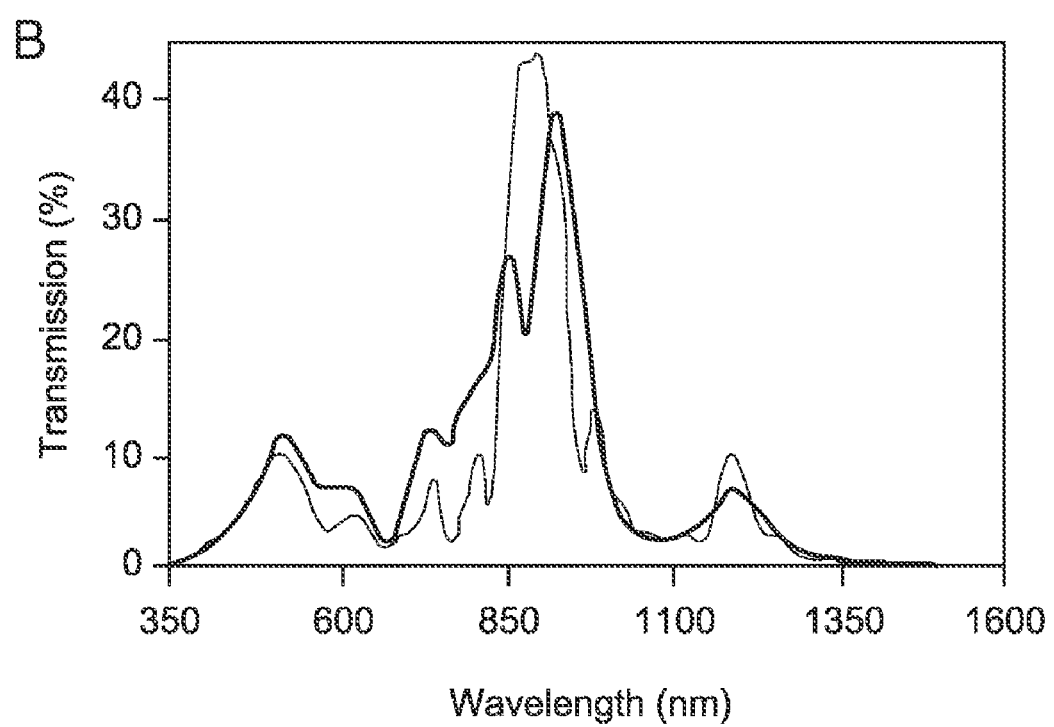

FIG. 25A (Bottom Inset) provides a scanning electron micrograph (SEM) of a plasmonic crystal of the present Example having a continuous film configuration wherein a thin metallic film is provided in conformal contact with a nanostructured dielectric substrate having an periodic array of recessed features comprising nanoholes. FIG. 25A (Top Left Inset) provides a high magnification SEM that shows the cross-section structure of a nanohole of the plasmonic crystal. FIG. 25A (Top right Inset), also provides tilted SEM showing the continuous gold coating on the nanostructured dielectric substrate. FIG. 25B provides correlation of transmission spectral features with nanohole plasmonic excitations and normal incidence transmission spectrum of sputter coated plasmonic crystal (red) and rigorous electrodynamics modeling of the spectrum for the crystal (black).

The optical properties of a plasmonic crystal of this Example can be tuned by changing the metal deposition process. We have shown that quasi-3D plasmonic crystals can be formed using electron beam evaporation to deposit gold on a polymeric surface embossed with a square array of cylindrical wells, and that these devices exhibit high optical sensitivity in the near-infrared region of the electromagnetic spectrum. The geometry of the gold layer, and thus the optical properties of the plasmonic crystal, can be changed by using a different metal deposition process. For example, a continuous gold film can be formed on a nanostructured polymeric surface using sputter deposition (left figure). This geometry exhibits an optical response that is different from the quasi-3D crystal in that the peak due to disk-hole coupling is no longer present, but a strong peak corresponding to a localized plasmonic mode becomes dominant. These crystals exhibit high optical sensitivity in the visible region of the electromagnetic spectrum and also exhibit a greater sensitivity (larger integrated figure or merit (FOM)) than the quasi-3D crystals, as will be shown in the following Figures. Three dimensional finite difference time domain calculations can be performed to quantitatively model the optical response of these crystals. The figure on the right shows the experimental (red) and theoretical (black) optical response of a sputter coated plasmonic crystal under normal incidence illumination. Accurate measurements of the metal thickness at the top, sidewalls, and bottom of the nanowells must be included in the theoretical model in order to quantitatively model the experimental spectrum.

Figure 26:
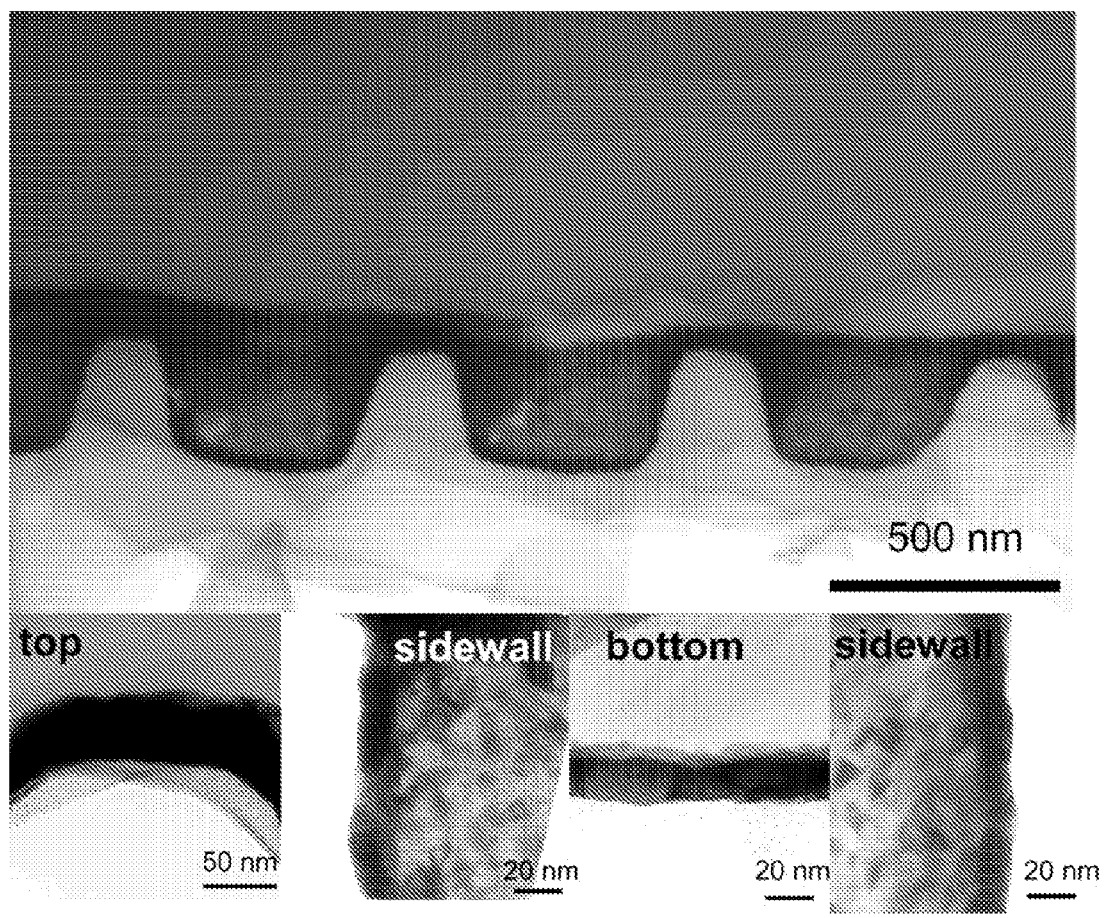
FIG. 26 High resolution TEM cross-sectional images showing the thickness of the sputter-deposited gold on a plasmonic crystal. The sputter deposition process results in different gold thicknesses on the top of the crystal (~40 nm) and on the sidewalls (~10-15 nm) and bottom (~20 nm) of the nanowells. These thicknesses are being used to develop computational models to accurately capture all of the features in the experimental spectra using finite difference time domain calculations.

FIG. 26 provides high resolution TEM cross-sectional images showing the thickness of the sputter-deposited gold on a plasmonic crystal. The sputter deposition process results in different gold thicknesses on the top of the crystal (~40 nm) and on the sidewalls (~10-15 nm) and bottom (~20 nm) of the nanowells. These thicknesses are being used to develop computational models to accurately capture all of the features in the experimental spectra using finite difference time domain calculations.

Figure 27:
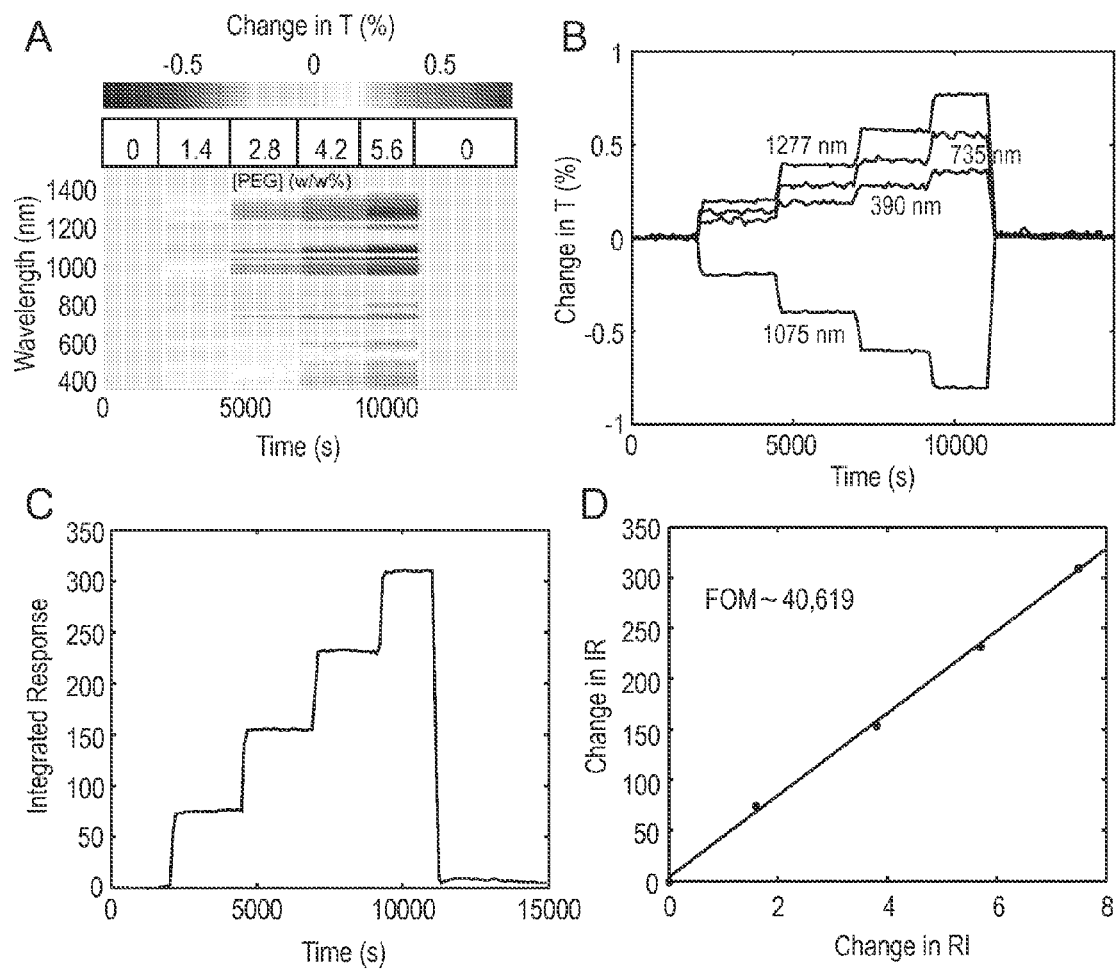
FIG. 27 Optical response of a plasmonic crystal to sequential injections of increasing concentrations of PEG water solutions. (A) Color contour plot of the change in transmission (T) as a function of wavelength and time (with the corresponding injection sequence overlaid on the plot) (B) Change in T as a function of time during the injection sequence, evaluated at several wavelengths. (C) Integrated multispectral plasmonic response as a function of time, (D) A linear correlation between integrated response and the change in refractive index.

FIG. 27 provides optical response of a plasmonic crystal to sequential injections of increasing concentrations of PEG water solutions. (A) Color contour plot of the change in transmission (T) as a function of wavelength and time (with the corresponding injection sequence overlaid on the plot) (B) Change in T as a function of time during the injection sequence, evaluated at several wavelengths. (C) Integrated multispectral plasmonic response as a function of time, (D) A linear correlation between integrated response and the change in refractive index.

Normal incidence transmission spectra were collected as a function of time with a temporal resolution of ~90 s as solutions of increasing concentration of poly(ethylene glycol) (PEG) were injected into a flow cell containing a plasmonic crystal with a 35 nm conformal sputter deposited gold layer.

A tin oxide adhesion layer was sputter deposited on the surface of the nanostructured polymer prior to gold deposition. This adhesion layer was found to improve the stability of the sensor in water and eliminated the drift of the sensor response as a function of time.

A difference plot (FIG. 27A) was constructed by subtracting the initial spectrum from all subsequent spectra. This plot illustrates that the plasmonic crystals formed by sputter deposition of gold show greater sensitivity in the visible region of the electromagnetic spectrum than the quasi-3D plasmonic crystals formed by electron beam evaporation of gold. The visible wavelength sensitivity, together with the high levels of spatial uniformity of the crystals, provide an important foundation for the analytical imaging of large area multiplexed bioassays using inexpensive CCD cameras rather than the NIR cameras required for the quasi-3D geometry. The ability to image self-assembled monolayers patterned on these crystals is demonstrated herein.

Additionally, the integrated bulk refractive index sensitivity of the sputter coated plasmonic crystal (figure of merit (FOM) ~41,000 D % T*nm/RIU) is about two times greater than that measured for the quasi-3D plasmonic crystals (FOM ~22,000 D % T*nm/RIU). Where D % T is the change in % T and RIU is a change in 1 of the refractive index (i.e. a 'refractive index unit').

Figure 28:
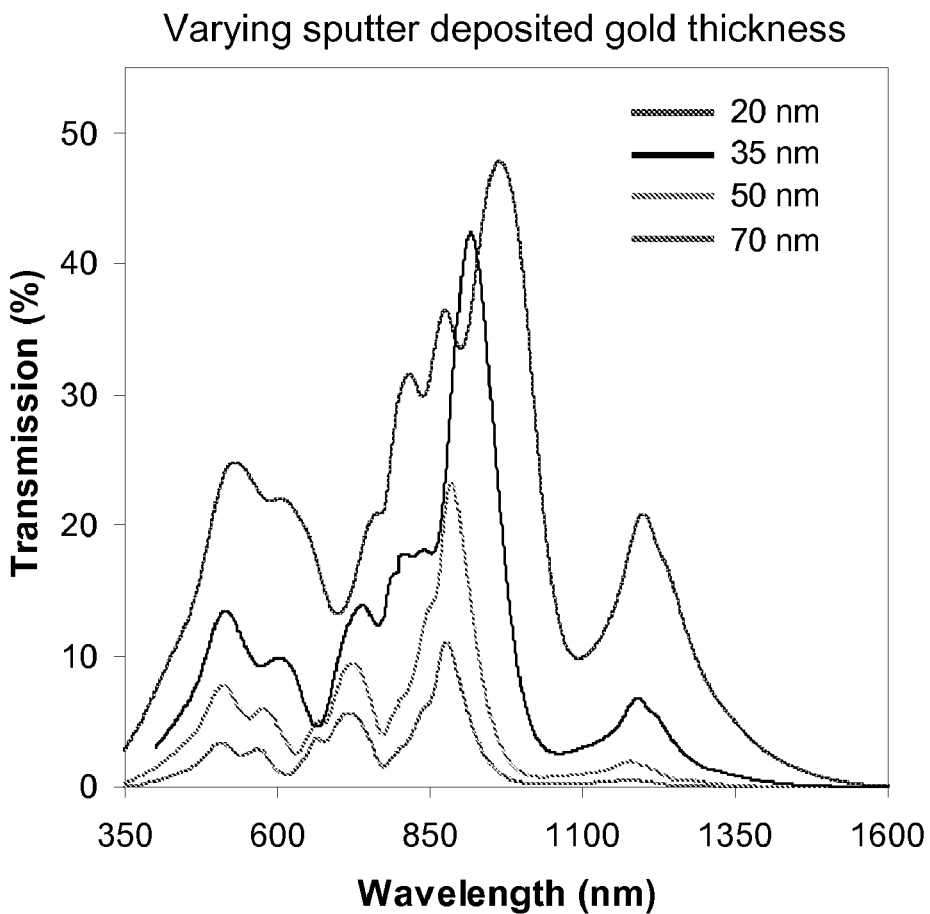
FIG. 28 provides transmission spectra illustrating that the nominal thickness of the sputter deposited gold also strongly affects the spectra and sensitivity (FOM) of the plasmonic crystals. In these experiments films were deposited using e-beam deposition techniques. In the sensitivity comparison data shown, the 350 nm depth features had side walls that were at least partially coated with a deposited film and the 500 nm depth features had side walls that were not coated with a deposited film.

FIG. 28 provides transmission spectra illustrating that the nominal thickness of the sputter deposited gold also strongly affects the spectra and sensitivity (FOM) of the plasmonic crystals. In these experiments films were deposited using e-beam deposition techniques. In the sensitivity comparison data shown, the 350 nm depth features had side walls that were at least partially coated with a deposited film and the 500 nm depth features had side walls that were not coated with a deposited film. These results show that the peaks blue shift, become narrower, and decrease in intensity as the nominal thickness of the deposited gold layer is increased. The blueshift is thought to arise from the decreasing diameter of the nanoholes as the gold thickness is increased. A systematic study of the integrated bulk refractive index sensitivity of plasmonic crystals with varying gold thickness showed that a thickness of ~35 nm yields crystals with the greatest sensitivity.

Figure 29:
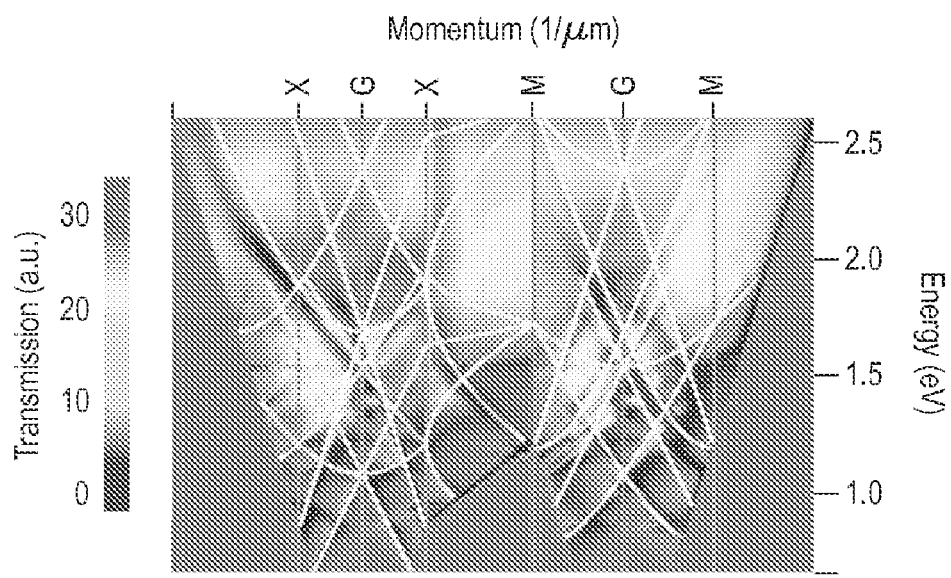
FIG. 29 (A) Plasmonic Brillouin zones of the sputter coated plasmonic crystal. (B) absolute values of the sensitivity map of ODT SAMs on crystal surface.
Figure 29:
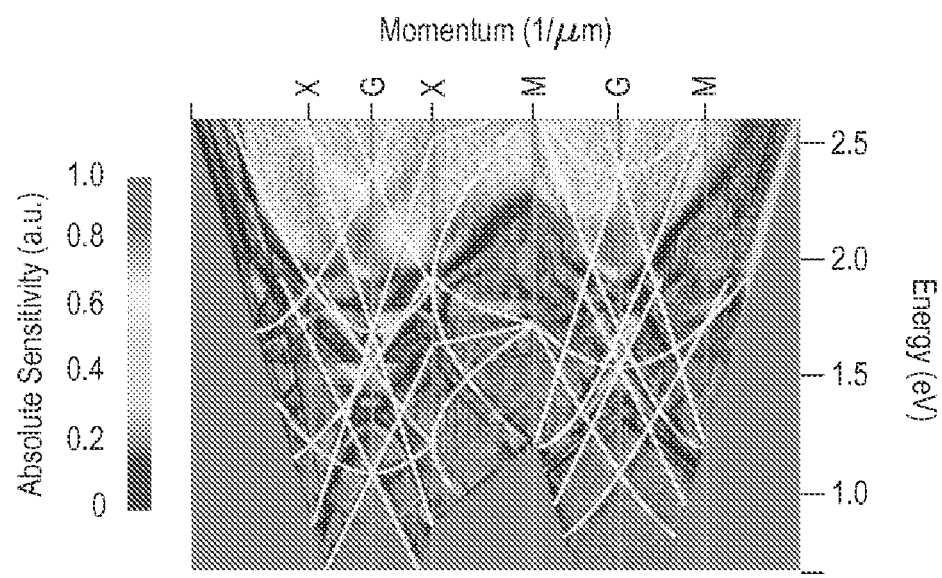

FIG. 29A provides Plasmonic Brillouin zones of the sputter coated plasmonic crystal and 29B) absolute values of the sensitivity map of ODT self assembled monolayers (SAMs) on the crystal surface This plot shows the normal dispersion curves for propagating surface plasmon polariton modes (SPPs) on the substrate/metal interface (Yellow lines) and the air/metal interface (white lines). The red lines indicate the critical points in Brillouin zone.

The sputter coated plasmonic crystal was dominated by localized modes (red peaks in brillouin zone maps). There are strong responses in the visible range of the electromagnetic spectrum due to the high energy dominated modes.

This is in contrast to the SPP mode dominated E-beam coated quasi-3D plasmonic crystals, where there are strong responses in the near infrared range of the electromagnetic spectrum due to the dominant low energy modes.

Full angle-dependent absolute sensitivity mapping of octadecanethiol SAMs shows the sensitivity of the crystal to surface chemical binding events. We can observed strong plasmonic responses in visible range, which correspond to the dominant high energy modes.

Figure 30:
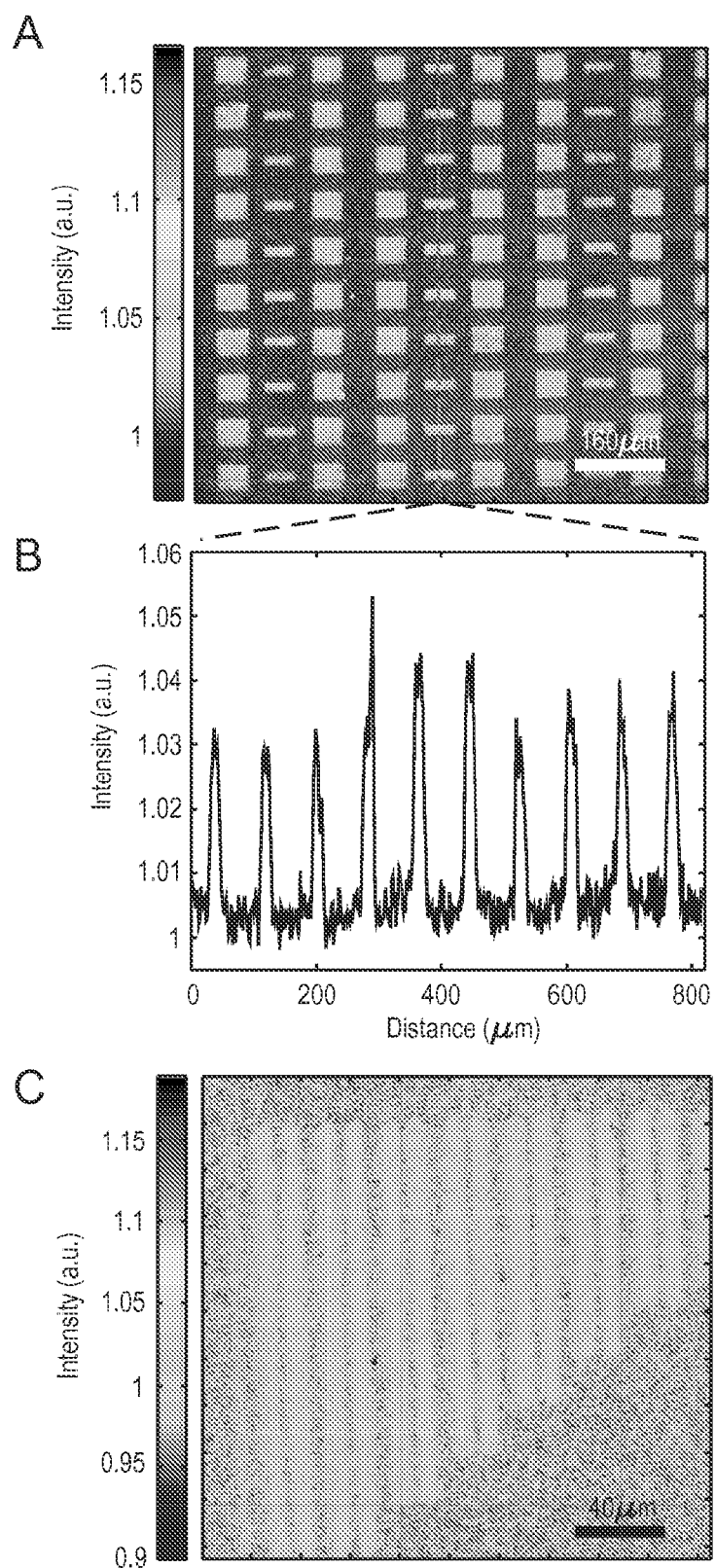
FIG. 30 Transmission-mode images of microcontact printed (µCP) 1-octadecanethiol (ODT) monolayers on a plasmonic crystal: (a) an array of squares and rectangles imaged using a 10× objective; (b) vertical slice through the image in (a); and (c) parallel lines imaged with a 40× objective.

Patterned octadecanethiol self-assembled monolayers (SAMs) were formed on the surface of a sputtered plasmonic crystal by microcontact printing. These SAMs have a thickness of approximately 20+/−2 Å. Normal incidence transmission mode images of the patterned SAMs were captured using commercially available microscope coupled to a Si CCD camera and white light. FIG. 30 provides transmission-mode images of microcontact printed (μCP) 1-octadecanethiol (ODT) monolayers on a plasmonic crystal: (a) an array of squares and rectangles imaged using a 10× objective; (b) vertical slice through the image in (a); and (c) parallel lines imaged with a 40× objective. The top figure shows the ability to image SAMs patterned over a large area due to the high spatial uniformity of the crystals and the middle figure shows a line scan through this image. The bottom figure shows the ability to resolve features with high lateral resolution. This resolution is competitive with the tens of microns spatial resolution of highly optimized surface plasmon resonance imaging systems based on propagating surface plasmon polaritons.

Figure 31:
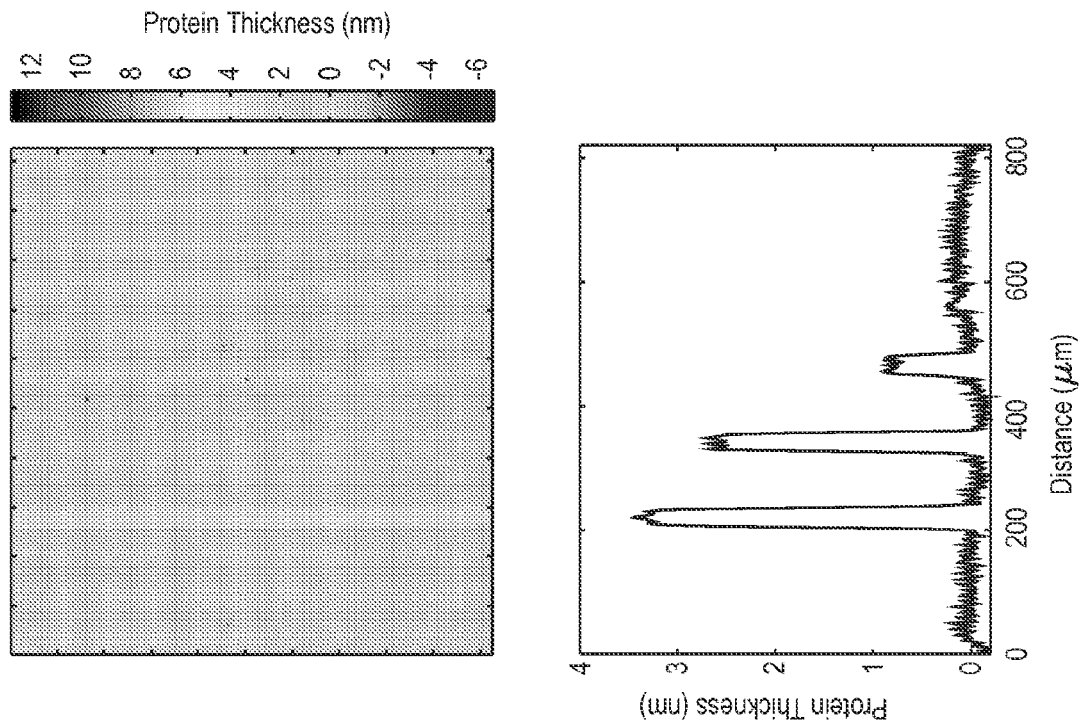
FIG. 31 provides a schematic describing an experiment showing that plasmonic crystal sensors of this example can discriminate between different molecular weight proteins and also provides images of proteins of varying molecular weight patterned on a plasmonic crystal using a microfluidic device. The channels were filled with protein solutions (0.1 mg/ml) for 1 hour and then rinsed three times with phosphate buffered saline. The surface of the crystal was then dried under a stream of nitrogen and imaged using a microscope and Si CCD camera. This figure shows that variations in the thickness of the nonspecifically adsorbed protein films—due to differences in the molecular weight of the proteins—can be measured using our system. Additionally, the optical response to the model system of SAMs in FIG. 30 was used as a calibration factor to determine the thickness of the protein films. The calculated protein thicknesses agreed well with experimentally determined protein thicknesses measured on flat gold substrates by ellipsometry. The line profile at the bottom right hand corner of the Figure was calculated by averaging the response over the entire image above.
Figure 31:
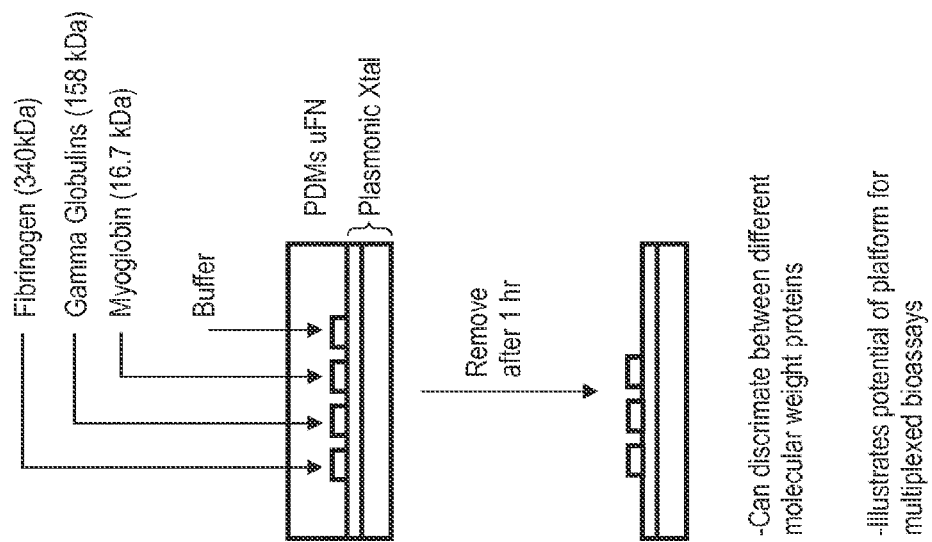

FIG. 31 provides a schematic describing an experiment showing that plasmonic crystal sensors of this example can discriminate between different molecular weight proteins and also provides images of proteins of varying molecular weight patterned on a plasmonic crystal using a microfluidic device. The channels were filled with protein solutions (0.1 mg/ml) for 1 hour and then rinsed three times with phosphate buffered saline. The surface of the crystal was then dried under a stream of nitrogen and imaged using a microscope and Si CCD camera. This figure shows that variations in the thickness of the nonspecifically adsorbed protein films—due to differences in the molecular weight of the proteins—can be measured using our system. Additionally, the optical response to the model system of SAMs in FIG. 30 was used as a calibration factor to determine the thickness of the protein films. The calculated protein thicknesses agreed well with experimentally determined protein thicknesses measured on flat gold substrates by ellipsometry. The line profile at the bottom right hand corner of FIG. 31 was calculated by averaging the response over the entire image above.

Figure 32:
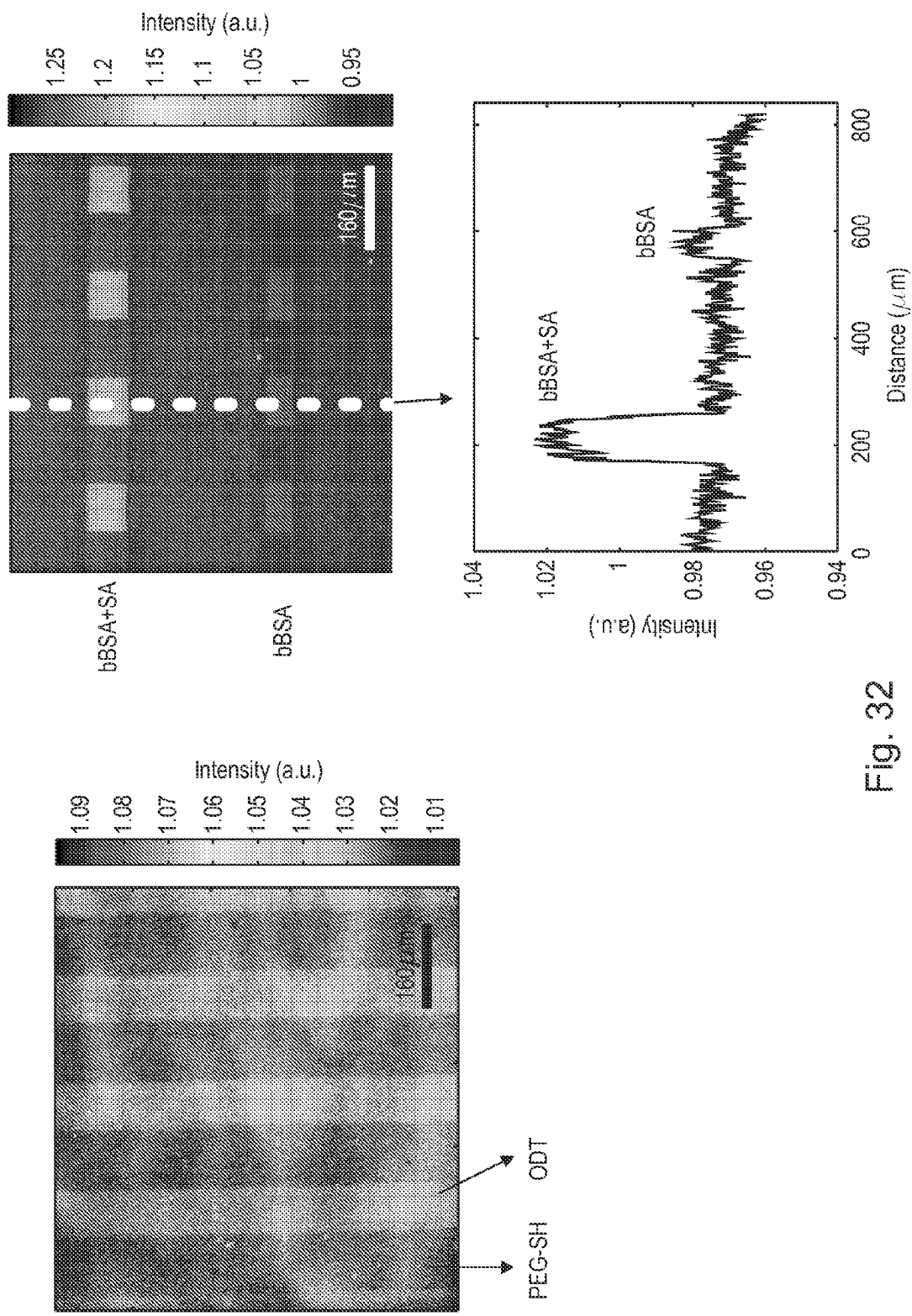
FIG. 32 provides plasmonic images of a model bioassay performed on a sputtered plasmonic crystal sensor. The surface of a plasmonic crystal was first patterned with lines of a hydrophobic SAM, octadecanethiol, by microcontact printing. The remaining areas of bare gold surface was functionalized with a SAM of a hexa-ethylene glycol terminated thiol. This provided a surface presenting alternating regions that support (octadecanethiol) and resist (hexa-ethylene glycol terminated thiol) nonspecific protein adsorption. A PDMS microfluidic device with straight, parallel channels was used to deliver protein solutions across the surface of the crystal in an orthogonal direction to the underlying patterned lines of SAMs. After protein delivery the channels were rinsed three times with buffer, then the channels were removed and the entire crystal was rinsed with water and dried under a stream of nitrogen. The plasmonic images of the SAM (left) and protein modified surfaces (right) are shown in FIG. 32. The acronyms in the Figure are: (i) hexa-ethylene glycol terminated thiol (PEG-SH); (ii) octadecanethiol (ODT); (iii) biotinylated bovine serum albumin (bBSA); and (iv) streptavidin (SA).

FIG. 32 provides plasmonic images of a model bioassay performed on a sputtered plasmonic crystal sensor. The surface of a plasmonic crystal was first patterned with lines of a hydrophobic SAM, octadecanethiol, by microcontact printing. The remaining areas of bare gold surface was functionalized with a SAM of a hexa-ethylene glycol terminated thiol. This provided a surface presenting alternating regions that support (octadecanethiol) and resist (hexa-ethylene glycol terminated thiol) nonspecific protein adsorption. A PDMS microfluidic device with straight, parallel channels was used to deliver protein solutions across the surface of the crystal in an orthogonal direction to the underlying patterned lines of SAMs. After protein delivery the channels were rinsed three times with buffer, then the channels were removed and the entire crystal was rinsed with water and dried under a stream of nitrogen. The plasmonic images of the SAM (left) and protein modified surfaces (right) are shown in the FIG. 32. The acronyms in this Figure are: (i) hexa-ethylene glycol terminated thiol (PEG-SH); (ii) octadecanethiol (ODT); (iii) biotinylated bovine serum albumin (bBSA); and (iv) streptavidin (SA).

Figure 33:
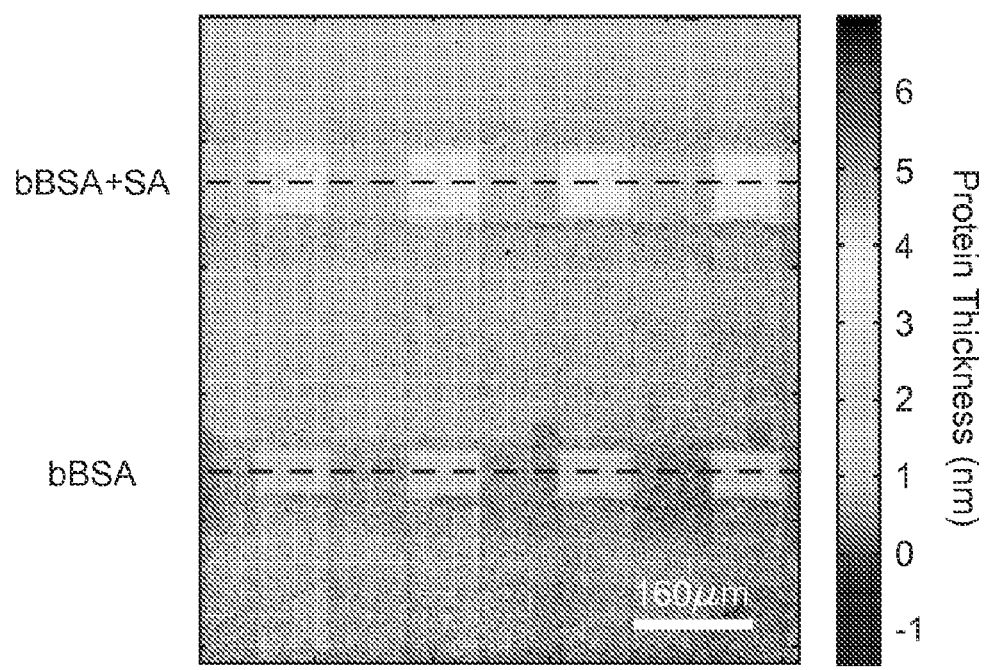
FIG. 33 The response of the crystal to the model SAM layer of ODT shown in FIG. 30 was used as a calibration factor to calculate the thickness of the bBSA and bBSA+SA spots in the 2D bioassay. The figure on the left shows a 2D plasmonic image of the microarray and the figure on the right shows line scans through several of the spots in the microarray. Both plots show the corresponding calibrated protein thicknesses. There is a slight drift in the background intensity in the 2D array (a gradient of intensity that is stronger at the top and weaker at the bottom). This uneven background is caused by the shape of the source filament (a tungsten-halogen bulb) and optics in the microscope. We are currently developing an algorithm for removing this uneven background intensity distribution. The present algorithm works well but does not provide a completely flat background.
Figure 33:
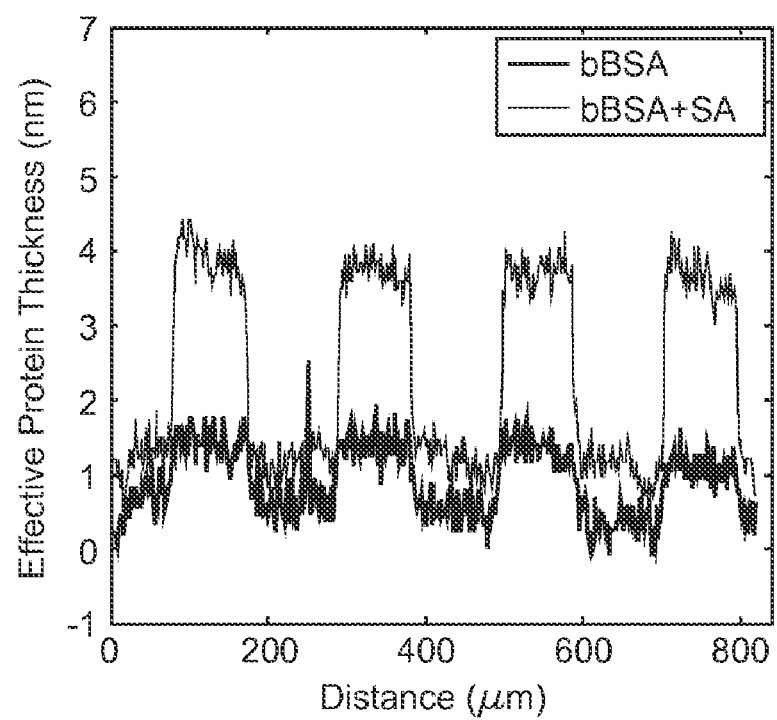

FIG. 33 provides images and SPR response data showing the response of the crystal to the model SAM layer of ODT shown in FIG. 30 was used as a calibration factor to calculate the thickness of the bBSA and bBSA+SA spots in the 2D bioassay. The figure on the left shows a 2D plasmonic image of the microarray and the figure on the right shows line scans through several of the spots in the microarray. Both plots show the corresponding calibrated protein thicknesses. There is a slight drift in the background intensity in the 2D array (a gradient of intensity that is stronger at the top and weaker at the bottom). This uneven background is caused by the shape of the source filament (a tungsten-halogen bulb) and optics in the microscope. We are currently developing an algorithm for removing this uneven background intensity distribution. The present algorithm works well but does not provide a completely flat background.

Figure 34:
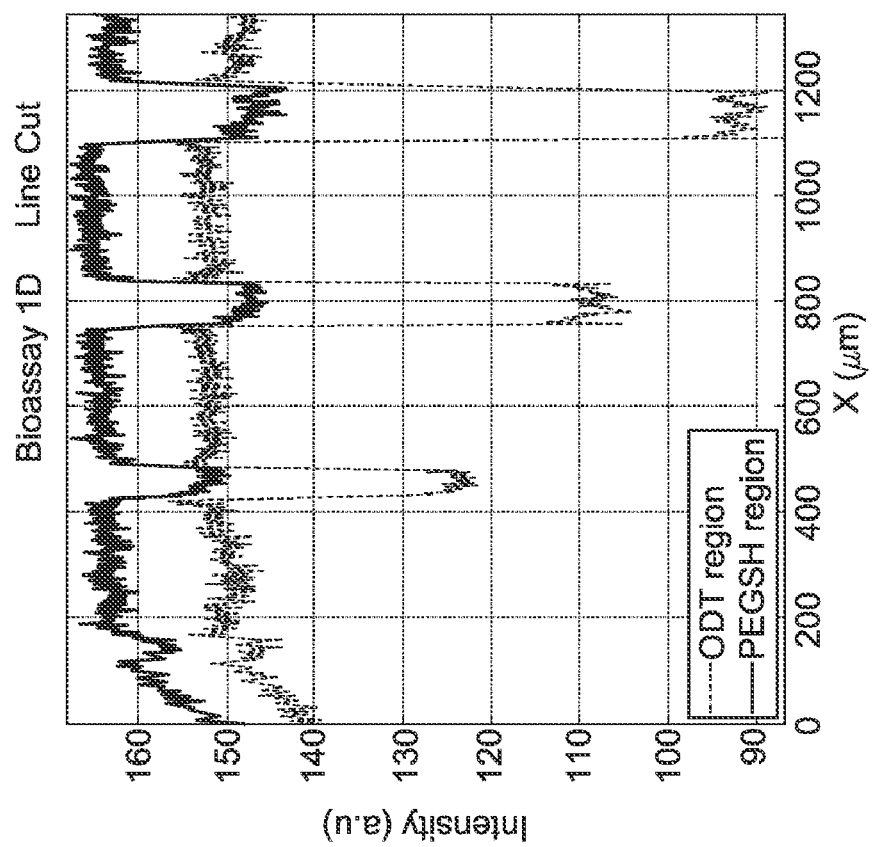
FIG. 34 (A) SEM image shows 2D bioassay on thiol modified crystal surface. (B) The line profiles across PDMS microfluidic channels on ODT and PEGSH regions display different gray intensities corresponding to specific protein bindings.
Figure 34:
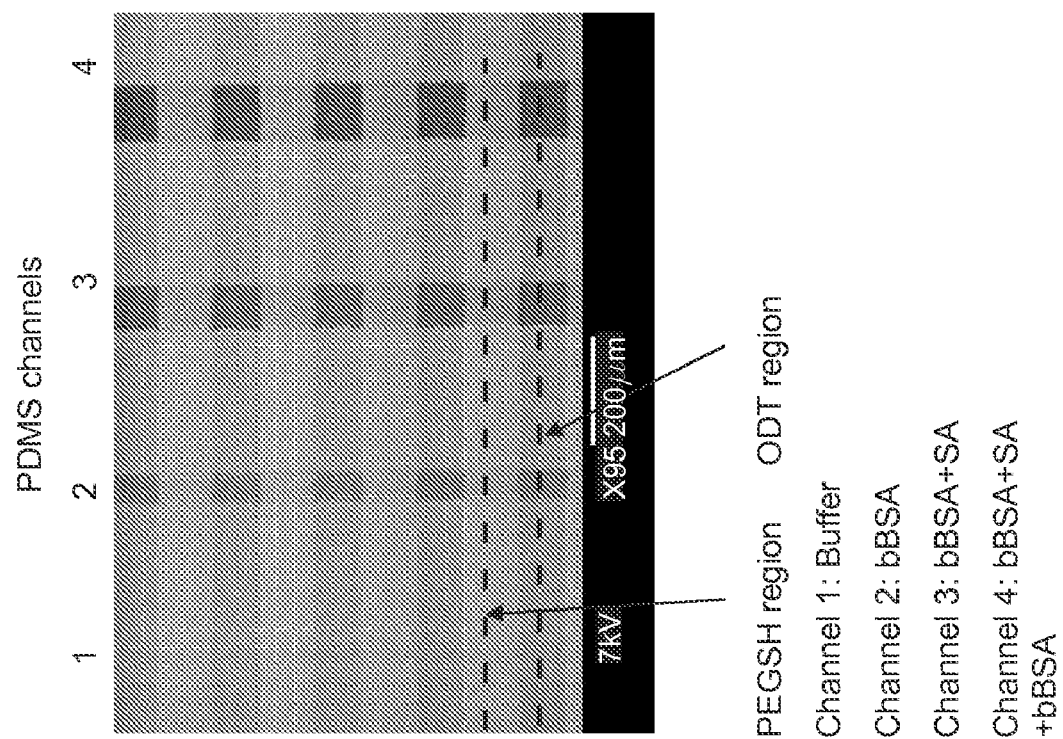

FIG. 34 provides a SEM image of the 2D bioassay on thiol functionalized sputter coated plasmonic crystal demonstrates the difference in intensity between specific and nonspecific protein binding. The line profile across the protein adsorption region and the inert PEG-thiol region shows contrast differences due to the selective binding reactions of proteins. The gray intensities of the spots in the bioassay increase with increasing mass coverage. The weak contrast difference in the PEG-thiol region was caused by a small degree of nonspecific adsorption since the PEG-thiol does not completely block protein adsorption.

Statements Regarding Incorporation by Reference and Variations

The follow in references relate generally to imprint based patterning and lithography techniques and are hereby incorporated by reference in their entireties: (1) Chou, S., "Nanoimprint Lithography and Lithographically Induced Self-Assembly," MRS Bulletin, July 2001, 512-517; (2) Braeuer, A., Dannberg, P., Mann, G., and Popall, M., "Precise Polymer Micro-Optical Systems," MRS Bulletin, July 2001, 519-522; (3) Rogers, J. A., and Nuzzo, R. G., "Recent progress in soft lithography," Materials Today, February 2005, 50-56; (4) Zaumseil, J., Meitl, M. A., Hsu, Julia W. P., Acharya, B. R., Baldwin, K. W., Loo, Y., and Rogers, J. A., "Three-Dimensional and Multilayer Nanostructures Formed by Nanotransfer Printing," Nano Letters, 2003, Vol. 3, No. 9, 1223-1227 and (5) Xia, Y., Rogers, J. A., Paul, K. E., and Whitesides, G. M., "Unconventional Methods for Fabricating and Patterning Nanostructures," Chem. Rev. 1999, 99, 1823-1848.

The following references relate generally to SPR sensing systems and methods and are hereby incorporated by reference in their entireties: (1) Liu, Y., Bishop, J., Williams, L., Blair, S, and Herron, J., "Biosensing based upon molecular confinement in metallic nanocavity arrays," Nanotechnology 2004, 15, 1368-1374; (2) Williams, S. M., Rodriguez, K. R., Teeters-Kennedy, S., Stafford, A. D., Bishop, S. R., Lincoln, U. K., and Coe, J. V., "Use of the Extraordinary Infrared Transmission of Metallic Subwavelength Arrays to Study the Catalyzed Reaction of Methanol to Formaldehyde on Copper Oxide," J. Phys. Chem. B 2004, 108, 11833-11837; (3) Dahlin, A. B., Tegenfeldt, J. O., and Höök, F., "Improving the Instrumental Resolution of Sensors Based on Localized Surface Plasmon Resonance," Anal. Chem. 2006, 78, 4416-4423; (4) Brolo, A. G., Gordon, R., Leathem, B., and Kavanagh, K. L., "Surface Plasmon Sensor Based on the Enhanced Light Transmission through Arrays of Nanoholes in Gold Films," Langmuir 2004, 20, 4813-4815; (5) Rindzevicius, T., Alayerdyan, Y., Dahlin, A., Höök, F., Sutherland, D. S., and Kall, M., "Plasmonic Sensing Characteristics of Single Nanometric Holes," Nano Letters, 2005, Vol. 5, No. 11, 2335-2339; (6) Tetz, K. A., Pang, L., and Fainman, Y., "High-resolution surface Plasmon resonance sensor based on linewidth-optimized nanohole array transmittance," Optics Letters, 2006, Vol. 31, No. 10, 1528-1530; (6) Dintinger, J., Klein, S., and Ebbesen, T., "Molecule-Surface Plasmon Interactions in Hole Arrays: Enhanced Absorption, Refractive Index Changes, and All-Optical Switching," Adv. Mater. 2006, 18, 1267-1270; (7) Malyarchuk, V., Hua, F., Mack, N. H., Velasquez, V. T., White, J. O., Nuzzo, R. G., and Rogers, J. A., "High performance plasmonic crystal sensor formed by soft nanoimprint lithography," Optics Express 2005, Vol. 13, No. 15, 5669-5675.

All references throughout this application, for example patent documents including issued or granted patents or equivalents; patent application publications; unpublished patent applications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Any appendix or appendices hereto are incorporated by reference as part of the specification and/or drawings.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. Separate embodiments of the invention are also intended to be encompassed wherein the terms "comprising" or "comprise(s)" or "comprised" are optionally replaced with the terms, analogous in grammar, e.g.; "consisting/consist(s)" or "consisting essentially of/consist(s) essentially of" to thereby describe further embodiments that are not necessarily coextensive.

The invention has been described with reference to various specific and preferred embodiments and techniques. However, it should be understood that many variations and modifications may be made while remaining within the spirit and scope of the invention. It will be apparent to one of ordinary skill in the art that compositions, methods, devices, device elements, materials, procedures and techniques other than those specifically described herein can be applied to the practice of the invention as broadly disclosed herein without resort to undue experimentation. All art-known functional equivalents of compositions, methods, devices, device elements, materials, procedures and techniques described herein are intended to be encompassed by this invention. Whenever a range is disclosed, all subranges and individual values are intended to be encompassed as if separately set forth. This invention is not to be limited by the embodiments disclosed, including any shown in the drawings or exemplified in the specification, which are given by way of example or illustration and not of limitation. The scope of the invention shall be limited only by the claims.

REFERENCES

Diamond, D., Principles of Chemical and Biological Sensors. Wiley: New York, 1998; Vol. 150, p. 368.
Homola, J.; Yee, S. S.; Gauglitz, G., Sensors and Actuators, B: Chemical 1999, B54, 3-15.
Raether, H., Surface Plasmons on Smooth and Rough Surfaces and on Gratings. Springer-Verlag: New York, 1988; Vol. 111, p. 136.
Brolo, A. G.; Gordon, R.; Leathem, B.; Kavanagh, K. L., Langmuir 2004, 20, 4813-4815.
Chou, S. Y., MRS Bulletin 2001, 26, 512-517.
Chou, S. Y.; Krauss, P. R.; Renstrom, P. J., Science (Washington, D.C.) 1996, 272, 85-7.
Gates, B. D., Materials Today (Oxford, United Kingdom) 2005, 8, 44-49.
Loo, Y.-L.; Willett, R. L.; Baldwin, K. W.; Rogers, J. A., Applied Physics Letters 2002, 81, 562-564.
Loo, Y.-L; Willett, R. L.; Baldwin, K. W.; Rogers, J. A., Journal of the American Chemical Society 2002, 124, 7654-7655.
Resnick, D. J.; Sreenivasan, S. V.; Willson, C. G., Materials Today (Oxford, United Kingdom) 2005, 8, 34-42.
Rogers, J. A., MRS Bulletin 2001, 26, 530-534.
Rogers, J. A.; Nuzzo, R. G., Materials Today (Oxford, United Kingdom) 2005, 8, 50-56.
Bain, C. D.; Troughton, E. B.; Tao, Y. T.; Evall, J.; Whitesides, G. M.; Nuzzo, R. G., Journal of the American Chemical Society 1989, 111, 321-35.

Ebbesen, T. W.; Lezec, H. J.; Ghaemi, H. F.; Thio, T.; Wolff, P. A., *Nature (London)* 1998, 391, 667-669.
Altewischer, E.; van Exter, M. P.; Woerdman, J. P., *Nature* 2002, 418, 304-6.
Barnes, W. L.; Murray, W. A.; Dintinger, J.; Devaux, E.; Ebbesen, T. W., *Physical Review Letters* 2004, 92, 107401.
Devaux, E.; Ebbesen, T. W.; Weeber, J.-C.; Dereux, A., *Applied Physics Letters* 2003, 83, 4936-4938.
Hohng, S. C.; Yoon, Y. C.; Kim, D. S.; Malyarchuk, V.; Muller, R.; Lienau, C.; Park, J. W.; Yoo, K. H.; Kim, J.; Ryu, H. Y.; Park, Q. H., *Applied Physics Letters* 2002, 81, 3239-3241.
Kim, D. S.; Hohng, S. C.; Malyarchuk, V.; Yoon, Y. C.; Ahn, Y. H.; Yee, K. J.; Park, J. W.;
Kim, J.; Park, Q. H.; Lienau, C., *Physical Review Letters* 2003, 91, 143901/1-143901/4.
Hua, F.; Sun, Y.; Gaur, A.; Meitl, M. A.; Bilhaut, L.; Rotkina, L.; Wang, J.; Geil, P.; Shim, M.; Rogers, J. A.; Shim, A., *Nano Letters* 2004, 4, 2467-2471.
Ghaemi, H. F.; Thio, T.; Grupp, D. E.; Ebbesen, T. W.; Lezec, H. J., *Physical Review B: Condensed Matter and Materials Physics* 1998, 58, 6779-6782.
Johnson, P. B.; Christy, R. W., *Physical Review B: Solid State* 1972, 6, 4370-9.
Ropers, C.; Park, D. J.; Stibenz, G.; Steinmeyer, G.; Kim, J.; Kim, D. S.; Lienau, C., *Physical Review Letters* 2005, 94, 113901/1-113901/4.
Rich, R. L.; Myszka, D. G. *Trends Microbiol.* 2003, 11, 124.
Mozsolits, H.; Thomas, W. G.; Aguilar, M.-I. *J. Pept. Sci.* 2003, 9, 77.
Su, X.; Wu, Y.-J.; Robelek, R.; Knoll, W. *Langmuir* 2005, 21, 348.
Kyo, M.; Usui-Aoki, K.; Koga, H. *Anal. Chem.* 2005, 77, 7115.
Lin, L.; Harris, J. W.; Thompson, G. R.; Brody, J. P. *Anal. Chem.* 2004, 76, 6555.
Rich, R. L.; Myszka, D. G. *Drug Discovery Today: Technologies* 2004, 1, 301.
Homola, *J. Anal. Bioanal. Chem.* 2003, 377, 528.
Homola, J.; Yee, S. S.; Gauglitz, G. *Sensors and Actuators B* 1999, 54, 3.
Knoll, W. *Annu. Rev. Phys. Chem.* 1998, 49, 569.
Stuart, D. A.; Haes, A. J.; Yonzon, C. R.; Hicks, E. M.; Van Duyne, R. P. *IEE Proc. Nanobiotechnol.* 2005, 152, 13.
Hawtin, P.; Hardern, I.; Wittig, R.; Molenhauer, J.; Poustka, A.; Salowsky, R.; Wulff, T.; Rizzo, C.; Wilson, B. *Electrophoresis* 2005, 26, 3674.
Kato, M.; Gyoten, Y.; Sakai-Kato, K.; Nakajima, T.; Toyo'oka, T. *Electrophoresis* 2005, 26, 3682.
Breslauer, D. N.; Lee, P. J.; Lee, L. P. *Molecular BioSystems* 2006, 2, 97.
Cretich, M.; Damin, F.; Pirri, G.; Chiari, M. *BiomolecularEngineering* 2006, 23, 77.
Nath, N.; Chilkoti, A. *Anal. Chem.* 2002, 74, 504.
Haes, A. J.; Van Duyne, R. P. *J. Am. Chem. Soc.* 2002, 124, 10596.
Kalyuzhny, G.; Vaskevich, A.; Schneeweiss, M. A.; Rubinstein, I. *Chem. Eur J.* 2002, 8, 3849.
Ramachandran, N.; Larson, D. N.; Stark, P. R. H.; Hainsworth, E.; LaBaer, J. *FEBS Journal* 2005, 272, 5412.
Tomizaki, K.-Y.; Usui, K.; Mihara, H. *ChemBioChem* 2005, 6, 782.
Malinsky, M. D.; Kelly, K. L.; Schatz, G. C.; Van Duyne, R. P. *J. Am. Chem. Soc.* 2001, 123, 1471.
Ebbesen, T. W.; Lezec, H. J.; Ghaemi, H. F.; Thio, T.; Wolff, P. A. *Nature* 1998, 391, 667.
Ghaemi, H. F.; Thio, T.; Grupp, D. E.; Ebbesen, T. W.; Lezec, H. J. *Phys. Rev. B.* 1998, 58, 6779.
Raether, H. *Surface Plasmons on Smooth and Rough Surfaces and on Gratings*; Springer-Verlag: Berlin, 1988.
Brolo, A. G.; Kwok, S. C.; Moffitt, M. G.; Gordon, R.; Riordon, J.; Kavanagh, K. L. *J. Am. Chem. Soc.* 2005, 127, 14936.
Liu, Y.; Bishop, J.; Williams, L.; Blair, S.; Herron, J. *Nanotechnology* 2004, 15, 1368.
Barnes, W. L.; Dereux, A.; Ebbesen, T. W. *Nature* 2003, 424, 824.
Dintinger, J.; Klein, S.; Ebbesen, T. W. *Adv. Mater.* 2006, 18, 1267.
Hutter, E.; Fendler, J. H. *Adv. Mater.* 2004, 16, 1685.
Maier, S. A.; Atwater, H. A. *J. Appl. Phys.* 2005, 98, 011101 (1.
Chang, S.-H.; Gray, S. K.; Schatz, G. C. *Opt. Express* 2005, 13, 3150.
Murray, W. A.; Astilean, S.; Barnes, W. L. *Phys. Rev. B.* 2004, 69, 165407.
Lezec, H. J.; Thio, T. *Opt. Express* 2004, 12, 3629.
Gordon, R.; Brolo, A. G.; McKinnon, A.; Rajora, A.; Leathem, B.; Kavanagh, K. L. *Phys. Rev. Lett.* 2004, 92, 037401.
Prikulis, J.; Hanarp, P.; Olofsson, L.; Sutherland, D. S.; Kall, M. *Nano Lett.* 2004, 4, 1003.
Thio, T.; Lezec, H. J.; Ebbesen, T. W.; Pellerin, K. M.; Lewen, G. D.; Nahata, A.; Linke, R. A. *Nanotechnology* 2002, 13, 429.
Degiron, A.; Lezec, H. J.; Barnes, W. L.; Ebbesen, T. W. *Appl. Phys. Lett.* 2002, 81, 4327.
Kim, T. J.; Thio, T.; Ebbesen, T. W.; Grupp, D. E.; Lezec, H. J. *Opt. Lett.* 1999, 24, 256.
Brolo, A. G.; Gordon, R.; Leathem, B.; Kavanagh, K. L. *Langmuir* 2004, 20, 4813.
Srinivasan, V.; Pamula, V. K.; Fair, R. B. *Lab on a Chip* 2004, 4, 310.
Taflove, A.; Hagness, S. C. *Computational Electrodynamics: The Finite-Difference Time-Domain*; Third ed.; Artech House: Boston, 2005.
Malyarchuk, V.; Hua, F.; Mack, N. H.; Velasquez, V. T.; White, J. O.; Nuzzo, R. G.; Rogers, J. A. *Opt. Express* 2005, 13, 5669.
Rindzevicius, T.; Alayerdyan, Y.; Dahlin, A.; Hook, F.; Sutherland, D. S.; Kall, M. *Nano Lett.* 2005, 5, 2335.
Sun, Y.; Xia, Y. *The Analyst* 2003, 128, 686.
Haes, A. J.; Chang, L.; Klein, W. L.; Van Duyne, R. P. *J. Am. Chem. Soc.* 2005, 127, 2264.
Jung, L. S.; Campbell, C. T.; Chinowsky, T. M.; Mar, M. N.; Yee, S. S. *Langmuir* 1998, 14, 5636.
Wilchek, M.; Bayer, E. A. *Methods in Enzymology* 1990, 184, 5.
Diamandis, E. P.; Christopoulos, T. K. *Clin. Chem.* 1991, 37, 625.
Fintschenko, Y.; Wilson, G. S. *Mikrochimica Acta* 1998, 129, 7.
Huang, T. T.; Sturgis, J.; Gomez, R.; Geng, T.; Bashir, R.; Bhunia, A. K.; Robinson, J. P.; Ladisch, M. R. *Biotechnol. Bioeng.* 2003, 81, 618.
Wertz, C. F.; Santore, M. M. *Langmuir* 2001, 17, 3006.
Wilde, L. M.; Farace, G.; Roberts, C. J.; Davies, M. C.; Sanders, G. H. W.; Tendler, S. J. B.; Williams, P. M. *The Analyst* 2001, 126, 195.

We claim:

1. A plasmonic crystal comprising:
a substrate having a first surface with a plurality of features provided in a first array, said substrate comprising a dielectric material; wherein said substrate comprises a nanoimprinted or replica-molded structure; and one or more films comprising an electrically conductive material, wherein at least a portion of said one or more films is supported by said first surface, and wherein at least a portion of said one or more of said films comprising said electrically conducting material is spatially aligned with each of said features of said first surface;

wherein the spatial distribution, physical dimensions or both of said features of said first array are selected such that at least a portion of electromagnetic radiation incident to said plasmonic crystal excites plasmonic responses in said one or more films comprising said electrically conducting material.

2. The plasmonic crystal of claim 1 wherein said features of said first array are selected from the group consisting of:
apertures extending entirely through said substrate;
relief features extending from said substrate; and
recessed features extending into said substrate.

3. The plasmonic crystal of claim 1 wherein at least a portion of said features of said first array are nanosized features or nanostructured features.

4. The plasmonic crystal of claim 1 wherein said features extend heights into said substrate or extend heights away from said substrate selected from the range of 5 nanometers to 5 microns.

5. The plasmonic crystal of claim 1 wherein said features of said first array have cross sectional shapes selected from the group consisting of circular, square, rectangular, trapezoidal, ellipsoid, triangular or any combination of these.

6. The plasmonic crystal of claim 1 wherein said features of said first array have submicron cross sectional dimensions.

7. The plasmonic crystal of claim 1 wherein said features are provided in said first array comprising a periodic array.

8. The plasmonic crystal of claim 7 wherein said first array further comprises at least one defect in said periodic array.

9. The plasmonic crystal of claim 1 wherein said features of said first array are recessed features, relief features, apertures or any combination of these, wherein said one or more films comprising said electrically conductive material comprises a continuous film supported by said first surface and covering at least a portion of said features provided in said first array.

10. The plasmonic crystal of claim 9 wherein said continuous film is a unitary film.

11. The plasmonic crystal of claim 9 wherein said continuous film is provided in physical contact with said first surface.

12. The plasmonic crystal of claim 9 wherein said continuous film is provided in conformal contact with said first surface.

13. The plasmonic crystal of claim 9 wherein each of said features have side surfaces and a top surface or a bottom surface; wherein said continuous film covers said side surfaces and said top surface or said bottom surface of at least a portion of said features.

14. The plasmonic crystal of claim 9 further comprising an additional substrate in contact with said substrate having said first surface, wherein at least a portion of said features of said first array are apertures extending through said substrate having said first surface, wherein said additional substrate is positioned such that said apertures in said substrate having said first surface expose exposed regions of said additional substrate, and wherein said continuous film covers at least a portion of said exposed regions of said additional substrate.

15. The plasmonic crystal of claim 1 wherein said one or more films comprise:
a first film supported by a portion of said first surface, and
a plurality of films provided in a second array, wherein at least one of said films of said second array is spatially aligned with each of said features of said first surface; and wherein at least a portion of said films of said second array are physically displaced from said first film.

16. The plasmonic crystal of claim 15 wherein said first film is provided in a first layer and said films of said second array are provided in a second layer, wherein said plasmonic crystal has a multilayered geometry.

17. The plasmonic crystal of claim 16 wherein said first layer having said first film is separated from said second layer having said array of second films by distances selected over the range of about 5 nanometers to about 5 microns.

18. The plasmonic crystal of claim 15 wherein said first array of features comprises an array of recessed features having bottoms surface or relief features having top surfaces; wherein at least a portion of said films of said second array are positioned on said bottom surfaces or said top surface of said features.

19. The plasmonic crystal of claim 15 wherein said first array of features comprises recessed features, relief features or apertures having side surfaces, wherein said one or more films comprising said electrically conducting material further comprise films covering a portion of said side surfaces of said features.

20. The plasmonic crystal of claim 1 wherein said substrate comprises a polymer material.

21. The plasmonic crystal of claim 1 comprising a three dimensional plasmonic crystal.

22. The plasmonic crystal of claim 1 wherein said one or more films comprising said electrically conducting material comprise a metallic or semiconducting optical grating structure.

23. The plasmonic crystal of claim 1 wherein said one or more films comprising an electrically conducting material comprise one or more metal or semiconductor films having thicknesses selected from the range of about 5 nanometers to about 5 microns.

24. The plasmonic crystal of claim 1 wherein a portion of said one or more films of said electrically conductive material have the same cross sectional shapes as at least a portion of said features of said first array.

25. The crystal of claim 1, wherein said substrate comprises a nanoimprinted or replica-molded polymer layer having a plurality of recessed features provided in said first array.

26. The crystal of claim 25, wherein said recessed features extend lengths less than 500 nanometers and have diameters less than 500 nanometers.

27. The crystal of claim 25, wherein said substrate further comprises a glass layer provided in contact with said nanoimprinted or replica-molded polymer layer.

28. The crystal of claim 25, wherein said nanoimprinted or replica-molded polymer layer is a polyurethane layer.

29. The crystal of claim 25, wherein said one or more films comprise a continuous gold film in conformal contact with said first surface of said substrate.

30. The crystal of claim 29, wherein said continuous gold film has a substantially uniform thickness.

31. The crystal of claim 29, wherein said continuous gold film has a thickness selected from the range of 20 nm to 70 nm.

32. The crystal of claim 25, wherein said films are functionalized to provide selective binding to one or more molecules to be sensed.

33. The crystal of claim 32, wherein said films are functionalized by incorporation of proteins, peptides, oligonucleotides, DNA molecules, RNA molecules, lipids, carbohydrates, polysaccharides; glycoproteins, lipoproteins, or sugars into said films of the plasmonic crystal.

34. A surface plasmon resonance sensor comprising:

an optical source for generating electromagnetic radiation incident to a plasmonic crystal;

said plasmonic crystal positioned to receive said electromagnetic radiation from said optical source, said plasmonic crystal comprising:

a substrate having a first surface with a plurality of features provided in a first array, said substrate comprising a dielectric material; and one or more films comprising an electrically conductive material, wherein at least a portion of said one or more films is supported by said first surface, and wherein at least a portion of said one or more of said films comprising said electrically conducting material is spatially aligned with each of said features of said first surface;

wherein the spatial distribution, physical dimensions or both of said features of said first array are selected such that at least a portion of said electromagnetic radiation incident to said plasmonic crystal excites plasmonic responses in said one or more films comprising said electrically conducting material; and a detector positioned to receive electromagnetic radiation transmitted, scattered or reflected by said plasmonic crystal; said detector capable of detecting changes in the intensity of said electromagnetic radiation transmitted, scattered or reflected by said plasmonic crystal: wherein said detector detects an image of said electromagnetic radiation transmitted, scattered or reflected by said plasmonic crystal.

35. The sensor of claim 34 further comprising a means for providing a material to be sensed proximate to said one or more films of said electrically conducting material, wherein said material to be sensed changes the refractive index proximate to said one or more films of said electrically conducting material.

36. The sensor of claim 34 wherein said for means for providing a material to be sensed proximate to said one or more films comprising an electrically conducting material comprises a nanofluidic system, microfluidic system or a microarray system.

37. The sensor of claim 34 wherein an external surface of said films of said electrically conducting material is functionalized to provide selective binding with one or more analytes.

38. The sensor of claim 37 wherein said external surface of said one or more films of said electrically conducting material is functionalized by incorporation of one or more molecules selected from the group consisting of: proteins, peptides, oligonucleotides, DNA molecules, RNA molecules, lipids, carbohydrates, polysaccharides; glycoproteins, lipoproteins, sugars and candidate molecules, into said one or more films of said electrically conducting material.

39. The sensor of claim 34 wherein said plasmonic crystal is an integrated component of a microarray system, nanofluidic system or a microfluidic system.

40. The sensor of claim 34, wherein said substrate of said plasmonic crystal comprises a nanoimprinted or replica-molded structure.

41. The sensor of claim 40, wherein said substrate of said plasmonic crystal comprises a nanoimprinted or replica-molded polymer layer having a plurality of recessed features provided in said first array.

42. The crystal of claim 41, wherein said substrate further comprises a glass layer provided in contact with said nanoimprinted or replica-molded polymer layer.

43. The crystal of claim 41, wherein said nanoimprinted or replica-molded polymer layer is a polyurethane layer.

* * * * *